(12) United States Patent
Ito

(10) Patent No.: US 9,372,072 B2
(45) Date of Patent: Jun. 21, 2016

(54) PARTICLE MEASURING DEVICE AND PARTICLE MEASURING METHOD

(75) Inventor: Nobuaki Ito, Tokyo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 833 days.

(21) Appl. No.: 13/637,614

(22) PCT Filed: Apr. 1, 2011

(86) PCT No.: PCT/JP2011/058399
§ 371 (c)(1),
(2), (4) Date: Sep. 26, 2012

(87) PCT Pub. No.: WO2011/125927
PCT Pub. Date: Oct. 13, 2011

(65) Prior Publication Data
US 2013/0027540 A1 Jan. 31, 2013

(30) Foreign Application Priority Data

Apr. 1, 2010 (JP) ................................. 2010-084986

(51) Int. Cl.
*G06K 9/78* (2006.01)
*H04N 7/18* (2006.01)
(Continued)

(52) U.S. Cl.
CPC ............ *G01B 11/08* (2013.01); *G01N 15/1463* (2013.01); *G01N 21/8806* (2013.01); *G01N 2021/4771* (2013.01)

(58) Field of Classification Search
CPC .................................................. G01N 21/8806
See application file for complete search history.

(56) References Cited

U.S. PATENT DOCUMENTS 5,680,207 A * 10/1997 Hagiwara .................. 356/237.3
5,790,246 A * 8/1998 Kuhnell et al. ................. 356/72

(Continued)

FOREIGN PATENT DOCUMENTS

JP 60-205337 A 10/1985
JP 62-105031 A 5/1987

(Continued)

OTHER PUBLICATIONS

Feng et al. "Accurate particle position measurement from images" Review of Scientific Instruments 78, 053704 (2007); doi: 10.1063/1.2735920.*

(Continued)

*Primary Examiner* — William C Vaughn, Jr.
*Assistant Examiner* — Stuart Bennett
(74) *Attorney, Agent, or Firm* — Birch, Stewart, Kolasch & Birch, LLP

(57) ABSTRACT

This particle measuring device includes a stage, a reflected light illuminating device, a transmitted light illuminating device, an illumination control device, an imaging device, and an image processing device. Based on a transmitted light image acquired by imaging an opaque fine particle group using transmitted light and a reflected light image acquired by imaging an opaque fine particle group using reflected light, by associating transmitted light particles present in the transmitted light image and reflected light particles present in the reflected light image with each other using a predetermined method, various characteristics (the position, the size, the brightness level, and the like) of individual particles out of a fine particle group are simultaneously measured.

23 Claims, 11 Drawing Sheets

(51) Int. Cl.
 G01B 11/08 (2006.01)
 G01N 15/14 (2006.01)
 G01N 21/88 (2006.01)
 G01N 21/47 (2006.01)

(56) References Cited

U.S. PATENT DOCUMENTS

| | | | |
|---|---|---|---|
| 2006/0181700 A1* | 8/2006 | Andrews et al. | 356/237.2 |
| 2009/0134355 A1* | 5/2009 | Konabe et al. | 252/88.1 |
| 2009/0304262 A1* | 12/2009 | Harabe | 382/152 |

FOREIGN PATENT DOCUMENTS

| JP | 4-343047 A | | 11/1992 |
|---|---|---|---|
| JP | 6-160065 A | | 6/1994 |
| JP | 08-178843 | * | 7/1996 |
| JP | 8-178843 A | | 7/1996 |
| JP | 8-189903 A | | 7/1996 |
| JP | 2000-180369 A | | 6/2000 |
| JP | 2000-304702 A | | 11/2000 |
| JP | 2001-503848 A | | 3/2001 |
| JP | 2002-188990 A | | 7/2002 |
| JP | 2002-365222 A | | 12/2002 |
| JP | 2003-75353 A | | 3/2003 |
| JP | 2006-189354 A | | 7/2006 |
| JP | 2006-198354 A | | 8/2006 |
| JP | 2008-25446 A | | 2/2008 |
| JP | 2008-76333 A | | 4/2008 |

OTHER PUBLICATIONS

International Search Report issued in PCT/JP2011/058399, dated May 31, 2011.
Japanese Notice of Allowance for Application No. 2012-509626 dated Sep. 4, 2012.
Chinese Office Action (Search Report Only) dated May 29, 2013 issued in Chinese Patent Application No. 201180017139.1 (English translation provided).

* cited by examiner

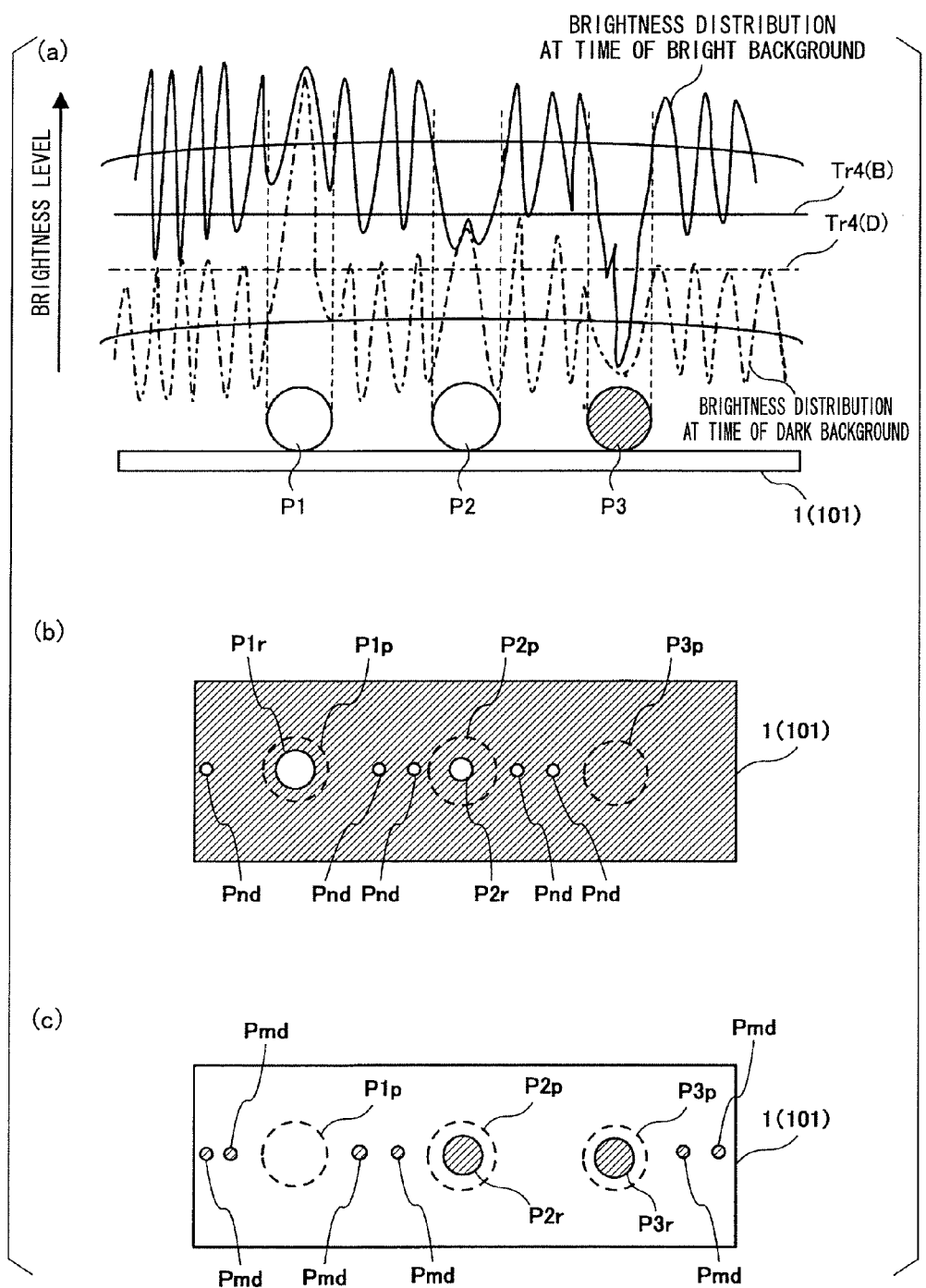

PARTICLE MEASURING DEVICE AND PARTICLE MEASURING METHOD

TECHNICAL FIELD

The present invention relates to a particle measuring device and a particle measuring method for measuring the position, the size, the brightness, and the like of a fine particle.

Priority is claimed on Japanese Patent Application No. 2010-084986, filed Apr. 1, 2010, the content of which is incorporated herein by reference.

BACKGROUND ART

As a method of evaluating the shape, the size, the quality, and the like of various specimen particles, a method (particle image processing and measuring) is widely used in which the shape, the size, the brightness, and the like of a specimen particle are measured by performing image processing of an image that is acquired by imaging the specimen particle using an imaging device.

As such a particle image processing and measuring method, there is a method in which light is emitted from the upper side or the lower side of a specimen particle using a single illumination device as an illumination device used at the time of photographing, a method in which light is emitted simultaneously from the upper side and the lower side of a specimen particle using a plurality of illumination devices, or a method in which light is emitted from the upper side and the lower side of a specimen particle through independent control processes by independently controlling a plurality of illumination devices.

First, as the method using a single illumination, for example, in Patent Document 1, a method is disclosed in which a specimen particle is sprayed onto a photographing pasteboard that represents a contrast with the specimen particle, and after photographing using reflective light of the illumination that is emitted from the upper side of the specimen particle, particle image processing and measuring is performed. In addition, in Patent Document 2, a reflective plate is arranged on the lower side of a specimen particle, and, after photographing is performed mainly using reflected transmitted light of the illumination that is emitted from the upper side of the specimen particle, particle image processing and measuring is performed. Furthermore, in Patent Document 3, a method is disclosed in which strong light is emitted from the rear face of a dust gathering plate, and, after photographing using light scatted by dusts, particle image processing and measuring is performed.

Next, as the method using simultaneous illumination emitted from the upper side and the lower side of a specimen particle, for example, in Patent Document 4, a method is disclosed, after photographing is performed using light incident from illuminations located on the upper side and the lower side of a micro plate in which a specimen particle is placed, particle image processing and measuring is performed. In addition, in Patent Document 5, a method is disclosed in which an air bubble and a foreign material are discriminated from each other by simultaneously emitting transmitted light and reflected light onto a transparent container. According to the method disclosed in Patent Document 5, an air bubble is recognized as a particle that has high brightness.

Next, as the method using independent illuminations emitted from the upper side and the lower side of a specimen particle, for example, in Patent Document 6, a method is disclosed in which a particle imaging process is performed by emitting transmitted light onto a film, and, after the position of an air bubble within the film is measured, the reflectance of the air bubble is measured by outputting the reflected light, whereby an air bubble and a scratch and a dust are discriminated from each other. In addition, in Patent Document 7, a method is disclosed in which the amount of transmitted light of a particle is measured by emitting transmitted light onto a grain that is a transparent or a semi-transparent particle, and, next, the color of the particle is measured by outputting reflected light, whereby the quality of a fine particle or the like is determined.

CITATION LIST

Patent Document

[Patent Document 1] Japanese Unexamined Patent Application, First Publication No. 2002-188990

[Patent Document 2] Japanese Unexamined Patent Application, First Publication No. 2008-76333

[Patent Document 3] Japanese Unexamined Patent Application, First Publication No. 2003-75353

[Patent Document 4] Japanese Unexamined Patent Application, First Publication No. S62-105031

[Patent Document 5] Japanese Unexamined Patent Application, First Publication No. S60-205337

[Patent Document 6] Japanese Unexamined Patent Application, First Publication No. H08-189903

[Patent Document 7] Japanese Unexamined Patent Application, First Publication No. 2000-180369

SUMMARY OF INVENTION

Technical Problem

However, in the method disclosed in Patent Document 1 described above, since imaging is performed by using only reflected light, there is a problem in that the measurement accuracy of the dimensions of a specimen particle is low. The reason for this is that the brightness of light reflected from a particle significantly differs depending on the position even for a uniform material. In other words, there is a difference in the angle of reflection of light that is incident from the illumination device depending on a position on the particle surface, and, generally, a peripheral edge portion of a particle is imaged to have low brightness. In addition, there may be a highlight due to specular reflection. Particularly, in a case where an individual fine particle is recognized using a small number of pixels, the effect is remarkable. In addition, in the method disclosed in Patent Document 1, since the brightness of the background of a particle image is fixed, in a case where the brightness distribution of specimen particles is large, there is a problem in that the particle image may have the same color as that of the background, so that there is a particle that cannot be identified.

In addition, in the method disclosed in Patent Document 2, only transmitted light is used, and accordingly, there is a problem in that information relating to the brightness of a particle cannot be acquired while the dimensions of the particle can be measured.

Furthermore, in the method disclosed in Patent Document 3, in a case where the scattered light is strong, imaging is performed with high brightness also for pixels that are located on the periphery of a pixel within an area in which the specimen particle is present, and accordingly, there is a problem in that the measurement accuracy of the dimensions of the specimen particle is low.

In addition, in the method disclosed in Patent Document 4, although the illumination devices located on both the upper side and the lower side are used, only the illumination devices are simultaneously used, and accordingly, it is difficult to identify a specimen particle having brightness that is close to the brightness according to the illumination emitted from the lower side as a particle. Furthermore, even in a case where the specimen particle can be identified, generally, the boundary of the particle is not clear, and accordingly, there is a problem in that the measurement accuracy of the dimensions of the specimen particle is low.

In addition, in the method disclosed in Patent Document 5, since illumination is performed simultaneously from the upper side and the lower side, there are the same problems as those of the method disclosed in Patent Document 4. Furthermore, since the scattering of light for a transparent particle such as an air bubble is strong, there is a problem in that the dimension measurement accuracy of a specimen particle is low.

In addition, in the method disclosed in Patent Document 6, only a transparent particle having extremely high reflectance such as an air bubble can be recognized. In other words, for a transparent particle such as an air bubble, only a part of the peripheral edge portion (edge) of the particle is recognized by performing imaging using transmitted light, scattered light is strong in the reflected light, and accordingly, there is a problem in that the dimension measurement accuracy is low. Furthermore, as disclosed in Patent Document 6, a dust has brightness that is almost the same as that of the background, and accordingly, quantitative brightness measurement cannot be performed.

In addition, in the method disclosed in Patent Document 7, first, since the scattering of transmitted light for a transparent particle such as a grain is strong, similarly to Patent Document 6 or the like, the dimension measurement accuracy is low.

Second, in the method disclosed in Patent Document 7, when a binarization process is performed for a transmission image (an image captured by using transmitted light) with high brightness that is allowed for a particle, there is a high possibility that a colored transparent dirt on a substrate of a specimen particle or a contaminating particle (it can be easily attached to the lower face of the transparent substrate, a lens surface, a sample transparent protection board, or the like and is imaged as a spot having intermediate brightness) that is present at a position separate from a test face within a photographing system, which cannot be avoided in a sample generating operation or a measurement operation, is misrecognized as a particle.

Third, in the method disclosed in Patent Document 7, although a particle (transmitted light identified-particle) that is identified from an image photographed using transmitted light and a particle (reflected light identified-particle) that is identified from an image photographed using reflected light are associated with each other through one-to-one correspondence without any description, in a case where image processing is performed for a general fine particle having a large distribution of the size or the brightness, there are a few cases in which one-to-one correspondence is formed as above. Generally, a case where a corresponding particle is not present or a case where a plurality of particles are in correspondence with one particle frequently occurs, and thus, comprehensive characteristics (the shape, the dimensions, the brightness, and the like) of a particle cannot be determined through image processing without contriving the correspondence between a transmitted light identified-particle and a reflected light identified-particle. In addition, in the method disclosed in Patent Document 3, since the measurement target is a few grains, the size or the color variation of the target is originally small, and photographing is performed such that a plurality of pixels are in correspondence with one grain, it is understood that one-to-one correspondence can be formed without using a special particle correspondence method.

Fourth, in the method disclosed in Patent Document 7, since illumination from the upper side and illumination from the lower side are not simultaneously emitted, there is no option of the background color at the time of photographing using reflected light output from a grain in accordance with the illumination from the upper side. In this method, although a grain such as white rice is the measurement target, and there is no problem for only a black background, when a general fine particle is photographed, it is assumed that there are many particles of which the brightness cannot be discriminated from that of the background.

As above, until now, a method, in which various characteristics (the position, the size, the brightness, and the like) of individual particles of a fine particle group are simultaneously measured with an opaque fine particle group having a large distribution of the size, the brightness, or the like as a target, has not been proposed.

Therefore, the present invention is devised in view of the above-described problems, and an object of the present invention is to provide a particle measuring device and a method of measuring a particle that are capable of simultaneously measuring various characteristics (the position, the size, the brightness, and the like) of individual particles of a fine particle group with an opaque fine particle group having a large distribution of the size, the brightness, or the like.

Solution to Problem

The present inventors, in order to solve the above-described problems, as a result of diligently repeating researches, proposes a new technique in which measurement targets are limited to an opaque fine particle group, based on a transmitted light image acquired by capturing a fine particle group using transmitted light and a reflected light image acquired by capturing the fine particle group using reflected light, transmitted light particles present in the transmitted light image and reflected light particles present in the reflected image are associated with each other, and, have found that various characteristics (the position, the size, the brightness level, and the like) of individual particles can be simultaneously measured even in a case where the measurement target is a fine particle group having a large distribution in the size, the brightness level, or the like, and have completed the present invention based on the knowledge.

(1) In other words, according to an aspect of the present invention, there is provided a particle measuring device including: a stage on which a transparent substrate having an opaque fine particle sprayed thereon is placed or the fine particle is directly sprayed; a reflected light illuminating device that is disposed on a placement face side of the stage and emits first light having predetermined device light emitting face luminance toward the stage; a transmitted light illuminating device that is disposed on a side of the stage that is opposite to the placement face and emits second light having predetermined device light emitting face luminance toward the stage; an illumination control device that individually controls the device light emitting face luminance of the first light and the device light emitting face luminance of the second light; an imaging device that includes a transmitted light image generating unit that generates a transmitted light image acquired by imaging the fine particle in a state being controlled by the illumination control device such that the device light emitting face luminance of the second light is predetermined luminance other than zero, and the device light emitting face luminance of the first light is zero and a reflected light image generating unit that generates a reflected light image acquired by imaging the fine particle in a state being controlled by the illumination control device such that the device light emitting face luminance of the second light is predetermined luminance set in accordance with one, two or more conditions and the device light emitting face luminance of the first light is predetermined luminance other than zero, and is disposed on the placement face side with respect to the stage; and an image processing device that, by comparing positions and sizes of one, two, or more transmitted light particles that are identified as candidates for a captured image of the fine particle within the transmitted light image and positions and sizes of one, two, or more reflected light particles that are identified as candidates for a captured image of the fine particle within the reflected light image, associates the transmitted light particle and the reflected light particle having a difference between the positions and the sizes within a predetermined range, calculates the position and the size of the transmitted light particle as a position and a size of the fine particle, and calculates a representative brightness level of the reflected light particles or the transmitted light particles as a brightness level of the fine particle, based on a result of the association.

(2) In the particle measuring device described in (1) described above, the image processing device may include: a transmitted light particle detecting unit that specifies a pixel area in which pixels having brightness levels lower than a predetermined brightness level are aggregated in pixel coordinates of the transmitted light image as an area in which the transmitted light particle is present based on an image brightness distribution that is acquired by binarizing the transmitted light image using a predetermined brightness threshold value and detects position coordinates of a pixel within the area in which the transmitted light particle is present; a transmitted light particle information calculating unit that calculates at least the position and the size of the transmitted light particle based on a detection result of the transmitted light particle detecting unit; a reflected light particle detecting unit that specifies a pixel area in which pixels each having a brightness level difference from a peripheral pixel that is a predetermined value or more are aggregated in pixel coordinates of the reflected light image as an area in which the reflected light particle is present based on a brightness distribution of the reflected light image and detects position coordinates of a pixel within the area in which the reflected light particle is present; a reflected light particle information calculating unit that calculates at least the position and the size of the reflected light particle based on a detection result acquired by the reflected light particle detecting unit; an association processing unit that compares the position and the size of the reflected light particle with the positions and the sizes of all the transmitted light particles based on a calculation result of the transmitted light particle information calculating unit and a calculation result of the reflected light particle information calculating unit, associates the transmitted light particle and the reflected light particle having differences in the position and the size that are within predetermined ranges with each other, and exclude the reflected light particle that is not associated with any one of the transmitted light particles from a candidate for a captured image of the fine particle; and a particle information calculating unit that calculates the position and the size of the transmitted light particle as the position and the size of the fine particle, calculates the representative brightness level of the reflected light particle that is associated with the transmitted light particle as a brightness level of the fine particle, and calculates the brightness level of the transmitted light particle that is not associated with any one of the reflected light particles as a predetermined brightness level.

(3) In the case of the particle measuring device described in (2) described above, it may be configured such that the reflected light image generating unit generates the reflected light image in a state in which the device light emitting face luminance of the second light is set by the illumination control device such that the brightness level of a background of the reflected light particle on the reflected light image is higher than a brightness threshold value used for identifying a level of the brightness of a particle, the reflected light particle detecting unit specifies a pixel area in which pixels having brightness levels lower than a predetermined brightness level are aggregated in the pixel coordinates of the reflected light image as an area in which the reflected light particle is present based on a brightness distribution of an image that is acquired by binarizing the reflected light image using a brightness threshold value used for identifying the level of the brightness of the particle and detects position coordinates of the pixel located within the area in which the reflected light particle is present, and the particle information calculating unit identifies the fine particle corresponding to the transmitted light particle that is associated with the reflected light particle as a dark-color particle having a brightness lower than a brightness threshold value used for identifying the level of brightness of the particle and identifies the fine particle corresponding to the transmitted light particle that is not associated with any reflected particle as a bright-color particle having a brightness level higher than the brightness threshold value used for identifying the level of the brightness of the particle.

(4) In the case of the particle measuring device described in (2) described above, it may be configured such that the reflected light image generating unit generates the reflected light image in a state in which the device light emitting face luminance of the second light is set by the illumination control device such that the brightness level of a background of the reflected light particle on the reflected light image is lower than a brightness threshold value used for identifying a level of the brightness of a particle, the reflected light particle detecting unit specifies a pixel area in which pixels having brightness levels higher than a predetermined brightness level are aggregated in the pixel coordinates of the reflected light image as an area in which the reflected light particle is present based on a brightness distribution of an image that is acquired by binarizing the reflected light image using a brightness threshold value used for identifying the level of the brightness of the particle and detects position coordinates of the pixel located within the area in which the reflected light particle is present, and the particle information calculating unit identifies the fine particle corresponding to the transmitted light particle that is associated with the reflected light particle as a bright-color particle having a brightness higher than a brightness threshold value used for identifying the level of brightness of the particle and identifies the fine particle corresponding to the transmitted light particle that is not associated with any reflected particle as a dark-color particle having a brightness level lower than the brightness threshold value used for identifying the level of the brightness of the particle.

(5) In the case of the particle measuring device described in (2) described above, it may be configured such that the reflected light image generating unit generates a dark-background reflected light image that is acquired by imaging the fine particle in a state in which the device light emitting face luminance of the second light is set by the illumination control device such that the brightness level of a background of the reflected light particle on the reflected light image is lower than a first brightness threshold value used for identifying a level of the brightness of a particle, the reflected light image generating unit generates a bright-background reflected light image that is acquired by imaging the fine particle in a state in which the device light emitting face luminance of the second light is set by the illumination control device such that the brightness level of a background of the reflected light particle on the reflected light image is higher than a second brightness threshold value, which is a brightness threshold value lower than the first brightness threshold value, used for identifying the level of the brightness of the particle, the reflected light particle detecting unit specifies a pixel area in which pixels having high brightness levels are aggregated in the pixel coordinates of the reflected light image as an area in which the reflected light particle is present based on a brightness distribution of an image that is acquired by binarizing the dark-background reflected light image using the first brightness threshold value and detects position coordinates of the pixel located within the area in which the reflected light particle is present, the reflected light particle detecting unit specifies a pixel area in which pixels having low brightness levels are aggregated in the pixel coordinates of the reflected light image as an area in which the reflected light particle is present based on a brightness distribution of an image that is acquired by binarizing the bright-background reflected light image using the second brightness threshold value and detects position coordinates of the pixel located within the area in which the reflected light particle is present, the particle information calculating unit identifies the fine particle corresponding to the transmitted light particle that is associated with the reflected light particle that is present within the dark-background reflected light image as a bright-color particle having a brightness level higher than the first brightness threshold value, identifies the fine particle corresponding to the transmitted light particle that is associated with the reflected light particle that is present within the bright-background reflected light image as a dark-color particle having a brightness level lower than the second brightness threshold value, and identifies the fine particle corresponding to the transmitted light particle that is not associated with any of the reflected light particles as an intermediate-color particle having an intermediate brightness level between the bright color particle and the dark color particle.

(6) In the case of the particle measuring device described in (2) described above, it may be configured such that the reflected light image generating unit generates a dark-background reflected light image that is acquired by imaging the fine particle in a state in which the device light emitting face luminance of the second light is set by the illumination control device such that the brightness level of a background of the reflected light particle on the reflected light image is lower than a first brightness threshold value used for identifying a level of the brightness of a particle, the reflected light image generating unit generates a bright-background reflected light image that is acquired by imaging the fine particle in a state in which the device light emitting face luminance of the second light is set by the illumination control device such that the brightness level of a background of the reflected light particle on the reflected light image is higher than a second brightness threshold value, which is a brightness threshold value higher than the first brightness threshold value, the reflected light particle detecting unit specifies a pixel area in which pixels having brightness levels higher than a predetermined brightness level are aggregated in the pixel coordinates of the reflected light image as an area in which the reflected light particle is present based on a brightness distribution of an image that is acquired by binarizing the dark-background reflected light image using the first brightness threshold value and detects position coordinates of the pixel located within the area in which the reflected light particle is present, the reflected light particle detecting unit specifies a pixel area in which pixels having brightness levels lower than a predetermined brightness level are aggregated in the pixel coordinates of the reflected light image as an area in which the reflected light particle is present based on a brightness distribution of an image that is acquired by binarizing the bright-background reflected light image using the second brightness threshold value and detects position coordinates of the pixel located within the area in which the reflected light particle is present, and the particle information calculating unit sets the fine particle corresponding to the transmitted light particle that is associated with the reflected light particle that is present within the dark-background reflected light image as a candidate for a bright-color particle having a brightness level higher than the first brightness threshold value, sets the fine particle corresponding to the transmitted light particle that is associated with the reflected light particle that is present within the bright-background reflected light image as a candidate for a dark-color particle having a brightness level lower than the second brightness threshold value, identifies the fine particle corresponding to the transmitted light particle that is associated with both the reflected light particles that is present within the dark-background reflected light image and the reflected light particle that is present within the bright-background reflected light image as an intermediate-color particle having an intermediate brightness level between the bright-color particle and the dark-color particle, identifies the candidates for the bright-color particle that is not identified as the intermediate-color particle as the bright-color particle, and identifies the candidates for the dark-color particle that are not identified as the intermediate-color particle as the dark-color particle.

(7) In the case of the particle measuring device described in (2) described above, it may be configured such that the illumination control device, in a case where the brightness level of the reflected particle on the reflected light image is higher than a brightness threshold value used for identifying the level of the brightness of the particle, and N is a natural number, can set first device light emitting face luminance to N-th device light emitting face luminance of which the brightness levels satisfy "first brightness level<second brightness level< . . . <N-the brightness level" using the second light, the reflected light image generating unit generates first to N-th reflected light images in a state in which the device light emitting face luminance of the second light is set to the first device light emitting face luminance to the N-th device light emitting face luminance, the reflected light particle detecting unit, based on a brightness distribution of an image that is acquired by binarizing the first to N-th reflected light images using a brightness threshold value used for identifying a level of the brightness of the particle, specifies a pixel area in which pixels having brightness levels lower than a predetermined brightness level are aggregated in the pixel coordinates of the first to N-th reflected light images as an area in which the reflected light particle is present and detects position coordinates of pixels present within the area in which the reflected light particle is present, when n=1 to N, the association processing unit compares a position and a size of the reflected light particle detected in the n-th reflected light image with the position and the size of the transmitted light particle (in the case of n=1, all the transmitted light particles) that is not associated with the reflected light particle detected in the (n−1)-th or a prior reflected light image and associates the transmitted light particle and the reflected light particle having differences in the position and the size are within predetermined ranges, and the particle information calculating unit identifies the brightness level of the fine particle corresponding to the transmitted light particle that is associated with the reflected light particle that is present within the first to N-th reflected light images as first to N-th brightness levels (first brightness level<second brightness level< . . . <N-th brightness level and identifies the fine particle corresponding to the transmitted light particle that is not associated with any reflected light particle as a particle having a highest brightness level.

(8) In the particle measuring device described in any one of (1) to (7) described above, the fine particle may be a falling dust that is originated from an iron manufacturing plant according to a blast furnace method.

(9) In the particle measuring device described in any one of (2) to (7) described above, it may be configured such that the transmitted light particle information calculating unit additionally calculates a diameter of the transmitted light particle, and the particle information calculating unit additionally calculates the diameter of the transmitted light particle as a particle diameter of the fine particle.

(10). According to another aspect of the present invention, there is provided a method of measuring a position, a size, and a brightness level of a fine particle by using a particle measuring device including: a stage on which a transparent substrate having an opaque fine particle sprayed thereon is placed or the fine particle is directly sprayed; an imaging device that is disposed on a placement face side of the stage and images the fine particle; a reflected light illuminating device that is disposed on a placement face side of the stage and emits first light having predetermined device light emitting face luminance toward the stage; and a transmitted light illuminating device that is disposed on a side of the stage that is opposite to the placement face and emits second light having predetermined device light emitting face luminance toward the stage, the method including: generating a transmitted light image acquired by imaging the fine particle using the imaging device in a state in which the device light emitting face luminance of the second light is predetermined luminance other than zero, and the device light emitting face luminance of the first light is zero; generating a reflected light image acquired by imaging the fine particle using the imaging device in a state in which the device light emitting face luminance of the second light is predetermined luminance set in accordance with one or more conditions, and the device light emitting face luminance of the first light is predetermined luminance other than zero; and associating the transmitted light particle and the reflected light particle having a difference between the positions and the sizes within a predetermined range, by comparing positions and sizes of one, two, or more transmitted light particles that are identified as candidates for a captured image of the fine particle within the transmitted light image and positions and sizes of one, two, or more reflected light particles that are identified as candidates for a captured image of the fine particle within the reflected light image, calculating the position and the size of the transmitted light particle as a position and a size of the fine particle, and calculating a representative brightness level of the reflected light particles or the transmitted light particles as a brightness level of the fine particle, based on a result of the association.

(11) In the fine particle measuring method according to (10) described above, the fine particle may be a falling dust that is originated from an iron manufacturing plan according to a blast furnace method.

Advantageous Effects of Invention

According to the present invention, based on a transmitted light image acquired by imaging an opaque fine particle group using transmitted light and a reflected light image acquired by imaging an opaque fine particle group using reflected light, by associating transmitted light particles present in the transmitted light image and reflected light particles present in the reflected light image with each other using a predetermined method, various characteristics (the position, the size, the brightness level, and the like) of individual particles out of a fine particle group can be simultaneously measured.

BRIEF DESCRIPTION OF DRAWINGS

FIG. 11 is an explanatory diagram that illustrates an example of the image processing method using a reflected light image according to a fourth embodiment of the present invention.

DESCRIPTION OF EMBODIMENTS

Figure 1:
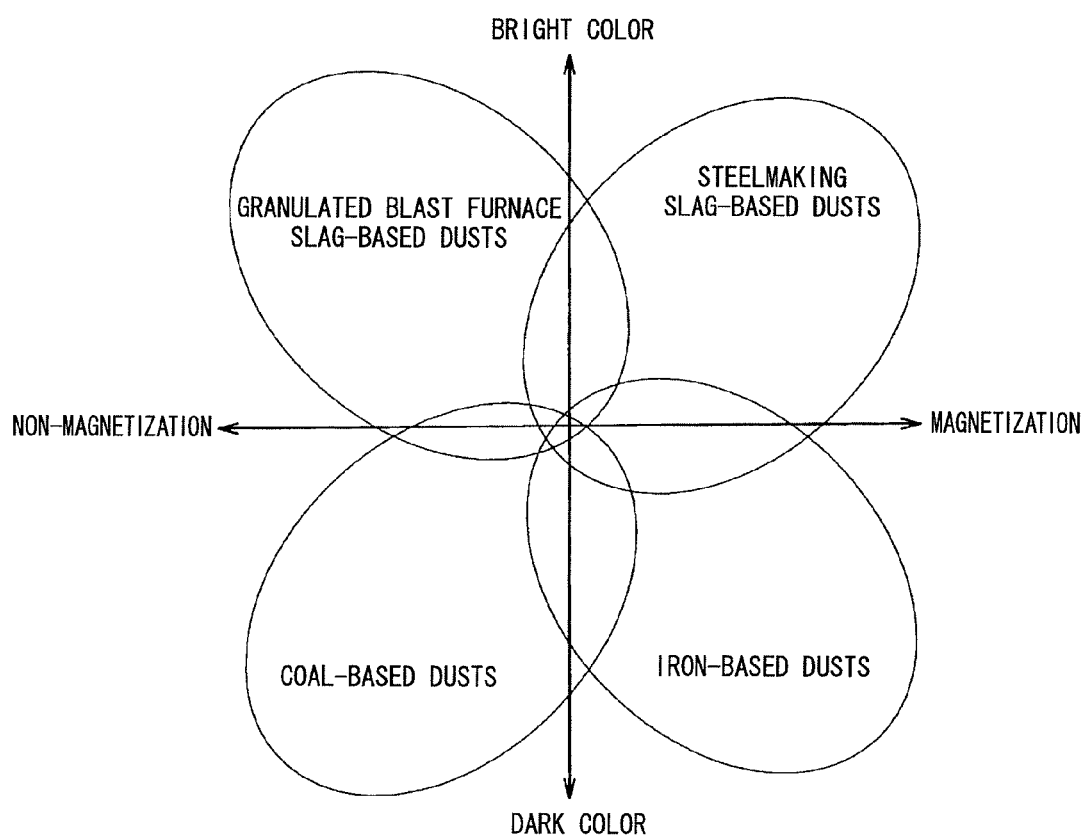
FIG. 1 is an explanatory diagram that illustrates schematic relation between the magnetization property and the brightness of each dust type of falling dusts that are originated from an iron manufacturing plant according to a blast furnace method.

Hereinafter, preferred embodiments of the present invention will be described in detail with reference to the accompanying drawings. In this specification and the drawings, the same reference numeral is assigned to constituent elements having the substantially same function, and duplicate description thereof will not be presented.

[Overview and Superiority of Present Invention]

The present invention relates to an analysis device and an analysis method of fine particles that are generated in various industries. More specifically, the present invention relates to a particle measuring device that includes: a stage on which a transparent substrate having opaque fine particles scattered thereon is placed; an imaging device that images the fine particles placed on the substrate; a transmitted light illuminating device that emits light of predetermined device light emitting face luminance (device light emitting face luminance of second light, hereinafter, simply referred to as luminance or predetermined luminance) from the lower side of the stage toward the stage; and a reflected light illuminating device that emits light of predetermined device light emitting face luminance (device light emitting face luminance of first light, hereinafter, simply referred to as luminance or predetermined luminance) from the upper side of the stage toward the stage and measures the positions, the sizes, and the brightness levels of the fine particles, and a particle measuring method for measuring the position, the size, and the brightness of a fine particle using the particle measuring device. Before the preferred embodiments of the present invention will be described, first, a technical idea that is the base of the present invention and the superiority of the present invention will be described.

In addition, the "device light emitting face luminance of first light" according to the present invention represents the luminance at a light source light emitting face of the reflected light illuminating device. Similarly, the "device light emitting face luminance of second light" according to the present invention represents the luminance of the light source light emitting face of the transmitted light illuminating device.

(Accuracy of Analysis)
<Measurement Target>

In the present invention, by limiting the measurement target to an opaque fine particle (as a whole, a particle of which the diameter (equivalent circle diameter) is 10 μm or more and several hundreds of μm or less), the possibility of misrecognizing a contaminating material that cannot be avoided in a sample generating operation or a sample measuring operation, in other words, a colored transparent dirt placed on a substrate or a contaminating particle that is present at a position that is separate from a test face within the photographing system as a measurement target particle can markedly decrease. Particularly, there are many semi-transparent materials such as chemical scraps as contaminating particles that are present at the time of imaging particles, and accordingly, by performing image processing also for the contaminating particles, the contaminating particles can be eliminated from candidates for fine particles that are measurement targets. Since there are many contaminating materials that are transparent or semi-transparent, such an operation can be pertained in the present invention, by limiting the measurement targets as opaque fine particles, and only opaque particles are recognized as particles (transmitted light particles) in an image captured when imaging is performed using only illumination (transmitted light), which is located from the lower side of the stage, according to the transmitted light illuminating device, and such particles can be determined as real fine particles that are measurement targets. On the other hand, in a case where imaging is performed using only transmitted light, the brightness of captured image of contaminating materials is the same as that of the background, and accordingly, the contaminating materials that are transparent or opaque cannot be recognized as particles.

<Association Between Transmitted Light Particle and Reflected Light Particle>

In addition, in the present invention, logic for associating a particle (transmitted light particle) that is recognized within an image captured using only transmitted light and a particle (reflected particle) that is recognized within an image captured using also illumination (reflected light) emitted from the upper side of the stage in addition to the transmitted light having predetermined luminance is defined. Accordingly, even in a case where the measurement target is a fine particle having a large distribution of the size, the brightness, or the like, by combining information (mainly, information such as the shape, the dimensions, and the like of a fine particle) acquired from the transmitted light particle and information (mainly, information of the brightness of a fine particle) acquired from the reflected light particle, comprehensive characteristic information of a fine particle as the measurement target can be calculated.

As specific examples of association between the transmitted light particle and the reflected light particle, there are followings.

First, since an object that is not recognized as a transmitted light particle but is recognized as a reflected light particle is considered as being a transparent or a semi-transparent material, as described above, the object is excluded from a fine particle candidate for a measurement target as a contaminating material or the like.

Second, in a case where a plurality of reflected light particles are associated with one transmitted light particle, it is assumed that the actual number of the fine particle is one, and remaining reflected light particles acquired by excluding one reflected light particle are highlights or the like, and representative brightness of a reflected light particle that has the highest relevance (to be described in detail) to the transmitted light particle is calculated as the brightness of a fine particle that is the measurement target.

Third, in a case where one reflected light particle is associated with a plurality of transmitted light particles, the number of actual fine particles is the same as that of transmitted light particles, the positions of all the fine particles are close to each other, and the brightness thereof is of a same level, and accordingly, it is assumed that the reflected light particle is recognized as one particle. Accordingly, representative brightness of one reflective light particle is calculated as the brightness of a fine particle that is in correspondence with all the transmitted light particles.

Fourth, an object that is not recognized as a reflected light particle but is recognized only as a transmitted light particle is considered as an opaque material, and thus the object is determined as a fine particle that is the measurement target. In addition, an object that is not recognized as a reflected light particle is assumed to have brightness that is in the same level as that of the background of an image that is captured using reflected light, and accordingly, the brightness of the fine particle that is the measurement target is assumed to have predetermined brightness (brightness that is in the same level as that of the background), and the brightness of the fine particle is calculated.

As above, by processing an image (transmitted light image) that is acquired by capturing a fine particle, which is the measurement target, using only transmitted light, the information of the shape, the dimensions, and the like of the fine particle is acquired, and by processing an image (reflected light image) that is acquired by capturing the fine particle, which is the measurement target, using reflected light together with the transmitted light, information of the brightness of the fine particle can be acquired. In addition, in the particle measuring device and the particle measuring method according to the present invention, the logic for association between the transmitted light particle and the reflected light particle is defined, and accordingly, by performing image processing using the transmitted light image and the reflected light image, comprehensive characteristic information of a fine particle that is the measurement target can be calculated, whereby the accuracy of the analysis (measurement) can be improved.

(Convenience of Analysis)

In the present invention, only by operating two types of illumination devices (the transmitted light illuminating device and the reflected light illuminating device) without changing the position of a fine particle that is the measurement target sprayed onto a substrate, the brightness of the background of an image of the fine particle can be changed in a convenient manner, and it is easy to take particles (a transmitted light particle and a reflected light particle) to be in correspondence with images having different background brightness levels.

(Application to Specifying Dust Type of Falling Dust Originated from Iron Manufacturing Plant)

In addition, the particle measuring device and the particle measuring method according to the present invention are useful particularly when a dust type of falling dusts that are generated in an iron manufacturing plant based on a blast furnace method is specified. While the falling dusts that are generated in an iron manufacturing plant based on a blast furnace method cause problems such as staining a vehicle that travels inside the iron manufacturing plant, in a case where the dust type of the falling dusts can be specified, a generation source of the falling dust can be specified, and it is possible to take a countermeasure for suppressing the generation of the falling dusts.

Here, advantages acquired in a case where the present invention is applied to the specifying of the dust type of falling dusts that are originated from an iron manufacturing plant will be described with reference to FIG. 1. FIG. 1 is an explanatory diagram that illustrates schematic relation between the magnetization property and the brightness of each dust type of falling dusts that are originated from an iron manufacturing plant according to a blast furnace method.

Generally falling dusts that are originated from an iron manufacturing plant according to a blast furnace method are mainly classified into four dust types of a coal-based dust that includes coal, coke, and the like, a ferrous dust that includes an iron ore, a sintered ore, a brown iron oxide, and the like, a blast furnace slag-based dust that includes granulated blast furnace slag, air-cooled blast furnace slag, and the like, and a steelmaking slag-based dust that includes converter slag, molten iron preliminary processing slag, and the like.

Out of these four dust types, commonly, since the blast furnace slag-based dust and steelmaking slag-based dust are white color-based particles (bright-color particles) having high brightness, and the coal-based dust and the ferrous dust are black color-based particles (dark-color particles) having low brightness, similarly to a conventional technique, by performing image processing for a photographed image using a low-powered optical microscope and identifying the level of the brightness of each dust particle, a dust type that is formed by the blast furnace slag-based dust and the steelmaking slag-based dust and a dust type formed by the coal-based dust and the ferrous dust can be determined.

However, in the classification into only a bright-color pixel and a dark-color particle, a determination between particles having a same brightness level, for example, a determination between a blast furnace slag-based dust and a steelmaking slag-based dust cannot be made. In other words, according to the classification made only based on the level of the brightness by performing image processing, very comprehensively, the dust type of a falling dust (furthermore, a generation source of a falling dust) that is originated from the iron manufacturing plant according to a blast furnace method cannot be specified, whereby the practicality thereof is low.

Thus, in order to specify a dust type of a falling dust that is originated from an iron manufacturing plant according to a blast furnace method (hereinafter, it may be referred to as an "iron manufacturing-originated falling dust"), the inventor focuses on not only the level of the brightness of the dust particle but also the presence of the magnetization property. As a result, the inventor found that the characteristics of a dust can be defined based on a combination of the level of brightness and the presence of the magnetization property, and the dust type of the falling dust originated from the iron manufacturing plant according to a blast furnace method can be specified based on the characteristics of the dust. Described in more detail, the inventor found that a dust type of the iron manufacturing-originated falling dust, which cannot be determined only by performing image processing of an image captured by a low-magnification optical microscope, can be determined as being one of the four types of the coal-based dust, the ferrous dust, the blast furnace slag-based dust and the steelmaking slag-based dust based on the combination of the level of the brightness and the presence of the magnetization property.

In addition, the magnetization property according to the present invention represents a property of being magnetized (having a magnetic property and is attracted by a magnet) by applying a predetermined magnetic force to a target dust particle, and in the present invention, falling dust that are originated from an iron manufacturing plant according to a blast furnace method are classified into magnetizable falling dusts that are magnetized by applying a magnetic force thereto and non-magnetizable falling dusts that are not magnetized even by applying a magnetic force thereto, and the magnetizable falling dusts and the non-magnetizable falling dusts are further classified respectively into bright-color particles and dark-color particles based on the level of brightness.

More specifically, a coal-based dust can be classified into a non-magnetizable dark-color particle that has low brightness (dark color) and no-magnetization property, a ferrous dust can be classified into a magnetizable dark-color particle that has low brightness (dark color) and the magnetization property, a blast furnace slag-based dust can be classified into a non-magnetizable bright-color particle that has high brightness (bright color) and the non-magnetization property, and a steelmaking slag-based dust can be classified into a magnetizable bright-color particle that has high brightness (bright color) and the magnetization property.

As above, according to knowledge found by the inventor, while dust types of iron manufacturing-originated falling dusts can be specified in accordance with the dust characteristics, at this time, the particle measuring device and the particle measuring method according to the present invention can be applied as techniques for identifying the level of the brightness.

First Embodiment (Particle Measuring Device)

Figure 2:
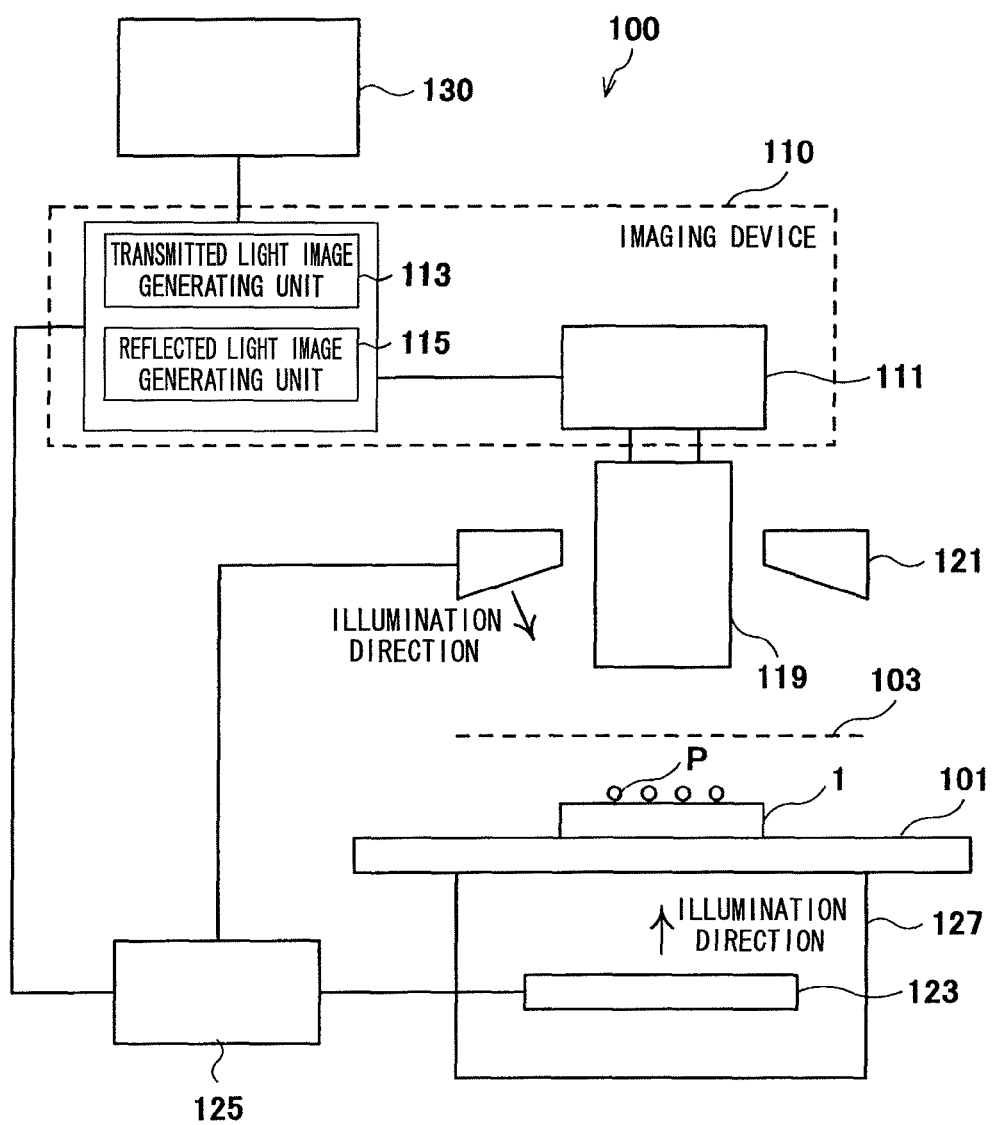
FIG. 2 is an explanatory diagram that schematically illustrates the configuration of a particle measuring device according to a first embodiment of the present invention.

As above, while the overview and the superiority of the present invention have been described, subsequently, a particle measuring device according to a first embodiment of the present invention will be described in detail with reference to FIG. 2. FIG. 2 is an explanatory diagram that schematically illustrates the configuration of the particle measuring device according to the embodiment.

As illustrated in FIG. 2, the particle measuring device 100 according to the embodiment is a device that measures the position, the size, the brightness, and the like of an opaque fine particle and mainly includes a stage 101, an imaging device 110, a reflected light illuminating device 121, a transmitted light illuminating device 123, an illumination control device 125, and an image processing device 130.

<Stage 101>

The stage 101 is a transparent flat plate, on which a transparent substrate 1 onto which opaque fine particles P that are measurement targets are sprayed, is placed. Although the material of this stage 101 is not particularly limited, as long as it has rigidity of a certain level, for example, a float glass plate, a transparent acrylic plate, or the like can be used as the material. In addition, from the viewpoint of maintaining the rigidity of the stage 101 and not degrading the transparency, the thickness of the stage 101 is preferably in the range of about 1 mm to 100 mm.

<Imaging Device 110>

The imaging device 110 is disposed on the upper side of the stage 101, in other words, the side of a face (a placement face, hereinafter, also referred to as a "substrate placement face") of the stage 101 on which the transparent substrate 1 formed from slide glass or the like is placed and images fine particles P. This imaging device 110, for example, receives transmitted light emitted from a fine particle P at the time of emitting illumination from a transmitted light illuminating device 123 toward the fine particle P and reflected light reflected from a fine particle P at the time of emitting illumination from a reflected light illuminating device 121 toward the fine particle P and generates captured images (a transmitted light image and a reflected light image).

As such an imaging device 110, a digital camera of a charge coupled device (CCD) type or a complementary metal oxide semiconductor (CMOS) type can be used. Since the brightness levels (representative brightness levels) of each fine particle P are averaged within the size of individual CCD elements corresponding to each particle image, it is preferable that the number of pixels of the camera is large in terms of the measurement accuracy of the brightness of the fine particle P. More specifically, it is preferable to use the imaging device 110 that includes pixels of a density capable of imaging a fine particle P, which is a measurement target, using at least nine or more pixels (monochrome camera). From the viewpoint of accurately recording the brightness of a fine particle P, it is preferable that the camera is a monochrome camera. In a case where a single-plate type color camera (generally, mutually-different color filters are applied to CCD elements that are adjacent to each other) is used as the imaging device 110, a process for the measurement accuracy such as a process of using brightness values (in the case of a Bayer array) that are interpolated using brightness levels of at least four pixels are used as brightness to be measured is necessary, and accordingly, it is preferable to use the imaging device 110 having a density of pixels that can image a target fine particle P using at least 36 pixels or more. In addition, in order to secure a pixel density that is necessary for imaging a particle that is a target, the particle may be imaged through a lens 119 such as a microscope in an enlarged scale as necessary.

In addition, the imaging device 110 according to the embodiment includes an imaging element 111, a transmitted light image generating unit 113, and a reflected light image generating unit 115 as an internal configuration. The imaging element 111, for example, is a CCD or a CMOS described above. The transmitted light image generating unit 113 generates a transmitted light image that is acquired by imaging a fine particle P in a state controlled by the illumination control device 125 such that the luminance (device light emitting face luminance) of the transmitted light illuminating device 123 is predetermined luminance other than zero, and the luminance (device light emitting face luminance) of the reflected light illuminating device 121 is zero. In addition, the reflected light image generating unit 115 generates a reflected light image that is acquired by imaging a fine particle P in a state controlled by the illumination control device 125 such that the luminance of the transmitted light illuminating device 123 is predetermined luminance set in accordance with one condition or two or more conditions, and the luminance of the reflected light illuminating device 121 is predetermined luminance other than zero.

When the reflected light illuminating device 121 and the transmitted light illuminating device 123 are controlled by the illumination control device 125 as above, the transmitted light image generating unit 113 and the reflected light image generating unit 115 may transmits signals indicating desired set luminance levels of the transmitted light illuminating device 123 and the reflected light illuminating device 121, any other external device may transmits a signal indicating set luminance levels to the illumination control device 125, or signals indicating set luminance levels may be transmitted from an input device by a user operating the input device disposed in the illumination device 125.

Particularly, in this embodiment, the reflected light image generating unit 115 generates a reflected light image in a state in which the luminance of the transmitted light illuminating device 123 is set by the illumination control device 125 such that the brightness of the background of the reflected light particle in the reflected light image is higher than a brightness threshold value that is used for identifying the brightness of the particle.

The "brightness threshold value used for identifying the level of the brightness of a particle", for example, can be calculated as below. First, a calibration sample particle is prepared, which has boundary reflectance for a fine particle P that is a measurement target of which the brightness is desired to be identified as "bright (high brightness)" or "dark (low brightness)". Next, in a condition in which the reflected light illuminating device 121 has predetermined luminance, and the transmitted light illuminating device 123 is turned off (switched off), image processing is performed for an image that is acquired by imaging the calibration sample particle and calculates average brightness of all the pixels that are included in a pixel region corresponding to the calibration sample particle. The average brightness of the calibration sample particle calculated as above can be used as the "brightness threshold value used for identifying the level of the brightness of a particle".

The above-described boundary reflectance at the time of calculating the brightness threshold value, which is used for identifying the level of the brightness of a particle, is a boundary value of reflectance that is used for determining a particle having reflectance higher than this reflectance (boundary reflectance) is determined as being bright colored and a particle having reflectance lower than this reflectance as being dark colored, in other words, reflectance that is a boundary at the time of determining the brightness of a particle to be bright colored or dark colored. Here, the reflectance of the particle surface is a property that is unique to a particle that is not based on the illumination condition. Accordingly, the boundary reflectance can be appropriately determined in accordance with the type of a fine particle P that is included in the sample (fine particle group) that is a measurement target.

In addition, in a case where a particle having the boundary reflectance cannot be prepared, it may be configured such that a bright-color calibration particle that is a reference used for determining a bright color particle and a dark-color calibration particle that is a reference used for determining a dark color particle are prepared, image processing is performed for images that are acquired by imaging the particles, average brightness of the bright-color calibration particle and the average brightness of the dark-color calibration particle are acquired, and an average value of the average brightness of the acquired two values is used as the brightness threshold value that is used for determining the level of the brightness of a particle.

Furthermore, instead of preparing the calibration sample particle or the bright-color calibration particle and the dark-color calibration particle described above, it may be configured such that image processing is performed for an image that is acquired by imaging a gray color sample sheet having the boundary reflectance, average brightness of all the pixels included in the captured image is calculated, and the calculated average brightness is used as the brightness threshold value that is used for determining the level of the brightness of a particle.

In addition, the imaging device 110 transmits the transmitted light image and the reflected light image that have been generated to the image processing device 130. Furthermore, in a case where the particle measuring device 100 includes a predetermined storage device (not illustrated in the figure), the imaging device 110 may record the data of the transmitted light image and the reflected light image, which have been generated, in the storage device.

<Reflected Light Illuminating Device 121>

The reflected light illuminating device 121 is disposed on the upper side of the stage 101, in other words, on the side of a substrate placement face of the stage 101 with respect to the stage 101 and emits light having predetermined luminance toward the stage 101. As the reflected light illuminating device 121, for example, a ring-shaped illuminance device (halogen lamp) for a microscope, an LED illumination device, a fluorescent tube, or the like, which is available in the market, can be used. In addition, illumination may be appropriately performed from the reflected light illuminating device 121 by transmitting a diffusion plate, a polarizing filter (both are not illustrated in the figure), and the like. Furthermore, it may be configured such that planar illumination may be performed by arranging a plurality of the reflected light illuminating devices 121 and arranging the reflected light illuminating devices 121 on a plane. Such planar illumination is effective so as to avoid degradation of the image quality due to specularly reflected light (a highlight or the like). In addition, in the particle measuring device 100 according to the embodiment, in order to measure the brightness of a particle image, it is preferable that the illumination condition at the time of imaging a fine particle P is set such that constant illumination is constantly formed on the imaging face.

<Transmitted Light Illuminating Device 123>

The transmitted light illuminating device 123 is disposed on a lower side of the stage 101, in other words, on a side opposite to the substrate placement of the stage 101 with respect to the stage 101 and emits light having predetermined luminance toward the stage 101. As the reflected light illuminating device 121, for example, a halogen lamp (a single-lamp type or a multiple-lamp type), an LED illumination device, a fluorescent tube, or the like, which is available in the market, can be used. In addition, illumination may be appropriately performed from the transmitted light illuminating device 123 by transmitting a diffusion plate, a polarizing filter 103, and the like. Furthermore, it may be configured such that planar illumination may be performed by arranging a plurality of the transmitted light illuminating devices 123 and arranging the transmitted light illuminating devices 123 on a plane. Such planar illumination is effective so as to avoid degradation of the image quality due to specularly reflected light (a highlight or the like). In addition, in the particle measuring device 100 according to the embodiment, in order to measure the brightness of a particle image, it is preferable that the illumination condition at the time of imaging a fine particle P is set such that constant illumination is constantly formed on the imaging face.

<Illumination Control Device 125>

The illumination control device 125 controls the reflected light illuminating device 121 and the transmitted light illuminating device 123 such that the luminance of the reflected light illuminating device 121 and the luminance of the transmitted light illuminating device 123 are independently set. As this illumination control device 125, a device that is available in the market can be used. More specifically, as the illumination control device 125, for example, a device that can independently turn on/off the reflected light illuminating device 121 and the transmitted light illuminating device 123 in accordance with an external signal or a device that can further independently change the luminance of the reflected light illuminating device 121 and the luminance of the transmitted light illuminating device 123 can be used.

More specifically, in a case where imaging is performed using transmitted light that is acquired by allowing light emitted from the transmitted light illuminating device 123 to be transmitted through a fine particle P, the illumination control device 125 performs control such that the luminance of the transmitted light illuminating device 123 is predetermined luminance other than zero, and the luminance of the reflected light illuminating device 121 is zero. In addition, in a case where imaging is performed by using reflected light that is acquired by along light emitted from the reflected light illuminating device 121 to be reflected on the surface of a fine particle, the illumination control device 125 performs control such that the luminance of the transmitted light illuminating device 123 is predetermined luminance that is set in accordance with one, two or more conditions, and the luminance of the reflected light illuminating device 121 is predetermined luminance other than zero.

<Image Processing Device 130>

By comparing the position and the size of one or two or more transmitted light particles that are identified as candidates for capturing an image of a fine particle P within a transmitted light image that is generated by the transmitted light image generating unit 113 and the position and the size of one or two or more reflected light particles identified as candidates for capturing an image of a fine particle P within the reflected light image that is generated by the reflected light image generating unit 115 with each other, the image processing device 130 associates a transmitted light particle and a reflected light particle of which a difference in the position and the size is within a predetermined range with each other, calculates the position and the size of the transmitted light particle as the position and the size of the fine particle P, based on the result of the association, and calculates representative brightness of the reflected light particle or the transmitted light particle as the brightness of the fine particle P.

Here, a method of identifying a particle according to image processing of a captured image will be described. In a transmitted light image, since the background constantly has high brightness, in a case where an opaque fine particle P that is a measurement target is present, an area having low brightness within the transmitted light image is recognized as a particle image (transmitted light particle). In addition, in a reflected light image, while the background differs based on the luminance of the transmitted light illuminating device 123, an opaque fine particle P as a measurement target becomes a high-brightness area in the case of a particle having a bright color (high brightness) and becomes a low-brightness area in the case of a dark color (low brightness), regardless of the brightness of the background. Accordingly, in the reflected light image, the fine particle P is recognized as a particle image (reflected light image) in a case where there is a difference to some degree in brightness from the brightness of the background but is not recognized as a particle image in the case of brightness that is in the same level as that of the brightness of the background. For example, in a case where the background of the reflected light image has high brightness, while a fine particle P having high brightness is not recognized as a particle image, a fine particle P having low brightness is recognized as a dark-color particle image.

Figure 3:
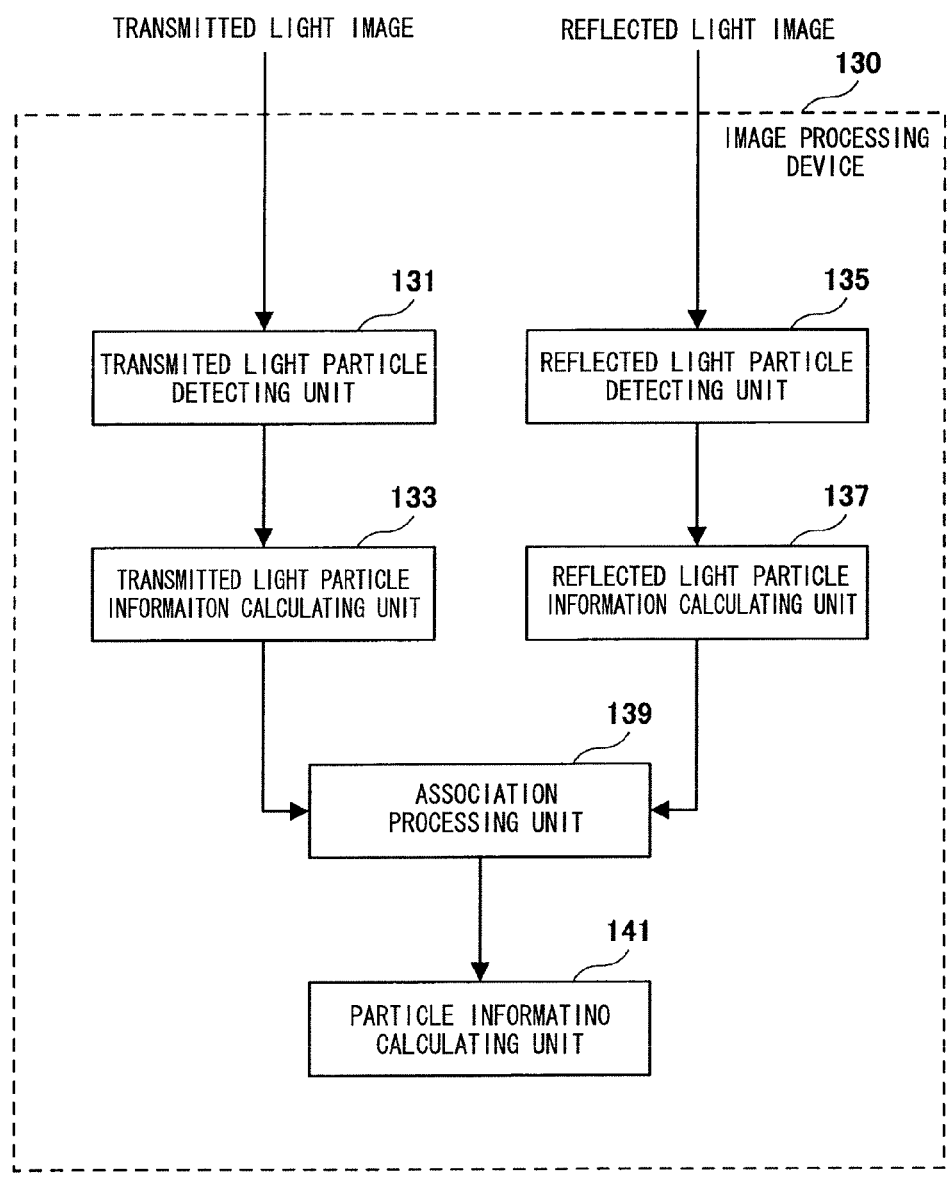
FIG. 3 is a block diagram that illustrates the functional configuration of an image processing device according to the embodiment.

Next, a detailed configuration of the image processing device 130 according to the embodiment will be described with reference to FIG. 3. FIG. 3 is a block diagram that illustrates the functional configuration of the image processing device 130 according to the embodiment.

As illustrated in FIG. 3, the image processing device 130 mainly includes a transmitted light particle detecting unit 131, a transmitted light particle information calculating unit 133, a reflected light particle detecting unit 135, reflected light particle information calculating unit 137, an association processing unit 139, and a particle information calculating unit 141.

The transmitted light particle detecting unit 131 specifies a pixel area in which pixels having low brightness are aggregated in pixel coordinates of a transmitted light binarized image as an area in which a transmitted light particle is present based on the brightness distribution (the binarized image is configured by pixels located on the high brightness side and pixels located on the low brightness side) of the transmitted light binarized image that is acquired by binarizing the transmitted light image using a predetermined brightness threshold value and detects the position coordinates of the pixel within the area in which the transmitted light particle is present. The transmitted light particle detecting unit 131 transmits information relating to the detected position coordinates of the pixel within the area in which the transmitted light particle is present to the transmitted light particle information calculating unit 133. In addition, an example of setting of the predetermined brightness threshold value that is used when the transmitted light binarized image is acquired will be described later.

The transmitted light particle information calculating unit 133 calculates at least the position and the size of the transmitted light particle based on the detection result acquired by the transmitted light particle detecting unit 131, in other words, information relating to the position coordinates of the pixel within the area in which the transmitted light particle is present that has been transmitted from the transmitted light particle detecting unit 131. Here, the position of the transmitted light particle according to the embodiment, for example, can be represented by using position coordinates of the pixel that is present at the center position or the like in a case where a transmitted light particle recognized within the transmitted light binarized image is assumed as a circle. In addition, the size of the transmitted light particle according to the embodiment, for example, can be represented by using the area of a circle or the like in a case where the transmitted light particle recognized within the transmitted light binarized image is assumed as a circle. In addition, the transmitted light particle information calculating unit 133 may calculate a diameter (equivalent circle diameter) as the size of the transmitted light particle in a case where the transmitted light particle is assumed as a circuit in addition to the area of the transmitted light particle or instead of the area of the transmitted light particle.

In addition, the transmitted light particle information calculating unit 133 transmits information relating to the center position, the area, the diameter, and the like of the transmitted light particle, which have been calculated, to the association processing unit 139 and the particle information calculating unit 141. Furthermore, the transmitted light particle information calculating unit 133 may record the information relating to the center position, the area, the diameter, and the like of the transmitted light particle, which have been calculated, in a storage device (not illustrated in the figure) of the particle measuring device 100.

The reflected light particle detecting unit 135 specifies a pixel area in which pixels having brightness that is different from that of peripheral pixels by a predetermined value or more are aggregated out of the coordinates of the pixels of the reflected light image or the reflected light binarized image based on the brightness density of the reflected light image that is captured by the imaging device 110 or the reflected light binarized image acquired by binarizing the reflected light image and detects the position coordinates of the pixels within the area in which the reflected light particle is present.

Here, in the embodiment, the reflected light particle detecting unit 135 may specify a pixel area in which low-brightness pixels are aggregated out of the coordinates of pixels of the reflected light image as an area in which a reflective light particle is present based on the brightness distribution of an image that is acquired by binarizing the reflected light image using the above-described "brightness threshold value used for identifying the level of the brightness of a particle" and detect the position coordinates of the pixel within the area in which the reflective light particle is present. In addition, in the reflected light image captured by the imaging device 110, in a case where there is a large difference between the brightness of the pixel area that can be recognized as a particle and the brightness of the pixel area (background) that is located on the periphery of the pixel area, and it is easy to directly recognize a particle from the reflected light image, the reflected light particle detecting unit 135 may specify an area in which a reflected light particle is present directly from the reflected light image without binarizing the reflected light image and detect the position coordinates of the pixels within the area in which the reflected light particle is present.

In addition, the reflected light particle detecting unit 135 transmits the information relating to the detected coordinates of the position of the pixel within the area in which the reflected light particle is present to the reflected light particle information calculating unit 137.

The reflected light particle information calculating unit 137 calculates at least the position and the size of the reflected light particle based on the detection result acquired by the reflected light particle detecting unit 135, in other words, information relating to the position coordinates of the pixel within the area in which the reflected light particle is present that has been transmitted from the reflected light particle detecting unit 135. Here, the position of the reflected light particle according to the embodiment, for example, can be represented by using position coordinates of the pixel that is present at the center position or the like in a case where a reflected light particle recognized within the reflected light image or the reflected light binarized image is assumed as a circle. In addition, the size of the reflected light particle according to the embodiment, for example, can be represented by using the area or a circle or the like in a case where the reflected light particle recognized within the reflected light image or the reflected light binarized image is assumed as a circle. In addition, the reflected light particle information calculating unit 137 may calculate a diameter (equivalent circle diameter) as the size of the reflected light particle in a case where the reflected light particle is assumed as a circuit in addition to the area of the reflected light particle or instead of the area of the reflected light particle.

In addition, the reflected light particle information calculating unit 137 transmits information relating to the center position, the area, the diameter, and the like of the reflected light particle, which have been calculated, to the association processing unit 139 and the particle information calculating unit 141. Furthermore, the reflected light particle information calculating unit 137 may record the information relating to the center position, the area, the diameter, and the like of the reflected light particle, which have been calculated, in a storage device (not illustrated in the figure) of the particle measuring device 100.

The association processing unit 139, based on the calculation results of the transmitted light particle information calculating unit 133 and the reflected light particle information calculating unit 137, in other words, the information relating to the center position, the area, the diameter, and the like of the transmitted light particle transmitted from the transmitted light particle information calculating unit 133 and the information relating to the center position, the area, the diameter, and the like of the reflected light particle transmitted from the reflected light particle information calculating unit 137, compares the position and the size of the reflected light particle and the positions and the sizes of all the transmitted light particles with each other and associates a transmitted light particle and a reflected light particle having differences in the position and the size within predetermined ranges with each other. In addition, the association processing unit 139 excludes a reflected light particle that is not associated with any transmitted light particle from candidates for the captured image of the fine particle P.

Here, a difference between the positions of the reflected light particle and the positions of the transmitted light particle, for example, can be represented as a distance between the center position of the reflected light particle and the center position of the transmitted light particle. In a case where this distance is short (within a predetermined range), there is a possibility that the reflected light particle and the transmitted light particle are captured images of the same fine particle P. In addition, a difference between the sizes of the reflected light particle and the transmitted light particle, for example, can be represented as a difference between the area of the reflected light particle and the area of the transmitted light particle or a difference between an equivalent circle diameter of the reflected light particle and an equivalent circle diameter of the transmitted light particle. In a case where the difference between the areas or the diameters is small (within the predetermined range), there is a possibility that the reflected light image and the transmitted light particle are captured images of the same fine particle P. In the embodiment, in a case where both the difference in the positions of the reflected light particle and the transmitted light particle and the difference between the sizes of the reflected light particle and the transmitted light particle are within predetermined ranges, it is determined that there is a high possibility that the reflected light image and the transmitted light image are captured images of the same fine particle P, the reflected light particle and the transmitted light particle are associated with each other.

In addition, the association processing unit 139 transmits the result of the association between the transmitted light particle and the reflected light particle, for example, information relating to (1) a list of each combination of a transmitted light particle that are associated with each other (2) a list of transmitted light particles that are not associated with any reflected light particle, and (3) a list of reflected light particles that are not associated with any transmitted light particle to the particle information calculating unit 141. In addition, the association processing unit 139 may record the information relating to the above-described lists (1) to (3) in a storage device (not illustrated in the figure) of the particle measuring device 100. However, since the reflected light particles included in list (3) are excluded from the candidates for the captured image of a fine particle P, the association processing unit 139 does not necessarily need to transmit the information relating to list (3) to the particle information calculating unit 141. A method for association between the transmitted light particle and the reflected light particle will be described in detail later.

Based on the result of the association between the transmitted light particles and the reflected light particles that is transmitted from the association processing unit 139, the particle information calculating unit 141 calculates the position and the size of the transmitted light particle as the position and the size of a fine particle P, calculates the representative brightness of the reflected light particle that is associated with the transmitted light particle as the brightness of a fine particle, and calculates the brightness of a transmitted light particle that is not associated with any reflected light particle as predetermined brightness. Here, the predetermined brightness may be appropriately determined within a brightness range located on a side opposite to the representative brightness of the reflected light particle with the brightness threshold value interposed therebetween. For example, in a case where the brightness threshold value is 100, and the representative brightness of the reflected light particle is 120, the predetermined brightness can be set to 80.

Particularly, in the embodiment, the particle information calculating unit 141 identifies a fine particle P corresponding to the transmitted light particle that is associated with the reflected light particle as a dark-color particle having brightness that is lower than the brightness threshold value used for identifying the level of the brightness of a particle and a fine particle P corresponding to a transmitted light particle that is not associated with any reflected light particle as a bright-color particle having brightness higher than the brightness threshold value that is used for identifying the level of the brightness of a particle.

<Light Shielding Plate 127>

The particle measuring device 100 according to the embodiment may further include a light shielding plate 127 as necessary. The light shielding plate 127, for example, may be arranged so as to be in contact with the lower face (the side opposite to the substrate placement) of the stage 101 in the upper end and to cover the periphery of the transmitted light illuminating device 123. The lower end of the light shielding plate 127 may be open or closed. The role of this light shielding plate 127 is to prevent the input of light from the periphery of the transmitted light illuminating device 123 when the illumination according to the transmitted light illuminating device 123 is turned off, thereby forming the rear face of the stage 101 to be dark colored. Accordingly, in a case where an all-operations of the measurement of the position, the size, the brightness, and the like of a fine particle P is performed inside a dark room, the light shielding plate 127 does not need to be disposed.

As above, the process of the image processing device 130 according to the embodiment has been described. Each processing unit described above may be realized by an arithmetic processing device of the image processing device 130 executing various programs, or may be realized by hardware that is specialized for the function of each processing unit described above. This point is similar to the other embodiments described later.

(Particle Measuring Method)

Figure 4:
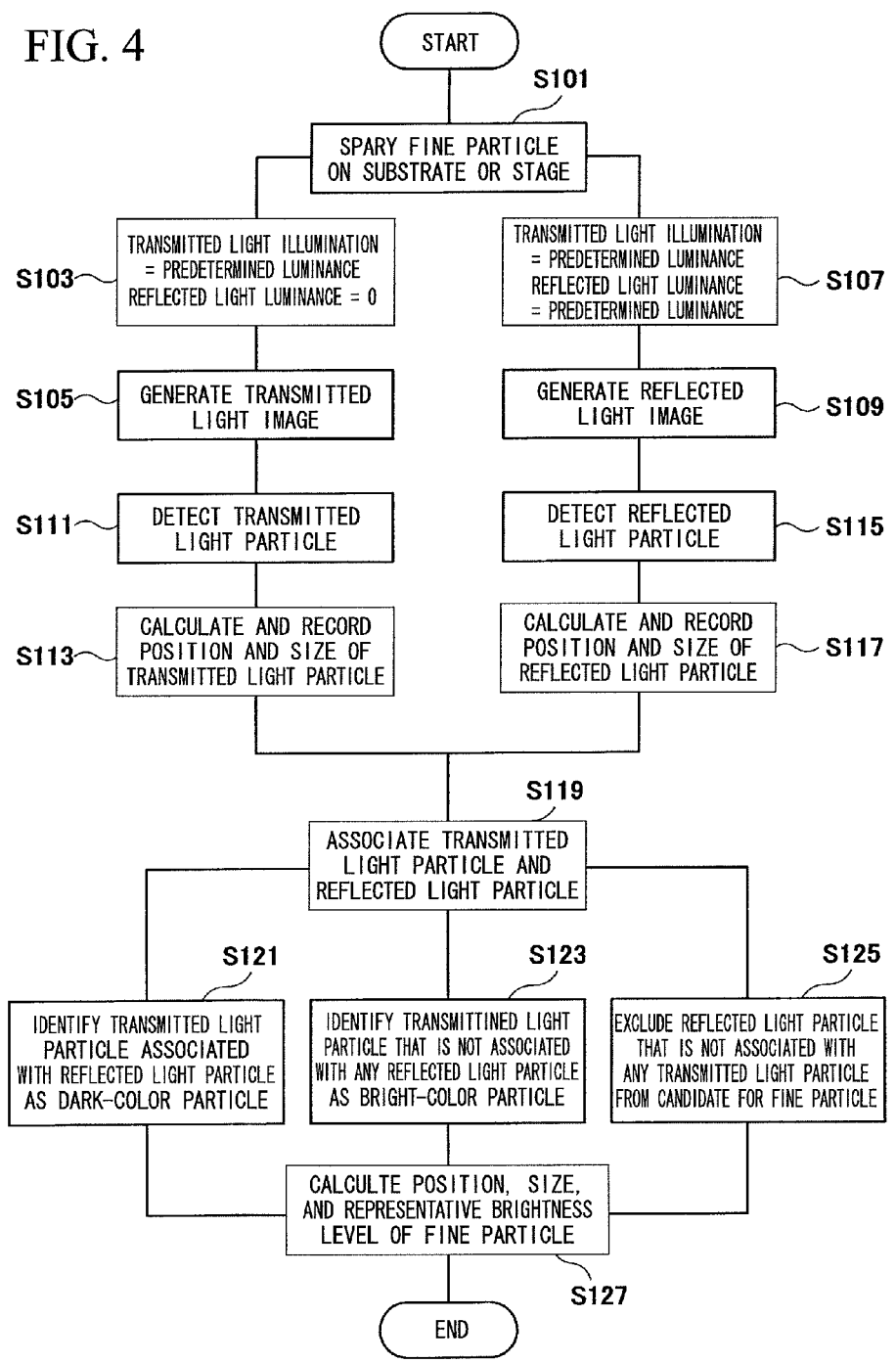
FIG. 4 is a flowchart that illustrates the processing flow in a particle measuring method of measuring according to the embodiment.

As above, while the particle measuring device 100 according to the embodiment has been described in detail, subsequently, a particle measuring method according to the embodiment using the above-described measuring device 100 will be described in detail with reference to FIG. 4. FIG. 4 is a flowchart that illustrates the processing flow in the particle measuring method according to the embodiment.

The particle measuring method according to the embodiment is a method of measuring the position, the size, and the brightness of a fine particle sprayed on a flat substrate 1 or a state 101, using the above-described particle measuring device 100 and, as described below, mainly includes an analysis sample processing process, a transmitted light image generating process, a reflected light image generating process, and an image processing process.

<Analysis Sample Processing Process>

First, an analysis (particle measuring) sample is processed. More particularly, particles P (for example, falling dust particles collected in a specific place within an iron manufacturing plant) that are samples are sprayed on the substrate 1, and the substrate 1 is placed on the stage 101, or the fine particles P are directly sprayed on the stage 101 (S101). At this time, the spraying amount is adjusted such that particles are not brought into contact with each other as possibly as can be, and the sprayed particles P are made even using a spatula as appropriate. The number of the fine particles P sprayed on the substrate 1 is not particularly limited (in a case where the collected falling dust are used, all the dusts do not need to be processed as analysis samples), and, in order to evaluate the effect of variations in the test material, it is preferable that at least 100 or more fine particles P be shared as analysis samples.

In addition, in a case where falling dusts originated from an iron manufacturing plant are used as samples, since the falling dusts, generally, are rough particles having φ10 μm or more, and accordingly, in order to spray the falling dust particles, free fall of falling dust particles in the air can be used. In particular, for example, by spooning the collected falling dusts and allowing them to fall on the substrate, the falling dust particles can be sprayed on the substrate.

By using the analysis samples prepared as above, the transmitted light image generating process, the reflected light image generating process, and the image processing process described below are performed.

<Transmitted Light Image Generating Process>

In the transmitted light image generating process, as illustrated in FIG. 4, the illumination control device 125 sets such that the luminance of the transmitted light illuminating device 123 is predetermined luminance other than zero, and the luminance of the reflected light illuminating device 121 is zero (the illumination according to the reflected light illuminating device 121 is turned off) (S103). Then, in the state in which the illumination is set as described above, fine particles P are imaged by the imaging device 110, and the transmitted light image generating unit 113 of the imaging device 110 generates a transmitted light image (S105). In addition, the transmitted image generating unit 113 transmits the generated transmitted light image to the image processing device 130.

<Reflected Light Image Generating Process>

In the reflected light image generating process, as illustrated in FIG. 4, the illumination control device 125 sets such that the luminance of the transmitted light illuminating device 123 is predetermined luminance that is set in accordance with one, two or more conditions, and the luminance of the reflected light illuminating device 121 is predetermined luminance other than zero (S107). Then, in the state in which the illumination is set as described above, fine particles P are imaged by the imaging device 110, and the reflected light image generating unit 115 of the imaging device 110 generates a reflected light image (S109). In addition, the reflected image generating unit 115 transmits the generated reflected light image to the image processing device 130.

Here, in the reflected light image generating process according to the embodiment, the illumination control device 125 sets the luminance of the illumination emitted from the transmitted light illuminating device 123 to such luminance (predetermined luminance) that the brightness of the background of the reflected light particle on the reflected light image is higher than the brightness threshold value that is used for determining the level of the brightness of a particle. The "brightness threshold value for identifying the level of the brightness of a particle" of this case, for example, can be calculated as below. First, a calibration sample having the boundary reflectance for the fine particle P, which is a measurement target, of which the brightness is identified as "bright (high brightness)" or "dark (low brightness")" is prepared. Next, image processing is performed for an image that is acquired by imaging the calibration sample particle in the conditions in which the luminance of the reflected light illuminating device 121 is predetermined luminance, and the transmitted light illuminating device 123 is turned off (extinguished), and average brightness of all the pixels that are included in a pixel area corresponding to the calibration sample particle is calculated. The average brightness of the calibration sample particle, which is calculated as above, can be used as the "threshold value used for identifying the level of the brightness of a particle".

The above-described boundary reflectance, which is used for identifying the level of the brightness of a particle, is a boundary value of reflectance that is used for determining a particle having reflectance higher than this reflectance (boundary reflectance) is determined as being bright colored and a particle having reflectance lower than this reflectance as being dark colored, in other words, reflectance that is a boundary at the time of determining the brightness of a particle to be bright colored or dark colored. Here, the reflectance of the particle surface is a property that is unique to a particle that is not based on the illumination condition. Accordingly, the boundary reflectance can be appropriately determined in accordance with the type of a fine particle P that is included in the sample (fine particle group) that is a measurement target.

In addition, in a case where a particle having the boundary reflectance cannot be prepared, it may be configured such that a bright-color calibration particle that is a reference used for determining a bright color particle and a dark-color calibration particle that is a reference used for determining a dark color particle are prepared, image processing is performed for images that are acquired by imaging the particles, average brightness of the bright-color calibration particle and the average brightness of the dark-color calibration particle are acquired, and an average value of the average brightness of the acquired two values is used as the brightness threshold value that is used for determining the level of the brightness of a particle.

Furthermore, instead of preparing the calibration sample particle or the bright-color calibration particle and the dark-color calibration particle described above, it may be configured such that image processing is performed for an image that is acquired by imaging a gray color sample sheet having the boundary reflectance, average brightness of all the pixels included in the captured image is calculated, and the calculated average brightness is used as the brightness threshold value that is used for determining the level of the brightness of a particle.

<Image Processing Process>

Each process of the image processing process described below is performed by each processing unit of the image processing device 130 illustrated in FIG. 3. This point is similar to the other embodiments to be described later.

In the image processing process, first, within the transmitted light image generated by the transmitted light image generating unit 113, one, two or more transmitted light particles which is identified as candidates for a captured image of a fine particle P that is a measurement target (not actual particles but pixel areas identified as images within the captured image) are detected (S111).

Figure 5:
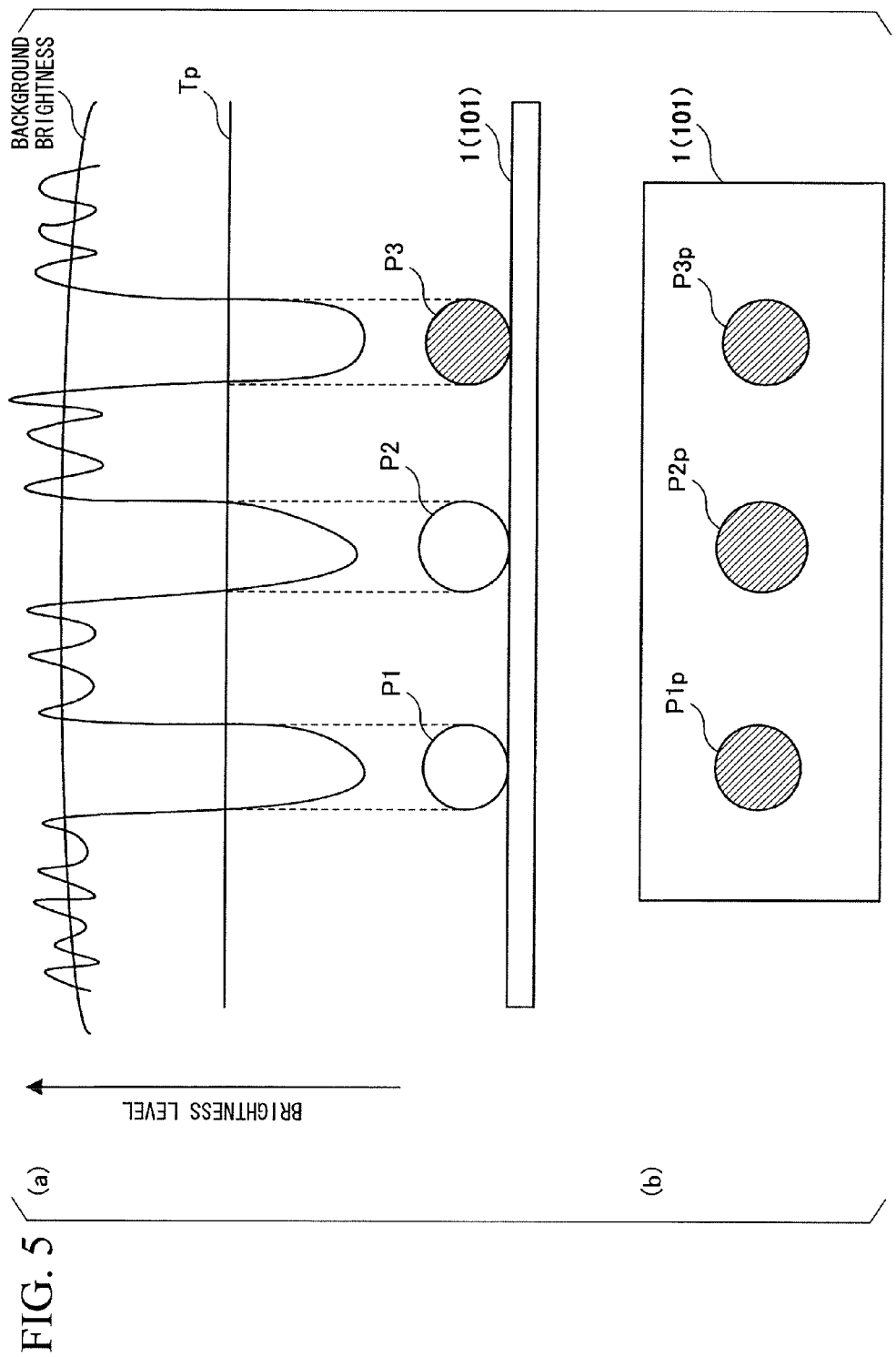
FIG. 5 is an explanatory diagram that illustrates an example of an image processing method using a transmitted light image according to the embodiment.

Here, a method of detecting a transmitted light particle will be described with reference to FIG. 5. FIG. 5 is an explanatory diagram that illustrates an example of an image processing method using a transmitted light image according to the embodiment. FIG. 5(a) illustrates side views of fine particles P1 to P3 that are aligned in a line on a substrate 1 and illustrates a brightness distribution on a straight line on which the centers of the fine particles P1 to P3 are aligned, and FIG. 5(b) illustrates binarized captured images of which the positions are aligned with (a). To the drawings presented below, the same definitions are applied.

As illustrated in FIG. 5(a), the brightness of each pixel in the transmitted light image is lower in places in which the fine particles P1, P2, and P3 are present than in the brightness of the background. The reason for this is that, while the fine particles P1, P2, and P3, which are measurement targets, are opaque particles in the embodiment, light emitted from the lower side of such fine particles is not transmitted in places in which the fine particles P1, P2, and P3 are present, and accordingly dark colors (areas having low brightness) are recognized on the transmitted light image, the substrate 1 or the stage 101 on which the fine particles P1, P2, and P3 are sprayed are transparent, light emitted from the lower side is transmitted, and a bright color (an area having high brightness) is recognized on the transmitted light image.

When a transmitted light particle is detected, first, the transmitted light image is binarized using a predetermined brightness threshold value Tp, whereby a transmitted light binarized image is generated. As the predetermined brightness threshold value Tp at this time, a brightness threshold value lower than a brightness threshold value corresponding to the brightness of light that is transmitted through a transparent particle at the time of illumination emitted by the transmitted light illuminating device 123 is used. As the "brightness threshold value corresponding to the brightness of light that is transmitted through a transparent particle at the time of illumination emitted by the transmitted light illuminating device 123" (hereinafter, referred to as a "brightness threshold value Tp0"), for example, a lowest brightness value among representative brightness values of individual particles that are acquired by processing particle images that are acquired by capturing transparent or semi-transparent particles (glass fine particles or the like) in advance may be used. The brightness threshold value Tp0 determined as above has brightness that is higher than the representative brightness of a pixel area that is identified as a particle on a transmitted light image of an opaque particle.

Here, the "representative brightness" is brightness that represents a whole pixel area that is identified as a particle, and, as the "representative brightness", for example, an average value of the brightness of each pixel within the pixel area, a median value of the brightness of each pixel, or the like can be used. In addition, in order to eliminate abnormal values of the brightness of pixels that are present within the pixel area, an average value of the brightness levels of the pixels from which a pixel having a maximum brightness level and a pixel having a lowest brightness level are eliminated may be used as the "representative brightness". Furthermore, in a peripheral edge portion of a pixel area that is identified as a particle, generally, since the brightness may drastically change due to a highlight or the like, such pixels are eliminated, and in order to eliminate the influence of the highlight or the like, an average value of the brightness levels of the pixels from which pixels located in the peripheral edge portion are excluded may be used as the "representative brightness".

In addition, the method of setting the brightness threshold value Tp is not limited to the above-described method, and any method may be used as long as the method can be used for recognizing an opaque particle within a captured image using transmitted light.

Furthermore, since it is practically difficult to acquire completely uniform illuminance for the entire area within the visual field of the imaging device 110, the variation of the illuminance within an image may be corrected by adding or subtracting a correction value, which is a function of a two-dimensional position of a pixel, to or from recorded brightness of the pixel before the binarization process. As a method of calculating the correction value in such a case, for example, a gray test piece of which the scattered light reflectance value is known in advance is photographed by the imaging device 110 used in the embodiment, and a value acquired by decreasing an average brightness value of all the pixels of the recorded image by the brightness of each pixel can be used as a brightness correction value of the pixel. In a case where the correction value is sufficiently small with respect to the dynamic range of the pixel, an error according to this correction method is small. In addition, it is preferable that the illuminance on the imaging face is configured to be uniform as possibly as can so as to decrease the correction value.

The transmitted light binarized image acquired as above, as illustrated in FIG. 5(b), is formed by pixels having high brightness levels (illustrated as a white area) and pixels having low brightness levels (illustrated as areas of slanting lines), and, in the transmitted light binarized image, an area in which a particle is present is recognized as a pixel having a low brightness level. Accordingly, based on the connection relation of the binarized brightness levels of pixels that are adjacent to each other in the transmitted light binarized image, areas, in which pixels (in the embodiment, pixels having low brightness levels) having the same binarized brightness level are continuous, and that are independent from the other areas (in the embodiment, areas in which pixels having high brightness levels are present) are specified as areas in which the fine particles P1, P2, and P3 are present, in other words, areas in which the transmitted light particles P1p, P2p, and P3p are present. In addition, the position coordinates of the pixels within the specified area in which the transmitted light particle is present are detected, the positions (for example, the center positions) and the sizes (for example, the areas or the diameters) of the transmitted light particles P1$p$, P2$p$, and P3$p$ are calculated based on the position coordinates, and the positions and the sizes are recorded in a storage device (not illustrated in the figure) disposed in the image processing device 130 or the like (S113).

Next, in the reflected light image that is generated by the reflected light image generating unit 115, one or two or more reflected light particles which is identified as candidates for a captured image of a fine particle P that is the measurement target (not actual particles but pixel areas identified as images of particles within the captured image) are detected (S115).

Figure 6:
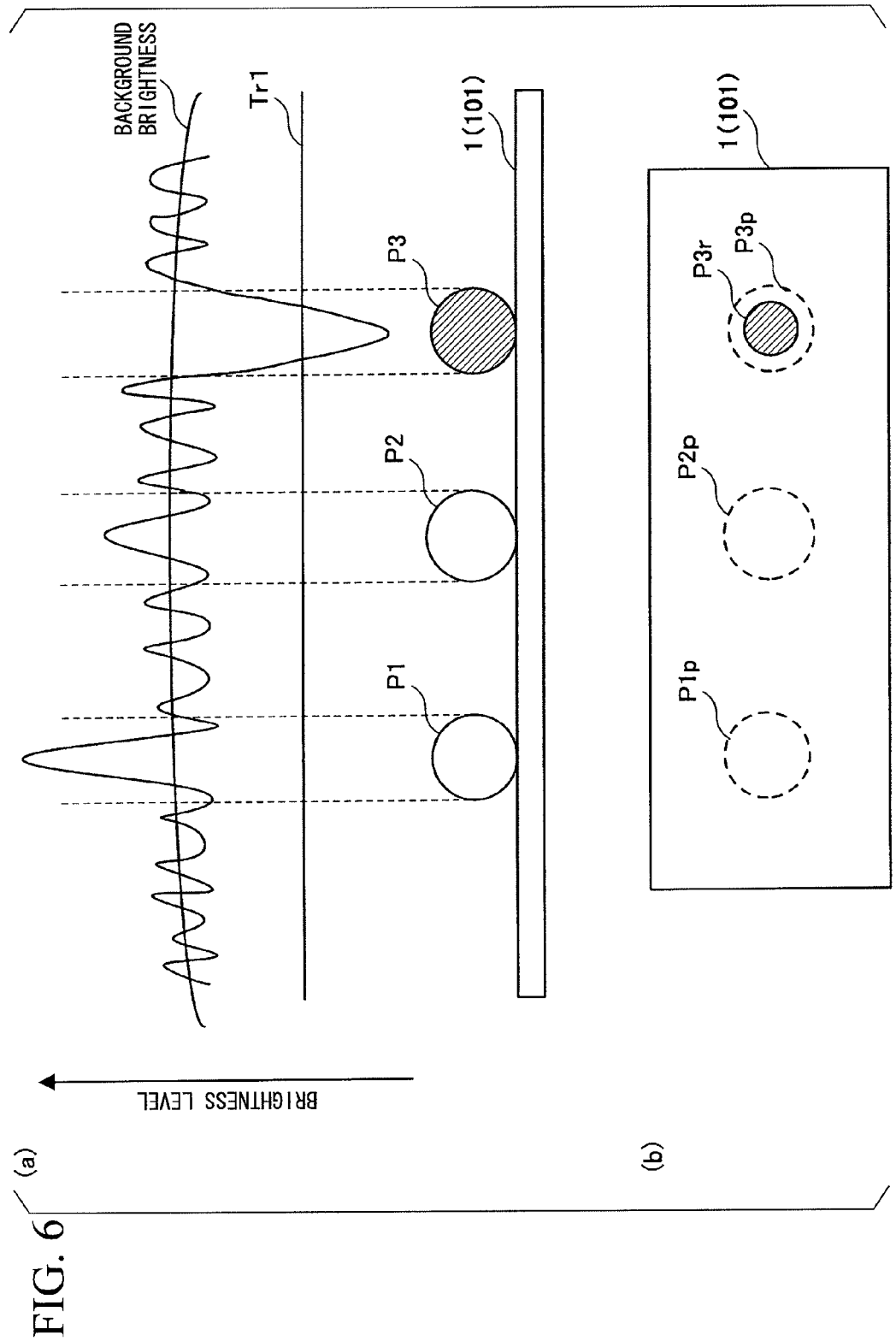
FIG. 6 is an explanatory diagram that illustrates an example of an image processing method using a reflected light image according to the embodiment.
Figure 7:
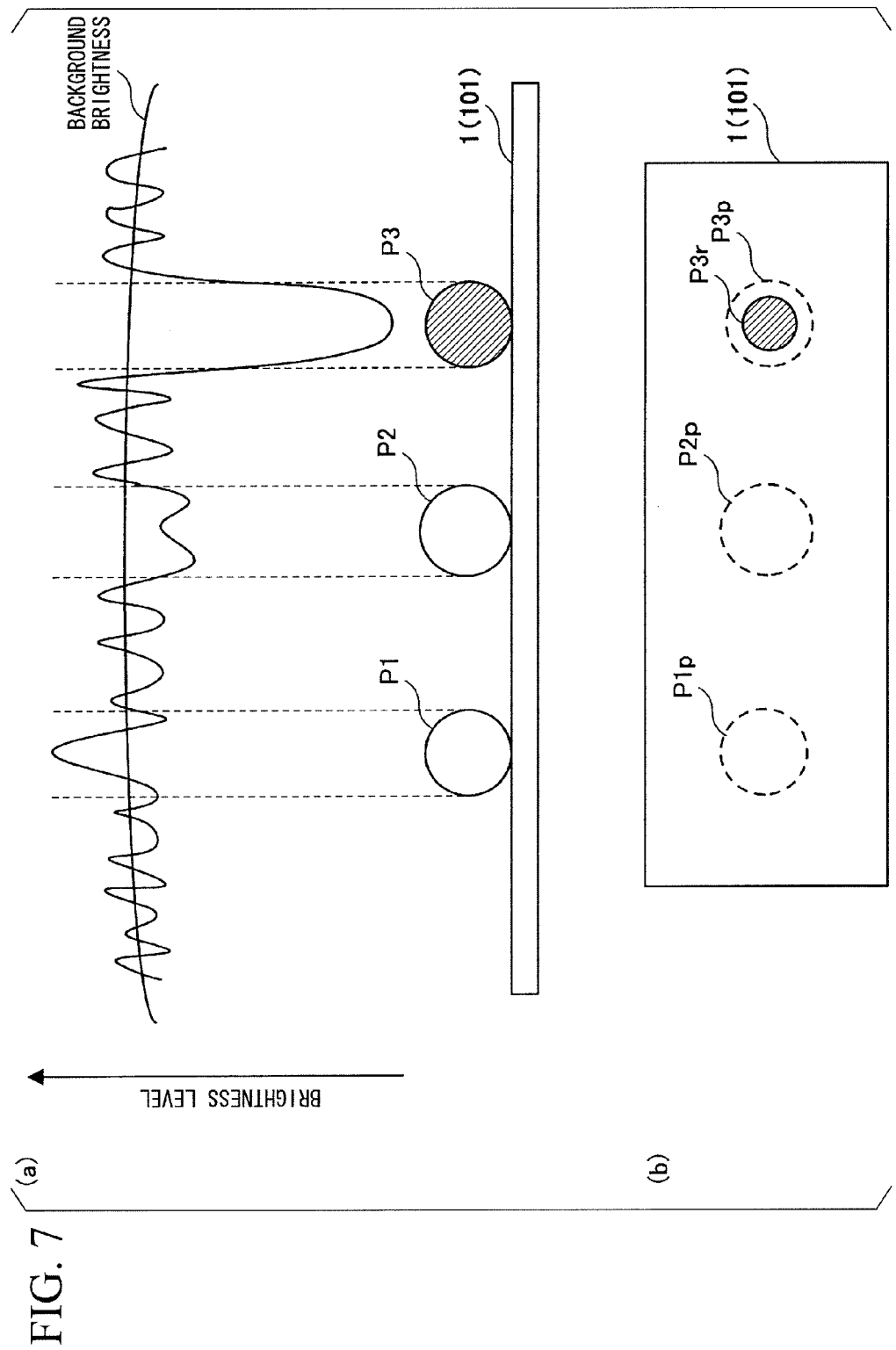
FIG. 7 is an explanatory diagram that illustrates another example of the image processing method using a reflected light image according to the embodiment.

Here, a method of detecting a reflected light particle will be described with reference to FIGS. 6 and 7. FIG. 6 is an explanatory diagram that illustrates an example of an image processing method using a reflected light image according to the embodiment. FIG. 7 is an explanatory diagram that illustrates another example of the image processing method using a reflected light image according to the embodiment.

As illustrated in FIGS. 6($a$) and 7($a$), the brightness levels of pixels in the reflected light image are determined by the brightness levels of the fine particles P1, P2, and P3. In other words, since the reflected light image is captured by using reflected light of light emitted toward the substrate 1 or the stage 101 on which the fine particles P1, P2, P3 are sprayed, the brightness levels of the captured images (reflected light particles) of the fine particles on the reflected light image are in correspondence with the brightness levels of the actual fine particles P1, P2, and P3. For example, in a case where the fine particles P1 and P2 are particles having high brightness levels (bright-color particles; brightness level of P1>brightness level of P2), and the fine particle P3 is a particle having a low brightness level (dark-color particle), in the reflected light image, the brightness levels of pixels corresponding to areas in which the fine particles P1 and P2 are present are recognized as bright colors (areas having high brightness levels), and the brightness level of the pixel corresponding to an area in which the fine particle P3 is present is recognized as a dark color (area having a low brightness level).

In an example of the method of detecting a reflected light particle in the embodiment, as illustrated in FIG. 6($a$), first, a reflected light image is binarized using a predetermined brightness threshold value Tr1, whereby a reflected light binarized image is generated. As the predetermined brightness threshold value Tr1 at this time, for example, the above-described "brightness threshold value used for identifying the level of the brightness of a particle" may be used. In addition, before the reflected light image is binarized, the variations of the luminance within the image may be corrected by increasing or decreasing the recorded brightness level of the pixel by a correction value that is a function of the two-dimensional position of a pixel, which is the same as the case in which the transmitted image is binarized.

The reflected light binarized image acquired as above, as illustrated in FIG. 6($b$), is formed by pixels having high brightness levels (illustrated as a white area) and pixels having low brightness levels (illustrated as areas of slanting lines). Accordingly, based on the connection relation of the binarized brightness levels of pixels that are adjacent to each other in the reflected light binarized image, an area, in which pixels (in the embodiment, pixels having low brightness levels) having the same binarized brightness level are continuous, and that are independent from the other areas (in the embodiment, areas in which pixels having high brightness levels are present) is specified as a reflected light particle P3$r$ that is a candidate for a particle. In addition, the position coordinates of the pixels within the specified area in which the reflected light particle P3$r$ is present are detected, the position (for example, the center position) and the size (for example, the area or the diameter) of the reflected light particle Pr are calculated based on the position coordinates, and the position and the size are recorded in a storage device (not illustrated in the figure) disposed in the image processing device 130 or the like (S117). Furthermore, in FIG. 6($b$), for the reference, areas (acquired by the transmitted light binarized image) in which the particles are present are denoted by broken lines as P1$p$, P2$p$, and P3$p$. As above, in the reflected light image, all the particles disposed on the substrate 1 cannot be constantly recognized, and in a recognized particle, the particle area may be markedly different from the cross-section of the actual particle.

In addition, as illustrated in FIG. 7($a$), in a case where there is a large difference between the brightness level of a pixel area that can be recognized as a particle within the reflected image captured by the imaging device 110 and the brightness level of a pixel area (background) located on the periphery of the pixel area, and it is easy to directly recognize a particle from the reflected light image, as illustrated in FIG. 7($b$), the area in which the reflected light particle Pr is present can be specified directly from the reflected light image without binarizing the reflected light image as described above. For example, a particle range can be specified by identifying the contour of a particle using the brightness gradient in the image. Then, the position coordinates of a pixel located in the specified area in which the reflected light particle Pr is present may be detected.

In addition, the process as described above can be performed by using a particle image processing and measuring function that is mounted as a standard in image processing software that is available in the market such as Image-Pro Plus (registered trademark of Media Cybernetics, Inc.). For example, in Image-Pro Plus ver. 5, for a specific digital image, general particle image processing functions, for example, functions for binarization, brightness conversion, pixel brightness calculation, particle identification, calculation of the centroid position of a particle, assigning a number to a particle, calculating characteristics amounts (the brightness, the hue, the area, the aspect ratio, roundness, and the like) of a particle, identifying the presence of a hole in a particle, calculating the area ratio of a hole to a particle in a case where the hole is present, and the like are included.

In the image processing process, next, by comparing the positions and the sizes of one or two or more transmitted light particles that are calculated as described above and the positions and the sizes of one or two or more reflected light particles with each other, an association process is performed in which a transmitted light particle and a reflected light particle having differences in the position and the size are within a predetermined range are associated with each other (S119).

The association process according to the embodiment, for example, is performed by comparing individual reflected light particles with all the transmitted light particles (a transmitted light particle that has been already associated with a specific reflected light particle is excluded). More specifically, distances (inter-center position distances) between the center position of a reflected light particle of interest and the center positions of all the transmitted light particles to be compared with the reflected light particle are calculated, and, out of transmitted light particles for which the inter-center position distance is smaller than a predetermined limit distance, a transmitted light particle having a shortest inter-center position distance is set as a candidate for a transmitted light particle corresponding to the reflected light particle of interest. As an example of the limit distance, for example, there is a length that is close to an average diameter of fine particles P that are measurement targets (10 μm in a case where the fine particles P are falling dusts that are originated from an iron manufacturing plant), a length corresponding to 30% of the diameter of the transmitted light particle to be compared with the reflected light particle, or the like.

Next, the areas of the reflected light particle of interest and the candidate for a corresponding transmitted light particle are compared with each other, and, in a case where the ratio between the areas (for example, the area of the reflected light particle/the area of the transmitted light particle) is within a predetermined limit ratio, the candidate for the transmitted light particle is associated with the reflected light particle of interest. For example, the range of the limit ratio is 0.5 to 1.2. On the other hand, in a case where the ratio between the areas is beyond a predetermined range of limit ratios, the transmitted light particle is determined not to be in correspondence with the reflected light particle of interest. In this way, in a case where there is no transmitted light particle that is associated with the reflected light particle of interest, the reflected light particle is determined to be a false particle, that is, not a candidate for a captured image of a fine particle P and is excluded from the candidate for a captured image of a fine particle P.

At the time of performing the association process, in the embodiment, a reflected light image is captured in a state in which the brightness level of the background (a peripheral area of a pixel area that is identified as a particle) of the reflected light image is set to be higher than the "brightness threshold value used for identifying the level of the brightness of a particle". Accordingly, a fine particle that is identified as a particle on the reflected light binarized image is a particle having a brightness level that is lower than the brightness level of the background, in other words, only a particle image corresponding to the dark-color fine particle P3, and the particle images corresponding to the bright-color fine particles P1 and P2 are not recognized on the reflected light binarized image according to the embodiment.

Thus, in the embodiment, as a result of the association process, in a case where there is a transmitted light particle (P3p illustrated in FIG. 5) that is associated with the reflected light particle (P3r illustrated in FIGS. 6 and 7), a fine particle (P3) corresponding to the transmitted light particle (P3p) is identified as a dark-color particle having a brightness level that is lower than the brightness threshold value used for identifying the level of the brightness of a particle (S121). On the other hand, as the result of the determination made in Step S121, in a case where there are transmitted light particles (P1p and P2p illustrated in FIG. 5) that are not associated with any reflected light particle, fine particles (P1 and P2) corresponding to the transmitted light particles (P1p and P2p) are identified as bright-color particles having brightness levels higher than the brightness threshold value used for identifying the level of the brightness of a particle (S123). In addition, in a case where there is a reflected light particle that is not associated with any transmitted light particle, the reflected light particle is excluded from the candidate for the captured image of a fine particle (S125).

Based on the result of the association process, the position and the size of the transmitted light particle are calculated as the position and the size of the fine particle P, and the representative brightness level of the reflected light particle or the transmitted light particle as the brightness level of the fine particle P (S127). More specifically, the center position and the size (the radius or the area) of the transmitted light particle that is associated with a reflected light particle are calculated as the position and the size of the fine particle P that corresponds to the transmitted light particle, and the representative brightness level of the reflected light particle is calculated as the brightness level of the fine particle P (in the case of the embodiment, a dark-color particle having a brightness level that is lower than the brightness threshold value used for identifying the level of the brightness of the particle is assumed). In addition, while the method of calculating the center position and the size of the transmitted light particle that is not associated with any reflected light particle is as described above, the brightness level of the fine particle P is calculated as the representative brightness level of the transmitted light particle (in the embodiment, a bright-color particle having a brightness level that is higher than the brightness threshold value used for identifying the level of the brightness of a particle is assumed).

Furthermore, as the information relating to the fine particle P, a volume in a case where the fine particle P is assumed to be a sphere may be calculated based on the particle diameter of the fine particle P acquired in advance and be recorded. In addition, as necessary, for each brightness level of the particle (in the embodiment, for each of the dark-color particles and the bright-color particles), the particle size composition ratio, a total volume, a ratio between total volumes of dark-color particles and bright-color particles, and the like may be calculated and recorded, as appropriate.

Figure 8:
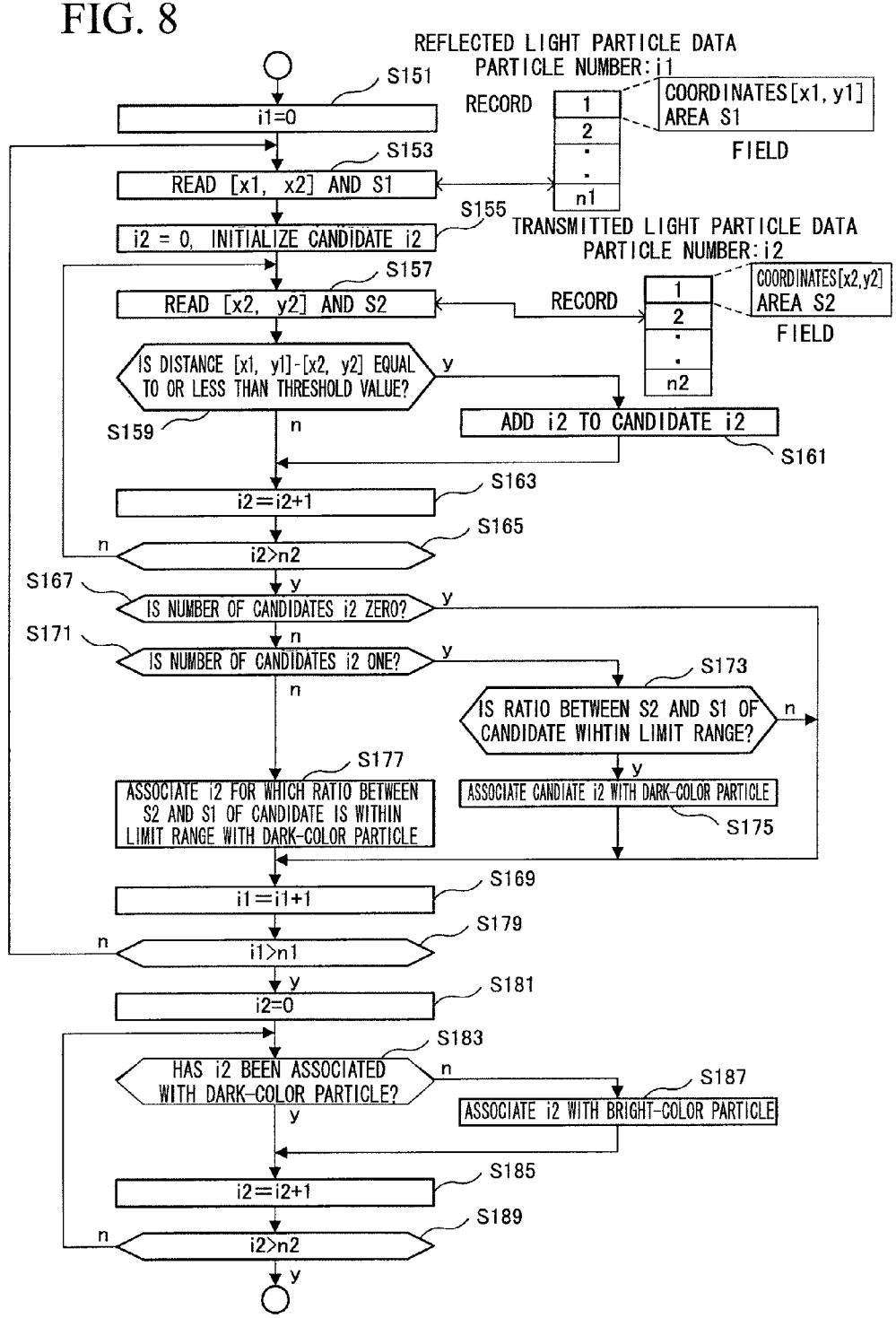
FIG. 8 is a flowchart that illustrates an example of the flow of an association process according to the embodiment.

Here, the above-described association process will be described in detail with reference to FIG. 8. FIG. 8 is a flowchart that illustrates an example of the flow of the association process according to the embodiment. In addition, for example, in the example of the association process illustrated in FIG. 8, in the storage device (not illustrated in the figure) disposed in the particle measuring device 100, particle numbers it (i1=1, 2, . . . , n1) used for identifying individual particles and the pixel coordinates [Xi1, Yi1] of the center positions and the areas Si1 of individual particles are recorded as data of the reflected light particles with being associated with one another. In addition, in the storage device (not illustrated in the figure) disposed in the particle measuring device 100, particle numbers i2 (i2=1, 2, . . . , n2) used for identifying individual particles and the pixel coordinates [Xi2, Yi2] of the center positions and the areas Si2 of individual particles are recorded as data of the transmitted reflected light particles with being associated with one another. In addition, the coordinates of the center position of the reflected light particle having i1=1 is represented as [X11, Y11], the area thereof is represented as Si1, the coordinates of the center position of the transmitted light particle having i2=1 is represented as [X21, Y21], and the area thereof is represented as S21. Hereinafter, an example of the association process method using such data will be described in detail.

As illustrated in FIG. 8, first, a determination of reflected light particles is made. The particle number i1 of the reflected light particle is initialized so as to be "i1=0" (S151), and data relating to the reflected light particle having a particle number i1=1, in other words, the coordinates [X11, Y11] of the center position of the reflected light particle having i1=1 and the area S11 thereof are read out (S153). Similarly, the particle number i2 of the transmitted light particle is initialized so as to be "i2=0" (S155), and data relating to the transmitted light particle having a particle number i2=1, in other words, the coordinates [X21, Y21] of the center position of the transmitted light particle having i2=1 and the area S21 thereof are read out (S157)

Thereafter, for a case of i1=1 and i2=1, it is determined whether or not a distance (inter-center position distance) between [X11, Y11] and [X21, Y21] is equal to or less than a predetermined limit distance (for example, 10 µm) (S159). As a result of the determination, in a case where the inter-center position distance is determined to be equal to or less than the limit distance, as a candidate (association candidate) of the transmitted light particle that is associated with the reflected light particle having i1=1, a transmitted light particle i2=1 is added (S161), and add one to i2 (S163) so as to be "i2=2". On the other hand, as a result of the determination made in Step S159, in a case where the inter-center position distance is determined to exceed the limit distance, as an association candidate, a transmitted light particle having i2=1 is not added, and one is added to i2 (S163) so as to be "i2=2".

Thereafter, from the storage device, data relating to a transmitted light particle having a particle number i2=2, in other words, the coordinates [X22, Y22] of the center position of the transmitted light particle having i2=2 and the area S22 thereof are read out (S157). In this way, the process of Steps S159 to S163 is repeated until "i2>n2" (S165). In other words, the process of Steps S157 to S163 is performed for all the values of i2 (=1 to n2).

Thereafter, as a result of the above-described processes, it is determined whether or not the number of candidates for transmitted light particles that are associated with the reflected light particle having i1=1 is zero (S167), and, in a case where the number of candidates is zero, the association of the particle is not performed, one is added to i1 to be i1=2, and the process proceeds to the process of the next reflected light particle data (S169). On the other hand, as the result of the determination made in Step S167, in a case where the number of candidates is not zero, it is determined whether or not the number of candidates is one (S171).

As the result of the determination made in Step S171, in a case where the number of candidates is one (for example, in a case where a particle having i2=1 is the candidate), it is determined whether or not the ratio between the area Si2 of the transmitted light particle and the area Si1 of the reflected light particle of this candidate is within the range of limit ratios (S173). As a result of the determination made in Step S173, in a case where the ratio is within the range of limit ratios, the transmitted light particle (i2=1) and the reflected light particle (i1=1) are associated with each other, the particle image is identified as a captured image of a fine particle P having a dark color (low brightness level) (S175), one is added to i1 to be i1=2, and the process proceeds to the process of the next reflected light particle data (S169). On the other hand, as the result of the determination made in Step S173, in a case where the ratio is beyond the range of limit ratios, the transmitted light particle and the reflected light particle are not associated with each other, and one is added to i1 (S169) to be "i1=2".

In addition, as the result of the determination made in Step S171, in a case where the number of candidates is not one, in other words, in a case where the number of candidates is two or more, out of such candidates, only the transmitted light particle having a particle number of i2, of which the area ratio between the area Si1 of the reflected light particle and the area Si2 of the transmitted light particle is within a predetermined range of limit ratios, is associated with the reflected light particle (i1=1). In other words, there are cases where a plurality of transmitted light particles are associated with the same reflected light particle. Thereafter, such a particle image is identified as a captured image of a fine particle P having a dark color (low brightness level) (S177), one is added to i1 to be i1=2, and the process proceeds to the process of the next reflected light particle data (S169).

Thereafter, in the particle association process for the next reflected light particle data (i1=2), data relating to the transmitted light particle having a particle number i1=2, in other words, the coordinates [X12, Y12] of the center position of the transmitted light particle having i1=2 and the area S12 thereof are read out from the storage device (S157). In this way, the process of Steps S153 to S177 is repeated until "I1>n1" (S179). In other words, the process of Steps S153 to S177 is performed for all the values of i1 (=1 to n1).

After the completion of the above-described process, a determination of a transmitted light particle is made. Again, the particle number i2 is initialized to be "i2=0" (S181). In addition, the number of reflected light particles (i1=1 to n1) that are associated with the transmitted light particle (identified as a dark-color particle) is determined from a transmitted light particle having i2=1 (S183). As a result of this determination, in a case where the transmitted light particle is associated with any reflected light particle, one is added to i2 to be i2=2, and the process proceeds to the process of next reflected light particle data (S185). On the other hand, as the result of the determination made in Step S183, in a case where the transmitted light particle is not associated with any reflected light particle, the transmitted light particle is identified as a bright-color particle (S187), one is added to i2 to be i2=2, and the process proceeds to the process of next reflected light particle data (S185).

Thereafter, for the transmitted light particle having i2=2, the above-described process of Steps S183 to S187 is performed, and the above-described process is repeated until "i2>n2" (S189). In other words, the process of Steps S183 to S187 is performed for all the values of i2 (=1 to n2).

In this way, all the transmitted light particle (i2=1 to n2) can be identified as one of the dark-color particle and the bright-color particle. In addition, the reflected light particle that is not associated with any transmitted light particle is excluded from the candidates for the captured image of a fine particle P that is a measurement target.

(Advantages of Particle Measuring Device and Particle Measuring Method According to this Embodiment)

According to the particle measuring device 100 according to the above-described embodiment and the particle measuring method using this, illumination is performed by the reflected light illuminating device 121 from the upper side of a fine particle P, and, in a case where multiple external disturbances having high brightness levels are mainly predicted in a particle image that is acquired by capturing the fine particle P using reflected light from the fine particle P, particle image processing and measuring can be performed with high accuracy.

As a first representative example of the external disturbance having a high brightness level, there is a highlight due to specular reflection of illumination (illumination emitted from the reflected light illuminating device 121) from the upper side. In a particle image in which such highlights are present, the ratio of the number of pixels of highlight portions to the number of pixels corresponding to the fine particle P, generally, is equal to or higher than 10% and less than 50%. In a case where the brightness level of a fine particle is determined by only using an image captured using the illumination (reflected light) emitted from the upper side, even an originally dark-color particle having a low brightness level has a high brightness level in a highlight portion, and there is a possibility that the dark-color particle is misrecognized as a bright-color particle. In contrast to this, according to the embodiment, even when a highlight portion is present, the original brightness level of the particle can be determined based on only the dark-color portion of the particle. In addition, since the area of the particle is calculated based on an image that is captured using illumination (transmitted light)

emitted from the lower side, in the image captured using the illumination (reflected light) emitted from the upper side, an measurement error in the area of the particle due to recognition of the dark-color particle as a particle as a shape in which the highlight portion lacks does not occur.

In addition, for the same reason, according to the embodiment, an object captured through specular reflection (for example, specular reflection from the stage surface) from a place other than the particle is not misrecognized as a particle.

Furthermore, as a second representative example of the external disturbance having a high brightness level, there is a particle (for example, a dirt on a microscopic lens) other than the measurement target that is present beyond the focal distance range. Even a particle (for example, a dust) other than the measurement target that is not present on the stage 101 may be recorded as an image when the particle is present within the imaging range. Since such a particle is not in focus for imaging means (camera), it is out of focus and is recorded as a large pixel having a slightly high brightness level. This is similar in an image that is captured using illumination (reflected light) emitted from the upper side and an image that is captured using illumination (transmitted light) emitted from the lower side. In a case where the brightness level of such a particle is determined only using the image that is captured using the illumination emitted from the upper side, it cannot be determined whether the particle is a particle having a low brightness level or a particle other than the measurement target. In contrast to this, according to the embodiment, when image processing is performed by binarizing an image captured using the illumination emitted from the lower side, the particle having a high brightness level due to such out-of-focus is excluded from the target for measuring a particle (in the image captured using illumination emitted from the lower side of an in-focus particle, a pixel area corresponding to the particle constantly has a low brightness level equal to or less than a predetermined value), and accordingly, the particle other than the measurement target is not misrecognized.

Second Embodiment

Next, a particle measuring device and a particle measuring method according to a second embodiment of the present invention will be described, and, mainly, configurations that are different from those of the above-described first embodiment will be described in detail.
(Particle Measuring Device)
The particle measuring device according to this embodiment is different from the above-described particle measuring device 100 according to the first embodiment in the functions of a reflected light image generating unit, a reflected light particle detecting unit, and a particle information calculating unit.

More specifically, the reflected light image generating unit according to this embodiment generates a reflected light image in a state in which the luminance of a transmitted light illuminating device is set by an illumination control device such that the brightness level of the background of the reflected light particle on the reflected light image is lower than the brightness threshold value used for identifying the level of the brightness of a particle, in contrast to the first embodiment.

In addition, the reflected light particle detecting unit according to this embodiment specifies a pixel area in which pixels having high brightness levels are aggregated in the pixel coordinates of the reflected light image and detects the position coordinates of a pixel within an area in which the reflected light particle is present, based on a brightness distribution of a reflected light binarized image that is acquired by binarizing the reflected light image using the brightness threshold value used for identifying the level of the brightness of a particle.

In other words, in the reflected light binarized image according to this embodiment, the brightness level of the background is on the lower brightness side, and only a particle P having a brightness level that is higher than the brightness threshold value used for identifying the level of the brightness of a particle is recognized as a reflected light particle.

Thus, the particle information calculating unit according to this embodiment identifies a fine particle P corresponding to a transmitted light particle that is associated with the reflected light particle, by using the association processing unit, as a bright-color particle having a brightness level that is higher than the brightness threshold value used for identifying the level of the brightness of a particle and identifies a fine particle P corresponding to the transmitted light particle that is not associated with any reflected light particle as a dark-color particle having a brightness level that is lower than the brightness threshold value used for identifying the level of the brightness of a particle.

Figure 9:
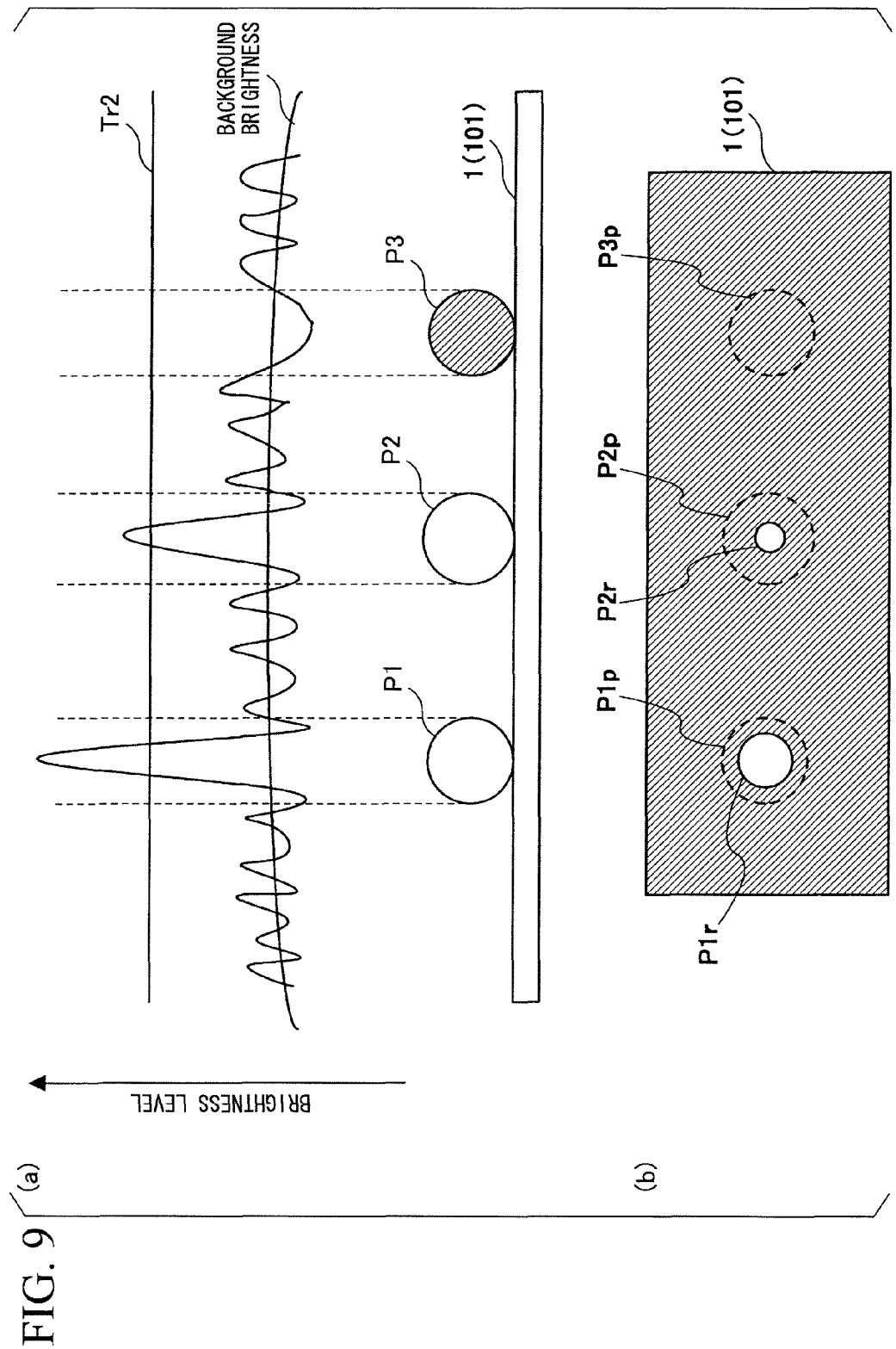
FIG. 9 is an explanatory diagram that illustrates an example of the image processing method using a reflected light image according to a second embodiment of the present invention.

In other words, in this embodiment, to the contrary to the case of the first embodiment, a fine particle corresponding to a transmitted light particle that is associated with a reflected light particle is a bright-color particle, and a fine particle corresponding to a transmitted light particle that is not associated with any of the reflected light particle is a dark-color particle.
(Particle Measuring Method)
As above, while the particle measuring device according to this embodiment has been described, subsequently, a method of detecting a reflected light particle in the particle measuring method according to this embodiment will be described with reference to FIG. 9. FIG. 9 is an explanatory diagram that illustrates an example of the image processing method using a reflected light image according to this embodiment.

As illustrated in FIG. 9(a), the brightness levels of pixels in the reflected light image are determined by the brightness levels of the fine particles P1, P2, and P3. In other words, since the reflected light image is captured by using reflected light of light emitted toward the substrate 1 or the stage 101 on which the fine particles P1, P2, P3 are sprayed, the brightness levels of the captured images (reflected light particles) of the fine particles on the reflected light image are in correspondence with the brightness levels of the actual fine particles P1, P2, and P3. For example, in a case where the fine particles P1 and P2 are particles (bright-color particles; brightness level of P1>brightness level of P2) having high brightness levels, and the fine particle P3 is a particle having a low brightness level (dark-color particle), in the reflected light image, the brightness levels of pixels corresponding to areas in which the fine particles P1 and P2 are present are recognized as bright colors (areas having high brightness levels), and the brightness level of the pixel corresponding to an area in which the fine particle P3 is present is recognized as a dark color (area having a low brightness level).

In an example of the method of detecting a reflected light particle in the embodiment, as illustrated in FIG. 9(a), first, a reflected light image is binarized using a predetermined brightness threshold value Tr2, whereby a reflected light binarized image is generated. As the predetermined brightness threshold value Tr2 at this time, for example, the above-described "brightness threshold value used for identifying the level of the brightness of a particle" may be used. In addition, before the reflected light image is binarized, the variations of the luminance within the image may be corrected by increasing or decreasing the recorded brightness level of the pixel by a correction value that is a function of the two-dimensional position of the pixel, which is the same as the case of the first embodiment.

The reflected light binarized image acquired as above, as illustrated in FIG. 9(b), is formed by pixels having high brightness levels (illustrated as a white area) and pixels having low brightness levels (illustrated as areas of slanting lines). Accordingly, based on the connection relation of the binarized brightness levels of pixels that are adjacent to each other in the reflected light binarized image, areas, in which pixels (in the embodiment, pixels having high brightness levels) having the same binarized brightness level are continuous, that are independent from the other areas (in the embodiment, areas in which pixels having low brightness levels are present) are specified as reflected light particles P1r and P2r that are candidates for a particle. In addition, the position coordinates of the pixels within the specified area in which the reflected light particle Pr is present are detected, the position (for example, the center position) and the size (for example, the area or the diameter) of the reflected light particle Pr are calculated based on the position coordinates, and the position and the size are recorded in a storage device (not illustrated in the figure) disposed in the image processing device or the like.

Next, similarly to the first embodiment, although the process of association between the reflected light particle and the transmitted light particle is performed, at the time of performing the association process, in this embodiment, a reflected light image is captured in a state in which the brightness level of the background (a peripheral area of a pixel area that is identified as a particle) of the reflected light image is set to be lower than the "brightness threshold value used for identifying the level of the brightness of a particle". Accordingly, fine particles that are identified as particles on the reflected light binarized image are particles having brightness levels that are higher than the brightness level of the background, in other words, only particle images corresponding to the bright-color fine particles P1 and P2, and the particle image corresponding to the dark-color fine particle P3 is not recognized on the reflected light binarized image according to the embodiment.

Thus, in this embodiment, as a result of the association process, in a case where there are transmitted light particles (P1p and P2p illustrated in FIG. 5) that are associated with the reflected light particles (P1r and P2r illustrated in FIG. 9), fine particles (P1 and P2) corresponding to the transmitted light particles (P1p and P2p) are identified as bright-color particles having brightness levels that are higher than the brightness threshold value used for identifying the level of the brightness of a particle. On the other hand, as the result of the association process, in a case where there is a transmitted light particle (P3p illustrated in FIG. 5) that is not associated with any reflected light particle, a fine particle (P3) corresponding to the transmitted light particle (P3p) is identified as a dark-color particle having a brightness level lower than the brightness threshold value used for identifying the level of the brightness of a particle. In addition, in a case where there is a reflected light particle that is not associated with any transmitted light particle, the reflected light particle is excluded from the candidate for the captured image of a fine particle P, which is the same as the first embodiment.

Based on the result of the association process, the position and the size of the transmitted light particle are calculated as the position and the size of the fine particle P, and the representative brightness level of the reflected light particle or the transmitted light particle as the brightness level of the fine particle P. More specifically, the center position and the size (the radius or the area) of the transmitted light particle that is associated with a reflected light particle are calculated as the position and the size of the fine particle P that corresponds to the transmitted light particle, and the representative brightness level of the reflected light particle is calculated as the brightness level of the fine particle P (in the case of this embodiment, a bright-color particle having a brightness level that is higher than the brightness threshold value used for identifying the level of the brightness of the particle is assumed). In addition, while the method of calculating the center position and the size of the transmitted light particle that is not associated with any reflected light particle is as described above, the brightness level of the fine particle P is calculated as the representative brightness level of the transmitted light particle (in this embodiment, a dark-color particle having a brightness level that is lower than the brightness threshold value used for identifying the level of the brightness of a particle is assumed).

Furthermore, as the information relating to the fine particle P, a volume in a case where the fine particle P is assumed to be a sphere may be calculated based on the particle diameter of the fine particle P acquired in advance and be recorded. In addition, as necessary, for each brightness level of the particle (in the embodiment, for each of the dark-color particles and the bright-color particles), the particle size composition ratio, a total volume, a ratio between total volumes of dark-color particles and bright-color particles, and the like may be calculated and recorded, as appropriate.

(Advantages of Particle Measuring Device and Particle Measuring Method According to this Embodiment)

According to the particle measuring device according to this embodiment described above and the particle measuring method using this, illumination is performed by the reflected light illuminating device from the upper side of a fine particle, and, in a case where multiple external disturbances having low brightness levels are mainly predicted in a particle image that is acquired by capturing the fine particle using reflected light from the fine particle, particle image processing and measuring can be performed with high accuracy.

As a representative example of the external disturbance having a low brightness level, there is a semi-transparent dust, which is placed on a transparent stage on which a substrate on which fine particles that are measurement targets are sprayed is placed or on which fine particles are directly sprayed. On the transparent stage, frequently, there are cases where a semi-transparent dust such as oil or a fingerprint is present, and there are cases where such a dust is imaged. In a case where a fine particle, which is a measurement target, has mainly a high brightness level, and a brightness threshold value used for the identification from a dark-color particle having a relatively low brightness level is set to a relatively high brightness level, in identifying a particle of only an image captured using the illumination emitted from the upper side, there is a possibility that the semi-transparent dust placed on the stage is misrecognized as a particle. In contrast to this, according to this embodiment, when image processing is performed by binarizing an image captured using the illumination emitted from the lower side, such a dust placed on the stage is excluded from the measurement target, and accordingly, the dust placed on the stage is not misrecognized as a particle.

Third Embodiment

Next, a particle measuring device and a particle measuring method according to a third embodiment of the present invention will be described, and, mainly, configurations that are different from those of the above-described first and second embodiments will be described in detail.

(Particle Measuring Device)

The particle measuring device according to this embodiment is different from the above-described particle measuring devices 100 according to the first and second embodiments in the functions of a reflected light image generating unit, a reflected light particle detecting unit, and a particle information calculating unit. Described in more detail, the reflected light image generating unit and the reflected light particle detecting unit according to this embodiment have the functions of both the first and second embodiments described above, and accordingly, the particle information calculating unit according to this embodiment, differently from those of the first and second embodiments, can identify the brightness levels of fine particles, which are measurement targets, as three types including an intermediate-color particle in addition to the bright-color particle and the dark-color particle. Hereinafter, detailed description thereof will be presented.

The reflected light image generating unit according to this embodiment, similarly to that of the second embodiment, first, generates a dark-background reflected light image acquired by imaging fine particles, which are measurement targets, in a state in which the luminance of a transmitted light illuminating device is set by an illumination control device such that the brightness level of the background of the reflected light particle on the reflected light image is lower than a first brightness threshold value (hereinafter, referred to as a "dark-background brightness threshold value Tr3(D)") used for identifying the level of the brightness of a particle.

In addition, the reflected light image generating unit according to this embodiment, first, defines a second brightness threshold value (defined as Tr3(B)) that is a brightness threshold value lower than the dark-background brightness threshold value Tr3(D) in advance. Next, similarly to the first embodiment, the reflected light image generating unit generates a bright-background reflected light image acquired by imaging fine particles, which are measurement targets, in a state in which the luminance of the transmitted light illuminating device is set by the illumination control device such that the brightness level of the background of the reflected light particle on the reflected light image is higher than Tr3(B).

Here, while the dark-background brightness threshold value Tr3(D) and the bright-background brightness threshold value Tr3(B) can be acquired by using a method that is the same as the method of acquiring a "brightness threshold value used for identifying the level of the brightness of a particle" described in the first and second embodiments, in this embodiment, it is important that the dark-background brightness threshold value Tr3(D) is higher than the bright-background brightness threshold value Tr3(B).

In addition, the reflected light particle detecting unit according to this embodiment, first, similarly to the case of the second embodiment, specifies a pixel area in which pixels having high brightness levels are aggregated in the pixel coordinates of the dark-background reflected light image as an area in which the reflected light particle is present and detects the position coordinates of a pixel within an area in which the reflected light particle is present, based on a brightness distribution of a reflected light binarized image that is acquired by binarizing the dark-background reflected light image using the dark-background brightness threshold value Tr3(D).

Furthermore, the reflected light particle detecting unit according to this embodiment, similarly to the case of the first embodiment, specifies a pixel area in which pixels having low brightness levels are aggregated in the pixel coordinates of the bright-background reflected light image as an area in which the reflected light particle is present and detects the position coordinates of a pixel within an area in which the reflected light particle is present, based on a brightness distribution of a bright-background reflected light binarized image that is acquired by binarizing the bright-background reflected light image using the bright-background brightness threshold value Tr3(B).

In other words, in this embodiment, in the dark-background reflected light binarized image, the brightness level of the background is on the lower brightness side, and only a particle having a brightness level that is higher than the dark-background brightness threshold value Tr3(D) is recognized as a reflected light particle, and in the bright-background reflected light binarized image, the brightness level of the background is on the higher brightness side, and only a particle having a brightness level that is lower than the bright-background brightness threshold value Tr3(B) is recognized as a reflected light particle. In addition, a fine particle that has a brightness level higher than the bright-background brightness threshold value Tr3(B) and a brightness level lower than the dark-background brightness threshold value Tr3(D) cannot be identified in both the dark-background reflected light binarized image and the bright-background reflected light binarized image.

Thus, the particle information calculating unit according to this embodiment identifies a fine particle corresponding to a transmitted light particle that is associated with the reflected light particle, by using the association processing unit, as a bright-color particle having a brightness level that is higher than the dark-background brightness threshold value Tr3(D) and identifies a fine particle corresponding to the transmitted light particle that is associated with the reflected light particle that is present within the bright-background reflected light image as a dark-color particle having a brightness level that is lower than the bright-background brightness threshold value Tr3(B). In addition, the particle information calculating unit according to this embodiment identifies a fine particle corresponding to the transmitted light particle that is not associated with any reflected light particle as an intermediate-color particle having a brightness level (in this embodiment, a brightness level that is higher than the bright-background brightness threshold value Tr3(B) and is lower than the dark-background brightness threshold value Tr3(D)) that is between the bright-color particle and the dark-color particle.

In other words, in this embodiment, a fine particle corresponding to a transmitted light particle that is associated with a reflected light particle that is present in any dark-background reflected light image is a bright-color particle, a fine particle corresponding to a transmitted light particle that is associated with a bright-background reflected light particle that is present within any bright-background reflected image is a dark-color particle, and a fine particle corresponding to a transmitted light particle that is not associated with any reflected light particle is an intermediate-color particle.

(Particle Measuring Method)

Figure 10:
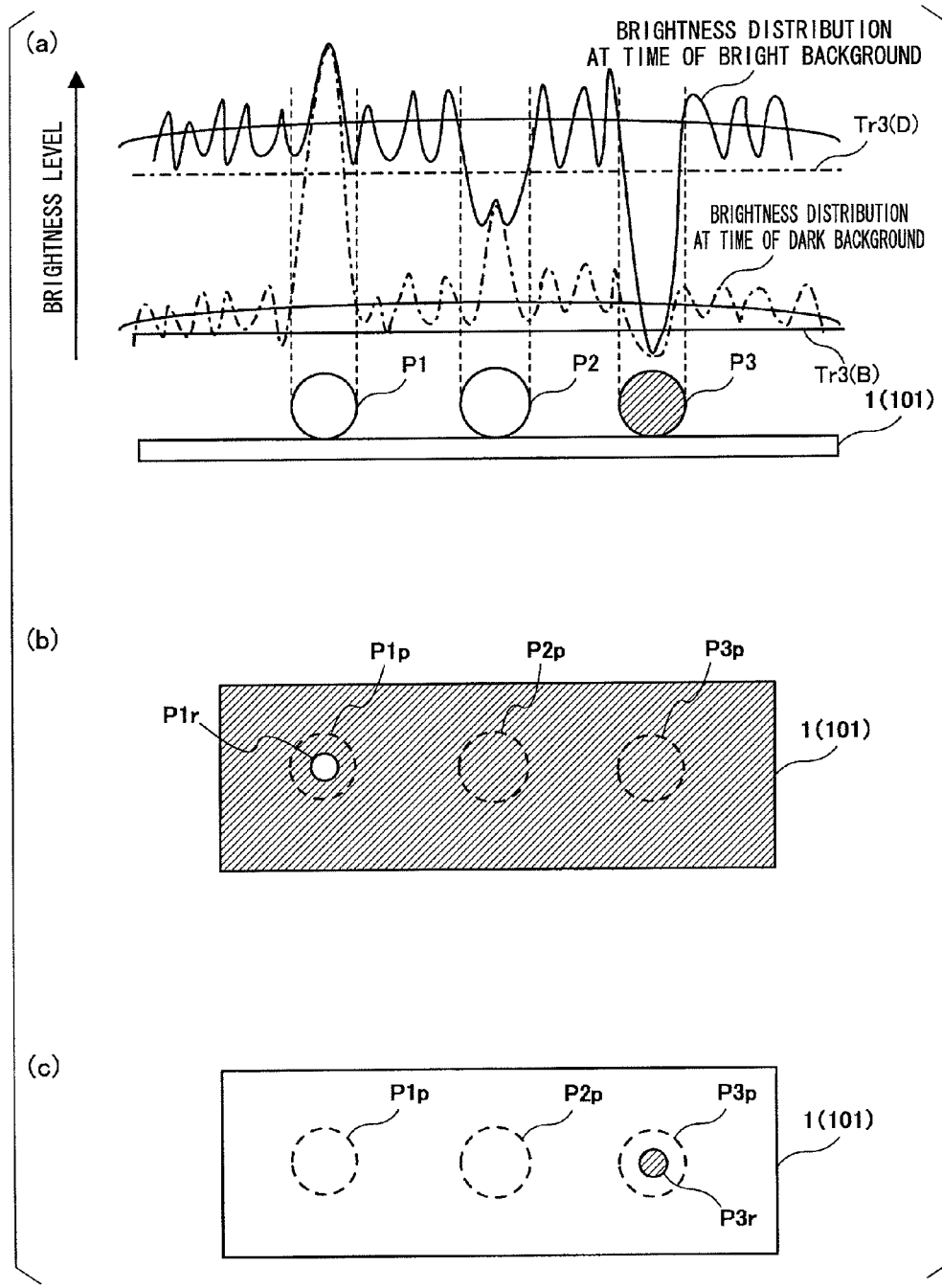
FIG. 10 is an explanatory diagram that illustrates an example of the image processing method using a reflected light image according to a third embodiment of the present invention.

As above, while the particle measuring device according to this embodiment has been described, subsequently, a method of detecting a reflected light particle in the particle measuring method according to this embodiment will be mainly described with reference to FIG. 10. FIG. 10 is an explanatory diagram that illustrates an example of the image processing method using a reflected light image according to this embodiment.

As illustrated in FIG. 10(a), the brightness levels of pixels in the reflected light image are determined by the brightness levels of the fine particles P1, P2, and P3. In other words, since the reflected light image is captured by using reflected light of light emitted toward the substrate 1 or the stage 101 on which the fine particles P1, P2, P3 are sprayed, the brightness levels of the captured images (reflected light particles) of the fine particles on the reflected light image are in correspondence with the brightness levels of the actual fine particles P1, P2, and P3. For example, in a case where the fine particle P1 is a bright-color particle having a high brightness level, the fine particle P2 is an intermediate-color particle having an intermediate brightness level, and the fine particle P3 is a particle having a low brightness level (dark-color particle), in the reflected light image, the brightness level of a pixel corresponding to an area in which the fine particle P1 is present is recognized as a bright color (an area having a high brightness level), the brightness level of the pixel corresponding to an area in which the fine particle P3 is present is recognized as a dark color (an area having a low brightness level), and the brightness level of a pixel corresponding to an area in which the fine particle P2 is present is recognized as an intermediate-color (an area having an intermediate brightness level).

In this embodiment, similarly to the case of the above-described first embodiment, a transmitted light image is generated by imaging a fine particle, which is a measurement target, using transmitted light, and a dark-background reflected light image is generated by imaging a fine particle using reflected light in a condition in which the brightness level of the background is lower than the "brightness threshold value used for identifying the level of the brightness of a particle". In addition, in this embodiment, similarly to the case of the above-described second embodiment, a bright-background reflected light image is generated by imaging a fine particle using reflected light in a condition in which the brightness level of the background is higher than the "brightness threshold value used for identifying the level of the brightness of a particle".

Thereafter, as illustrated in FIG. 10(a), first, a dark-background reflected light image is binarized using the dark-background brightness threshold value Tr3(D), whereby a dark-background reflected light binarized image is generated. As the dark-background brightness threshold value Tr3(D) at this time, for example, the above-described "brightness threshold value used for identifying the level of the brightness of a particle" may be used.

In addition, in this embodiment, a bright-background reflected light image is binarized using the bright-background brightness threshold value Tr3(B), whereby a bright-background reflected light binarized image is generated. As the bright-background brightness threshold value Tr3(B) at this time, for example, the above-described "brightness threshold value used for identifying the level of the brightness of a particle" may be used, and it is necessary that the bright-background brightness threshold value is lower than the dark-background brightness threshold value Tr3(D).

In addition, before the dark-background reflected light image and the bright-background reflected light image are binarized, the variations of the luminance within the image may be corrected by increasing or decreasing the recorded brightness level of the pixel by a correction value that is a function of the two-dimensional position of the pixel, which is the same as the case of each embodiment described above.

The dark-background reflected light binarized image and the bright-background reflected light binarized image, acquired as above, as illustrated in FIGS. 10(b) and 10(c), is formed by pixels having high brightness levels (illustrated as a white area) and pixels having low brightness levels (illustrated as areas of slanting lines). Accordingly, based on the connection relation of the binarized brightness levels of pixels that are adjacent to each other in the dark-background reflected light binarized image and the bright-background reflected light binarized image, areas, in which pixels (pixels having high brightness levels in the dark-background reflected light binarized image and pixels having low brightness levels in the bright-background reflected light binarized image) having the same binarized brightness level are continuous, that are independent from the other areas (areas in which pixels having low brightness levels are present in the dark-background reflected light binarized image, and areas in which pixels having high brightness levels are present in the bright-background reflected light binarized image) are specified as reflected light particles (P1$r$ in the dark-background reflected light particle and P3$r$ in the bright-background reflected light particle) that are candidates for a particle. In addition, the position coordinates of the pixels within the specified area in which the reflected light particle Pr is present are detected, the position (for example, the center position) and the size (for example, the area or the diameter) of the reflected light particle Pr are calculated based on the position coordinates, and the position and the size are recorded in a storage device (not illustrated in the figure) disposed in the image processing device or the like.

Next, similarly to the first embodiment, although the process of association between the reflected light particle and the transmitted light particle is performed, at the time of performing the association process, in this embodiment, a reflected light image is captured in a state in which the brightness level of the background (a peripheral area of a pixel area that is identified as a particle) of the dark-background reflected light image is set to be lower than the "brightness threshold value used for identifying the level of the brightness of a particle". Accordingly, fine particles that are identified as particles on the dark-background reflected light binarized image are particles having brightness levels that are higher than the brightness level of the background, in other words, only a particle image corresponding to the bright-color fine particles P1, and the particle images corresponding to the dark-color fine particle P3 and the intermediate-color fine particle P2 are not recognized on the dark-background reflected light binarized image according to this embodiment. On the other hand, a reflected light image is captured in a state in which the brightness level of the background (a peripheral area of a pixel area that is identified as a particle) of the bright-background reflected light image is set to be higher than the "brightness threshold value used for identifying the level of the brightness of a particle". Accordingly, fine particles that are identified as particles on the bright-background reflected light binarized image are particles having brightness levels that are lower than the brightness level of the background, in other words, only a particle image corresponding to the dark-color fine particle P3, and the particle images corresponding to the bright-color fine particle P1 and the intermediate-color fine particle P2 are not recognized on the bright-background reflected light binarized image according to this embodiment.

Thus, in this embodiment, for example, first, a first association process is performed using the dark-background reflected light binarized image. As a result, in a case where there is a transmitted light particle (P1$p$ illustrated in FIG. 5) that is associated with the reflected light particle (P1$r$ illustrated in FIG. 10(b)), a fine particle (P1) corresponding to the transmitted light particle (P1$p$) is identified as a bright-color particle having a brightness level that is higher (accordingly, higher than the brightness threshold value used for identifying the level of the brightness of a particle) than the dark-background brightness threshold value Tr3(D) used for identifying the level of the brightness of a particle.

Next, in this embodiment, as a result of the above-described first association process, a second association process is performed using the bright-background reflected light binarized image for a transmitted light particle (that is not identified as a bright-color particle) that is not associated with the reflected light particle on the dark-background reflected light binarized image. As a result, in a case where there is a transmitted light particle (P3p illustrated in FIG. 5) that is associated with the reflected light particle (P3r illustrated in FIG. 10(c)), the fine particle (P3) corresponding to the transmitted light particle (P3p) is identified as a dark-color particle having a brightness level that is lower than the bright-background brightness threshold value Tr3(B) (accordingly, lower than the brightness threshold value used for identifying the level of the brightness of a pixel).

On the other hand, as results of the above-described first and second association process, in a case where there is a transmitted light particle (P2p illustrated in FIG. 5) that is not associated with any reflected light particle, a fine particle (P2) corresponding to the transmitted light particle (P2p) is identified as an intermediate-color particle having a brightness level (in this embodiment, a brightness level that is higher than the bright-background brightness threshold value Tr3(B) and is lower than the dark-background brightness threshold value Tr3(D)) that is intermediate between the bright-color particle and the dark-color particle.

In addition, in a case where there is a reflected light particle that is not associated with any transmitted light particle, the reflected light particle is excluded from the candidate for the captured image of a fine particle P, which is the same as the first embodiment.

Based on the result of the association process performed as described above, the position and the size of the transmitted light particle are calculated as the position and the size of the fine particle P, and the representative brightness level of the reflected light particle or the transmitted light particle is calculated as the brightness level of the fine particle P. More specifically, the center position and the size (the radius or the area) of the transmitted light particle that is associated with a reflected light particle are calculated as the position and the size of the fine particle P that corresponds to the transmitted light particle, and the representative brightness level of the reflected light particle is calculated as the brightness level of the fine particle P (in the case of this embodiment, the fine particle is the bright-color particle or the dark-color particle). In addition, while the method of calculating the center position and the size of the transmitted light particle that is not associated with any reflected light particle is as described above, the brightness level of the fine particle P is calculated as the representative brightness level of the transmitted light particle (in this embodiment, the fine particle is an intermediate-color particle).

Furthermore, as the information relating to the fine particle P, a volume in a case where the fine particle P is assumed to be a sphere may be calculated based on the particle diameter of the fine particle P acquired in advance and be recorded. In addition, as necessary, for each brightness level of the particle (in the embodiment, for each of the dark-color particle, the bright-color particle, and the intermediate-color particle), the particle size composition ratio, a total volume, a ratio between total volumes of dark-color particles, bright-color particles, and intermediate-color particles, and the like may be calculated and recorded, as appropriate.

(Advantages of Particle Measuring Device and Particle Measuring Method According to this Embodiment)

According to the particle measuring device according to this embodiment described above and the particle measuring method using this, first, illumination is performed by the reflected light illuminating device from the upper side of a fine particle, and, in a case where multiple external disturbances having low brightness levels are mainly predicted, as described in each embodiment described above, in a particle image that is acquired by capturing the fine particle using reflected light from the fine particle, particle image processing and measuring can be performed with high accuracy.

Second, according to the particle measuring device according to this embodiment and the particle measuring method using this, the brightness levels of the fine particle, which is the measurement target, can be identified more finely (three types of a bright-color particle, a dark-color particle, and an intermediate-color particle) than the case of each embodiment described above.

Third, according to the particle measuring device according to this embodiment and the particle measuring method using this, the brightness level of a fine particle can be identified with high accuracy regardless of variations in the conditions at the time of imaging the fine particle. Even in a case where the imaging target is the same fine particle having uniform reflectivity, the brightness level may vary between pixels or for each photographing operation. As reasons for such variations in the brightness level, for example, there are drifts or the like in the luminance of the illumination device or the characteristics of an imaging element (for example, a CCD element) of imaging means (camera), the ununiformity of illumination in an imaging space, a difference between the characteristics of CCD elements, and the like, and it is almost impossible to completely prevent the variations in the brightness level in a practical sense.

Thus, in a case where the average brightness level of images of fine particles, which are targets for identifying the brightness levels, at the time of forming an image using illumination (reflected light) emitted from the upper side is close to the brightness level of the background, a pixel area in which a brightness difference between the peripheral edge portion of a fine particle and the background pixel cannot be identified may change in accordance with the variation in the brightness level at the time of forming an image. As an extreme case, in a case where the brightness level of the background changes such that the average brightness level of a fine particle coincide with the brightness level of the background, the fine particle is not recognizable, and, in a case where the brightness level of the background changes in the opposite direction such that there is a difference between the average brightness of a fine particle and the brightness level of the fine particle, the fine particle may be recognized as a particle. In other words, the area of the particle (reflected light image) using the illumination emitted from the upper side changes in accordance with the imaging condition.

Here, generally, since a variation in the area of a particle due to a difference in the imaging condition at the time of performing image processing and measuring of the particle that is imaged using the illumination (transmitted light) emitted from the lower is small, in a case where the brightness level of the particle is identified based on the ratio between the areas of the particle imaged using the illumination emitted from the lower side and the particle imaged using the illumination emitted from the upper side, a determination of the brightness level (bright or dark) of the same particle changes in accordance with the variation in the area of the particle that is imaged by using the illumination emitted from the upper side so as to incur an error in the identification of the brightness level of the particle.

On the other hand, when imaging is performed by using the illumination emitted from the upper side, in a case where there is a large difference between the average brightness level of the image of a fine particle, which is the identification target of the brightness level and the brightness level of the background, an area in which the particle is present is clearer even when there is a variation in the brightness level at the time of imaging, whereby a variation in the area of the particle is small (even when the imaging condition varies more or less, the average brightness level of the particle does not coincide with the brightness level of the background). Accordingly, the error in the identification of the brightness level of the particle according to the variation in the imaging condition is small.

However, even in such a case, in the condition in which the brightness level of the background is one type, a brightness level that is close to the brightness level of the background of this one type may be present depending on the brightness level of the particle.

Thus, in this embodiment, a fine particle that is a measurement target is imaged using two types of backgrounds of the bright background and the dark background, a dark-color particle is identified using the bright background reflected light image, and a bright-color particle is identified using a dark background reflected light image, whereby a large difference between the brightness levels of the background and the fine particle that is an identification target of the brightness level can be secured. Accordingly, in any condition, constantly, the error in the identification of the brightness level of the particle according to a variation in the imaging condition can be small. For example, in FIG. 10, in the bright-background photographing image, a dark-color particle can be fully identified by using the threshold value Tr3(B) that is set to a brightness level that is much lower than the brightness level of the background. In contrast to this, in a dark-background photographing image, a bright particle can be fully identified by using the threshold value Tr3(D) that is set to be much higher than the brightness level of this background.

Fourth Embodiment

Next, a particle measuring device and a particle measuring method according to a fourth embodiment of the present invention will be described, and, mainly, configurations that are different from those of each embodiment described above will be described in detail.
(Particle Measuring Device)

The particle measuring device according to this embodiment has the functions of a reflected light image generating unit, a reflected light particle detecting unit, a reflected light image generating unit, and a particle information calculating unit that are similar to those of the particle measuring device according to the above-described third embodiment. Described in more detail, in the above-described third embodiment, while the bright-background brightness threshold value Tr3(B) is lower than the dark-background brightness threshold value Tr3(d), in this embodiment, the bright-background brightness threshold value is higher than the dark-background brightness threshold value, which is markedly different from the third embodiment. Meanwhile a particle information calculating unit according to this embodiment, similarly to that of the third embodiment, can identify the brightness levels of fine particles, which are measurement targets, as three types including an intermediate-color particle in addition to the bright-color particle and the dark-color particle. Hereinafter, detailed description thereof will be presented.

The reflected light image generating unit according to this embodiment, similarly to that of the second embodiment, first, generates a dark-background reflected light image acquired by imaging fine particles, which are measurement targets, in a state in which the luminance of a transmitted light illuminating device is set by an illumination control device such that the brightness level of the background of the reflected light particle on the reflected light image is lower than a first brightness threshold value (hereinafter, referred to as a "dark-background brightness threshold value Tr4(D)) used for identifying the level of the brightness of a particle.

In addition, the reflected light image generating unit according to this embodiment, similarly to the first embodiment, generates a bright-background reflected light image acquired by imaging fine particles, which are measurement targets, in a state in which the luminance of the transmitted light illuminating device is set by the illumination control device such that the brightness level of the background of the reflected light particle on the reflected light image is higher than a second brightness threshold value (hereinafter, referred to as a "bright-background brightness threshold value Tr4 (B)) used for identifying the level of the brightness of a particle that is a brightness threshold value higher than the dark-background brightness threshold value Tr4(D).

Here, while the dark-background brightness threshold value Tr4(D) and the bright-background brightness threshold value Tr4(B) can be acquired by using a method that is the same as the method of acquiring a "brightness threshold value used for identifying the level of the brightness of a particle" described in the first and second embodiments, in this embodiment, it is important that the dark-background brightness threshold value Tr4(D) is lower than the bright-background brightness threshold value Tr4(B).

In addition, the reflected light particle detecting unit according to this embodiment, first, similarly to the case of the second embodiment, specifies a pixel area in which pixels having high brightness levels are aggregated in the pixel coordinates of the dark-background reflected light image as an area in which the reflected light particle is present and detects the position coordinates of a pixel within an area in which the reflected light particle is present, based on a brightness distribution of a reflected light binarized image that is acquired by binarizing the dark-background reflected light image using the dark-background brightness threshold value Tr4(D).

Furthermore, the reflected light particle detecting unit according to this embodiment, similarly to the case of the first embodiment, specifies a pixel area in which pixels having low brightness levels are aggregated in the pixel coordinates of the bright-background reflected light image as an area in which the reflected light particle is present and detects the position coordinates of a pixel within an area in which the reflected light particle is present, based on a brightness distribution of a bright-background reflected light binarized image that is acquired by binarizing the bright-background reflected light image using the bright-background brightness threshold value Tr4(B).

In other words, in this embodiment, in the dark-background reflected light binarized image, the brightness level of the background is on the lower brightness side, and only a particle having a brightness level that is higher than the dark-background brightness threshold value Tr4(D) is recognized as a reflected light particle, and in the bright-background reflected light binarized image, the brightness level of the background is on the higher brightness side, and only a particle having a brightness level that is lower than the bright-background brightness threshold value Tr4(B) is recognized as a reflected light particle. In addition, the dark-background brightness threshold value Tr4(D) of this embodiment is lower than the dark-background brightness threshold value Tr3(D) of the third embodiment, and the bright-background brightness threshold value Tr4(B) is higher than the bright-background brightness threshold value Tr3(B) of the third embodiment. Accordingly, by performing binarization using such a threshold value, an intermediate-brightness level fine particle that has a brightness level higher than the dark-background brightness threshold value Tr4(D) and lower than the bright-background brightness threshold value Tr4(B) is identified in both the dark-background reflected light binarized image and the bright-background reflected light binarized image.

Thus, the particle information calculating unit according to this embodiment identifies a fine particle corresponding to a transmitted light particle that is associated with the reflected light particle, by using the association processing unit, as a candidate for a bright-color particle having a brightness level that is higher than the dark-background brightness threshold value Tr4(D) and identifies a fine particle corresponding to the transmitted light particle that is associated with the reflected light particle that is present within the bright-background reflected light image as a candidate for a dark-color particle having a brightness level that is lower than the bright-background brightness threshold value Tr4(B). In addition, the particle information calculating unit according to this embodiment identifies a fine particle corresponding to the transmitted light particle that is associated with both the reflected light particle that is present within the dark-background reflected light image and the reflected light particle that is present within the bright-background reflected light image as an intermediate-color particle having an intermediate brightness level between the bright-color particle and the dark-color particle, identifies a particle out of the candidates for a bright-color particle, which has not been identified as an intermediate-color particle, as a bright-color particle, and identifies a particle out of the candidates for a dark-color particle, which has not been identified as an intermediate-color particle, as a dark-color particle.

In other words, in this embodiment, a fine particle corresponding to a transmitted light particle that is associated with a reflected light particle that is present in any dark-background reflected light image is a candidate for a bright-color particle, a fine particle corresponding to a transmitted light particle that is associated with a bright-background reflected light particle that is present within any bright-background reflected image is a candidate for a dark-color particle, and a fine particle corresponding to a transmitted light particle that is associated with the reflected light particle of the dark-background reflected light image and the bright-background reflected light image is an intermediate-color particle. In addition, out of the candidates for a bright-color particle, a particle that has not been identified as the intermediate-color particle is a bright-color particle, and, out of the candidates for a dark-color particle, a particle that has not been identified as the intermediate-color particle is a dark-color particle.

(Particle Measuring Method)

As above, while the particle measuring device according to this embodiment has been described, subsequently, a method of detecting a reflected light particle in the particle measuring method according to this embodiment will be mainly described with reference to FIG. 11. FIG. 11 is an explanatory diagram that illustrates an example of the image processing method using a reflected light image according to this embodiment.

As illustrated in FIG. 11(a), the brightness levels of pixels in the reflected light image are determined by the brightness levels of the fine particles P1, P2, and P3. In other words, since the reflected light image is captured by using reflected light of light emitted toward the substrate 1 or the stage 101 on which the fine particles P1, P2, P3 are sprayed, the brightness levels of the captured images (reflected light particles) of the fine particles on the reflected light image are in correspondence with the brightness levels of the actual fine particles P1, P2, and P3. For example, in a case where the fine particle P1 is a bright-color particle having a high brightness level, the fine particle P2 is an intermediate-color particle having an intermediate brightness level, and the fine particle P3 is a particle having a low brightness level (dark-color particle), in the reflected light image, the brightness level of a pixel corresponding to an area in which the fine particle P1 is present is recognized as a bright color (an area having a high brightness level), the brightness level of the pixel corresponding to an area in which the fine particle P3 is present is recognized as a dark color (an area having a low brightness level), and the brightness level of a pixel corresponding to an area in which the fine particle P2 is present is recognized as an intermediate-color (an area having an intermediate brightness level).

In this embodiment, similarly to the case of the above-described first embodiment, a transmitted light image is generated by imaging a fine particle, which is a measurement target, using transmitted light, and a dark-background reflected light image is generated by imaging a fine particle using reflected light in a condition in which the brightness level of the background is lower than the "brightness threshold value used for identifying the level of the brightness of a particle". In addition, in this embodiment, similarly to the case of the above-described second embodiment, a bright-background reflected light image is generated by imaging a fine particle using reflected light in a condition in which the brightness level of the background is higher than the "brightness threshold value used for identifying the level of the brightness of a particle".

Thereafter, as illustrated in FIG. 11(a), first, a dark-background reflected light image is binarized using the dark-background brightness threshold value Tr4(D), whereby a dark-background reflected light binarized image is generated. As the dark-background brightness threshold value Tr4(D) at this time, for example, the above-described "brightness threshold value used for identifying the level of the brightness of a particle" may be used.

In addition, in this embodiment, a bright-background reflected light image is binarized using the bright-background brightness threshold value Tr4(B), whereby a bright-background reflected light binarized image is generated. As the bright-background brightness threshold value Tr4(B) at this time, for example, the above-described "brightness threshold value used for identifying the level of the brightness of a particle" may be used, and it is necessary that the bright-background brightness threshold value is higher than the dark-background brightness threshold value Tr4(D).

In addition, before the dark-background reflected light image and the bright-background reflected light image are binarized, the variations of the luminance within the image may be corrected by increasing or decreasing the recorded brightness level of the pixel by a correction value that is a function of the two-dimensional position of the pixel, which is the same as the case of each embodiment described above.

The dark-background reflected light binarized image and the bright-background reflected light binarized image acquired as above, as illustrated in FIGS. 11(b) and 11(c), is formed by pixels having high brightness levels (illustrated as a white area) and pixels having low brightness levels (illustrated as areas of slanting lines). Accordingly, based on the connection relation of the binarized brightness levels of pixels that are adjacent to each other in the dark-background reflected light binarized image and the bright-background reflected light binarized image, areas, in which pixels (pixels having high brightness levels in the dark-background reflected light binarized image and pixels having low brightness levels in the bright-background reflected light binarized image) having the same binarized brightness level are continuous, that are independent from the other areas (areas in which pixels having low brightness levels are present in the dark-background reflected light binarized image, and areas in which pixels having high brightness levels are present in the bright-background reflected light binarized image) are specified as the reflected light particle (P1r and P2r in the dark-background reflected light particle and P2r and P3r in the bright-background reflected light particle) that are candidates for a particle. In addition, the position coordinates of the pixels within the specified area in which the reflected light particle Pr is present are detected, the position (for example, the center position) and the size (for example, the area or the diameter) of the reflected light particle Pr are calculated based on the position coordinates, and the position and the size are recorded in a storage device (not illustrated in the figure) disposed in the image processing device or the like.

Next, similarly to the first embodiment, although the process of associating the reflected light particle and the transmitted light particle is performed, at the time of performing the associating process, in this embodiment, a reflected light image is captured in a state in which the brightness level of the background (a peripheral area of a pixel area that is identified as a particle) of the dark-background reflected light image is set to be lower than the "brightness threshold value used for identifying the level of the brightness of a particle". Accordingly, fine particles that are identified as particles on the dark-background reflected light binarized image are particles having brightness levels that are higher than the brightness level of the background. Here, the dark-background brightness threshold value Tr4(D) of this embodiment has a value that is lower than the dark-background brightness threshold value Tr3(D) of the third embodiment. Accordingly, when binarization is performed using the dark-background brightness threshold value Tr4(D), a fine particle that is identified as a particle on the dark-background reflected light binarized image is a particle that corresponds to the intermediate-color fine particle P2 in addition to the bright-color fine particle P1.

On the other hand, a reflected light image is captured in a state in which the brightness level of the background (a peripheral area of a pixel area that is identified as a particle) of the bright or dark-background reflected light image is set to be higher than the "brightness threshold value used for identifying the level of the brightness of a particle". Accordingly, fine particles that are identified as particles on the bright-background reflected light binarized image are particles having brightness levels that are lower than the brightness level of the background. Here, the bright-background brightness threshold value Tr4(B) of this embodiment has a value that is higher than the bright-background brightness threshold value Tr3(B) of the third embodiment. Accordingly, when binarization is performed using the bright-background brightness threshold value Tr4(B), a fine particle that is identified as a particle on the bright-background reflected light binarized image is a particle that corresponds to the intermediate-color fine particle P2 in addition to the dark-color fine particle P3.

As above, an intermediate-color fine particle is identified in both the dark-background reflected light binarized image and the bright-background reflected light binarized image.

Thus, in this embodiment, for example, first, a first association process is performed using the dark-background reflected light binarized image. As a result, in a case where there are transmitted light particles (P1p and P2p illustrated in FIG. 5) that are associated with the reflected light particles (P1r and P2r illustrated in FIG. 11(b)), fine particles (P1 and P2) corresponding to the transmitted light particles (P1p and P2p) are identified as candidates for bright-color particles having brightness levels that are higher (accordingly, higher than the brightness threshold value used for identifying the level of the brightness of a particle) than the dark-background brightness threshold value Tr4(D).

Next, in this embodiment, a second association process is performed using the bright-background reflected light binarized image. As a result, in a case where there are transmitted light particles (P2p and P3p illustrated in FIG. 5) that are associated with the reflected light particles (P2r and P3r illustrated in FIG. 11(c)), fine particles (P2 and P3) corresponding to the transmitted light particles (P2p and P3p) are set as candidates for dark-color particles having brightness levels that are lower (accordingly, lower than the brightness threshold value used for identifying the level of the brightness of a particle) than the bright-background brightness threshold value Tr4(B).

Next, as the results of the above-described first and second association processes, in a case where there is a transmitted light particle (P2p illustrated in FIG. 5) that is associated with both the reflected light particle within the dark-background reflected light binarized image and the reflected light particle within the bright-background reflected light binarized image, a fine particle (P2) corresponding to the transmitted light particle (P2p) is identified as an intermediate-color particle having an intermediate brightness level between the bright-color particle and the dark-color particle (in this embodiment, the brightness level is higher than the dark-background brightness threshold value Tr4(D) and is lower than the bright-background brightness threshold value Tr4(B)).

In addition, as the result of the above-described first association process, out of transmitted light particles that regarded as candidates for a bright-color particle, a particle (P1p illustrated in FIG. 5) that has not been identified as an intermediate-color particle, and, as the result of the second association unit, out of the transmitted light particles regarded as candidates for the dark-color particle, a particle (P3p illustrated in FIG. 5) that has not been identified as an intermediate-color particle is identified as a dark-color particle.

In addition, in a case where there is a reflected light particle that is not associated with any transmitted light particle, the reflected light particle is excluded from the candidate for the captured image of a fine particle P, which is the same as the first embodiment. For example, in FIGS. 11(b) and 11(c), although false reflected light particles, such as Pnd and Pmd, are generated within the reflected light image due to variations in the brightness level of the background, there is no transmitted light particle corresponding to the particles, and accordingly, the particles can be excluded from particles that are finally employed through the particle association process.

Based on the result of the association process as described above, the position and the size of the transmitted light particle are calculated as the position and the size of the fine particle P, and the representative brightness level of the reflected light particle or the transmitted light particle is calculated as the brightness level of the fine particle P. More specifically, the center position and the size (the radius or the area) of the transmitted light particle that is associated with a reflected light particle are calculated as the position and the size of the fine particle P that corresponds to the transmitted light particle, and the representative brightness level of the reflected light particle is calculated as the brightness level of the fine particle P (in the case of this embodiment, the fine particle is the bright-color particle or the dark-color particle). In addition, while the method of calculating the center position and the size of the transmitted light particle that is associated with both the reflected light particle within the dark-background reflected light binarized image and the reflected light particle within the bright-background reflected light binarized image is as described above, the representative brightness of the fine particle P is calculated as an average value of the representative brightness levels of the dark-background reflected light particle and the bright-background reflected light particle (in the case of this embodiment, the fine particle is an intermediate-color particle).

Furthermore, as the information relating to the fine particle P, a volume in a case where the fine particle P is assumed to be a sphere may be calculated based on the particle diameter of the fine particle P acquired in advance and be recorded. In addition, as necessary, for each brightness level of the particle (in the embodiment, for each of the dark-color particle, the bright-color particle, and the intermediate-color particle), the particle size composition ratio, a total volume, a ratio between total volumes of dark-color particles, bright-color particles, and intermediate-color particles, and the like may be calculated and recorded, as appropriate.

(Advantages of Particle Measuring Device and Particle Measuring Method According to this Embodiment)

In the particle measuring device according to this embodiment and the particle measuring method using this described above, there are the same advantages as those of the third embodiments, which have been described above, particularly, and they are advantageous in the following points over the third embodiment. In other words, in a case where there is a large variation (dispersion) in the brightness level of the background within the dark-background image, the method that is the same as the third embodiment is to be applied, it may be considered to set the bright threshold value Tr3(D) to be extremely high so as to reliably exceed a maximum value of the variation in the brightness level of the background. The reason for this is that there is a possibility that the particle may be misrecognized as a bright-color particle when the variation in the brightness level is added to a particle image having the intermediate brightness level. In such a case, similarly, Tr3(B) within the bright-background image needs to be set to be extremely low. As a result, a difference between the brightness levels of Tr3(D) and Tr3(B) is extremely large, and most of particles are classified into an intermediate color, which is not preferable from the viewpoint of the classification of brightness levels. In addition, in a case where a high threshold value Tr3(D) is set as above, even for an original bright-color particle, there are cases where the area of the particle that is recognized as a bright color markedly decreases, and, in the association process for the transmitted light particle, the area of the particle departs from an allowed range, whereby there is a risk that the particle is not recognized as a bright-color particle. This phenomenon is particularly remarkable in a case where a variation in the brightness level is added to the bright-color particle. Accordingly, from such a viewpoint, it is preferable that Tr3(D) is set to a further lower brightness level. Similarly, in a case where a variation in the brightness level of the background within the bright-background image is extremely large, it is preferable that Tr3(B) is set to a further higher brightness level. However, in the third embodiment, there is a restriction of "Tr3(D)>Tr3(B)" for the brightness levels, and such a request cannot be sufficiently satisfied. In addition, in a case where Tr3(D) is set to be low, or Tr3(B) is set to be high, a part of the background image may be frequently recognized as a false particle due to the variation in the brightness. Accordingly, in a case where the variation in the brightness level of the background is extremely large, the method according to the third embodiment is not appropriate.

On the other hand, in this embodiment, it may be set so as to satisfy "Tr3(D)<Tr3(B)", and, even in a case where the variation in the brightness level of the background is extremely large, the above-described problem in which the area of the identified particle decreases due to excessive setting of the threshold value can be avoided. In addition, in this embodiment, since the size of the intermediate-color particle is recognized twice, even when a specific particle is misrecognized as one background image due to addition of a variation in the brightness level or the like, as long as the particle is recognized as a normal particle in the other background image, the error in the determination of a particle can be further limited.

Fifth Embodiment

Next, a particle measuring device and a particle measuring method according to a fifth embodiment of the present invention will be described, and, mainly, configurations that are different from those of each embodiment described above will be described in detail.

In the particle measuring device and the particle measuring method according to this embodiment, the brightness threshold values used for the binarization in the above-described third embodiment are configured as not two types including the dark-background brightness threshold value and the bright-background threshold value but three or more types.

Basically, this embodiment is acquired by changing the second embodiment as multi-stage identification of brightness levels. In other words, initially a determination of a bright-color particle is performed with the transmitted light illumination and luminance and a brightness threshold value Tr2 corresponding to this luminance as the highest brightness conditions, in the same reflected light illumination and luminance conditions, then the transmitted light illumination and luminance and the brightness threshold value Tr2 are sequentially decreased for a bright-color particle and a transmitted light particle that has not been identified, and identification of brightness particles is performed for each time, whereby the representative brightness of individual brightness level of the particle group identified for each illumination and luminance step is associated as the brightness level (for example, the brightness threshold value) corresponding to the luminance step.

The illumination and luminance step is set in advance such that the brightness level of the background at the time of photographing using the reflected light has a predetermined value. For example, each illumination and luminance step may be set such that corresponding brightness levels of the backgrounds are equally spaced. Similarly, the brightness threshold values corresponding to each illumination and luminance step may be set to be equally spaced. However, this threshold value needs to be set to be at least higher than the brightness level of the background in the illumination and luminance step. For example, in a case where a CCD camera having 256 brightness harmony is used as the particle detecting unit (brightness 1 (black) to brightness 256 (white)), it may be configured such that the background brightness of the first step is brightness 192 and a brightness threshold value is 224, and, at the second step and thereafter, the background brightness and the brightness threshold value are decreased by a brightness difference of 64 each time.

Sixth Embodiment

Next, a particle measuring device and a particle measuring method according to a sixth embodiment of the present invention will be described, and, mainly, configurations that are different from those of each embodiment described above will be described in detail.
(Particle Measuring Device)

The particle measuring device according to this embodiment is different from the above-described particle measuring device 100 according to the first embodiment in the functions of an illumination control device, a reflected light image generating unit, a reflected light particle detecting unit, an association processing unit, and a particle information calculating unit.

Specifically, in the illumination control device according to this embodiment, the brightness level of the background of the reflected light particle on the reflected light image is higher than a brightness threshold value that is used for identifying the level of the brightness of a particle, and the first luminance to the N-th luminance that satisfy the relation of "first brightness level<second brightness level< . . . <N-th brightness (here, N is a natural number) can be set to the transmitted light illuminating device.

In addition, the reflected light image generating unit according to this embodiment generates the first to N-th reflected light images (the brightness levels of the backgrounds satisfy "first reflected light image<second reflected light image< . . . <N-th reflected light image) in a state in which the luminance of the transmitted light illuminating device is set to the first luminance to the N-th luminance.

The reflected light particle detecting unit according to this embodiment specifies a pixel area in which pixels having high brightness levels are aggregated in the pixel coordinates of the first to N-th reflected light binarized images as an area in which a reflected light particle is present and detects the position coordinates of a pixel located within the area in which the reflected light particle is present, based on a bright distribution of images (first to N-th reflected light binarized images) acquired by binarizing the first to N-th reflected light images using a brightness threshold value used for identifying the level of the brightness of a particle.

In addition, the association processing unit according to this embodiment compares the position and the size of the reflected light particle detected in the n-th (here, n=1 to N) reflected light image with the positions and the sizes of the transmitted light particles (in the case of n=1, all the above-described transmitted light particles) that are not associated with the reflected light particle detected in the (n−1)-th or prior reflected light images and associates a transmitted light particle and a reflected light particle having differences in the position and the sizes are within predetermined ranges with each other. For example, the association process with reflected light particles detected in the second to N-th reflected light images is not performed for the transmitted light particle that has been already associated with the reflected light particle detected in the first reflected light image.

Furthermore, the particle information calculating unit according to this embodiment identifies the brightness levels of fine particles corresponding to the transmitted light particles associated with the reflected light particles that are present within the first to N-th reflected light images as first to N-th brightness levels. For example, the brightness level of a fine particle corresponding to the transmitted light particle associated with the reflected light particle that is present within the first reflected light image is identified as a first brightness level, the brightness level of a fine particle corresponding to the transmitted light particle associated with the reflected light particle that is present within the second reflected light image is identified as a second brightness level, and such a process is performed for the other fine particles, whereby the brightness levels of fine particles corresponding to the transmitted light particles associated with the reflected light particles that are present within all the reflected light images including the first to N-th reflected light images are identified. The brightness levels at this time satisfy "first brightness level<second brightness level< . . . <N-th brightness level". In addition, the particle information calculating unit according to this embodiment identifies a fine particle corresponding to the transmitted light particle that is not associated with any reflected light particle as a particle having the highest brightness level.
(Particle Measuring Method)

As above, while the particle measuring device according to this embodiment has been described, subsequently, a method of detecting a reflected light particle in the particle measuring method according to this embodiment will be mainly described.

In this embodiment, similarly to the case of the above-described first embodiment, fine particles that are measurement targets are imaged using transmitted light, whereby transmitted light images are generated.

Thereafter, similarly to the above-described first embodiment, fine particles are imaged using reflected light in a condition in which the brightness level of the background is lower than the "brightness threshold value used for identifying the level of brightness of a particle", whereby reflected light images are generated. At this time, the fine particles are imaged so as to generate reflected light images while the brightness level of the background is changed, whereby the fine particles are imaged with backgrounds of total N types of brightness levels. In this way, the first to N-th reflected light images captured with the first to N-th background brightness levels (first background brightness level<second background brightness level< . . . <N-th background brightness level). Accordingly, the first reflected light image is an image that is captured with a background having a lowest brightness level, and the N-th reflected image is an image that is captured with a background having a highest brightness level.

Thereafter, the first to N-th reflected images are binarized using the "threshold value used for identifying the level of brightness of a particle", whereby the first to N-th reflected light binarized images are generated.

In addition, before the each reflected light image is binarized, the variations in the luminance within the image may be corrected by increasing or decreasing the recorded brightness level of the pixel by a correction value that is a function of the two-dimensional position of the pixel, which is the same as the case of each embodiment described above.

The first to N-th reflected light binarized images acquired as above is formed by pixels having high brightness levels and pixels having low brightness levels. Accordingly, based on the connection relation of the binarized brightness levels of pixels that are adjacent to each other in the first to N-th reflected light binarized images, areas, in which pixels having the same binarized brightness level (in this embodiment, pixels having low brightness levels) are continuous, that are independent from the other areas (areas in which pixels having high brightness levels are present in this embodiment) are specified as reflected light particles that are candidates for particles. In addition, the position coordinates of the pixels within the specified area in which the reflected light particle is present are detected, the position (for example, the center position) and the size (for example, the area or the diameter) of the reflected light particle are calculated based on the position coordinates, and the position and the size are recorded in a storage device (not illustrated in the figure) disposed in the image processing device or the like.

Next, similarly to the first embodiment, although the process of associating the reflected light particle and the transmitted light particle is performed, at the time of performing the associating process, in this embodiment, the position and the size of the reflected light particle detected in the n-th (here, n=1 to N) reflected light image are compared with the position and the size of the transmitted light particles (in the case of n=1, all the transmitted light particles) that are not associated with reflected light particles detected in the (n−1)-th and prior reflected light images, and the transmitted light particle and the reflected light particle having differences in the position and the size that are within predetermined ranges are associated with each other.

Described in more detail, first, similarly to the case of the first embodiment, a first association process is performed between a reflected light particle (first reflected light particle) detected in the first reflected light image and the transmitted light particle, that is captured with a first background brightness level. As a result, in a case where there is a transmitted light particle that is associated with the first reflected light particle, a fine particle corresponding to the transmitted light particle is identified as a particle having the first brightness level (darkest color). Next, a second association process is performed between a reflected light particle (second reflected light particle) detected in the second reflected light image and the transmitted light particle, that is captured with a second background brightness level. At the time of performing the second association process, the transmitted light particle that has already been associated with the first reflected light particle is excluded from the target of the second association process. Similarly to the first association process, in a case where there is a transmitted light particle that is associated with the second reflected light particle, the fine particle corresponding to the transmitted light particle is identified as a particle having the second brightness level (second darkest color). Similarly, up to the N-th association process is performed.

In this way, the brightness levels of fine particles corresponding to the transmitted light particles associated with the reflected light particles that are present within the first to N-th reflected light images are identified as first to N-th brightness levels. The brightness levels at this time satisfy "first brightness level<second brightness level< . . . <N-th brightness level". In addition, the particle information calculating unit according to this embodiment identifies a fine particle corresponding to the transmitted light particle that is not associated with any reflected light particle as a particle having the highest brightness level.

In addition, in a case where there is a reflected light particle that is not associated with any transmitted light particle, the reflected light particle is excluded from the candidates for the captured image of a fine particle that is a measurement target, which is similar to the first embodiment.

Based on the result of the association process performed as described above, the position and the size of the transmitted light particle are calculated as the position and the size of a fine particle that is a measurement target, and the representative brightness level of the reflected light particle or the transmitted light particle is calculated as the brightness level of the fine particle. More specifically, the center position and the size (the radius or the area) of the transmitted light particle that is associated with a reflected light particle are calculated as the position and the size of the fine particle that corresponds to the transmitted light particle, and the representative brightness level of the reflected light particle is calculated as the brightness level of the fine particle. In addition, while the method of calculating the center position and the size of the transmitted light particle that is not associated with any reflected light particle is as described above, the brightness level of the fine particle is calculated as the representative brightness level of the transmitted light particle.

Furthermore, as the information relating to the fine particle that is the measurement target, a volume in a case where the fine particle is assumed to be a sphere may be calculated based on the particle diameter of the fine particle acquired in advance and be recorded. In addition, as necessary, for each brightness level of the particle (in this embodiment, for each of the first to N-th brightness-level particles), the particle size composition ratio, a total volume, a ratio between the first to N-th particles, and the like may be calculated and recorded, as appropriate.

(Advantages of Particle Measuring Device and Particle Measuring Method According to this Embodiment)

According to the particle measuring device according to this embodiment described above and the particle measuring method using this, first, illumination is performed by the reflected light illuminating device from the upper side of a fine particle, which is the measurement target, and in a case where multiple external disturbances having low brightness levels and external disturbance having high brightness are mainly predicted, as described in each embodiment described above, in a particle image that is acquired by capturing the fine particle using reflected light from the fine particle, particle image processing and measuring can be performed with high accuracy.

Second, according to the particle measuring device according to this embodiment and the particle measuring method using this, the brightness levels of the fine particle, which is the measurement target, can be identified as not two types but multiple levels of brightness. In addition, in this embodiment, since the reflected light image is binarized, even in a case where a highlight is present in a pixel located in an area corresponding to the fine particle, the pixel is excluded from pixels used for determining the brightness level, and accordingly, the original representative brightness level of the fine particle that is the measurement target can be determined with relatively high accuracy.

[Measurement Target According to Present Invention]

While the measurement target according to the present invention including the above-described embodiments is a fine particle group including fine particles having various brightness levels and is not particularly limited as long as the brightness level of the fine particles are needed to be identified, there are the following examples as representative examples.

First Example

As a first example of the measurement target in the particle measuring device and the particle measuring method according to the present invention, there are a high-purity alumina powders.

Although the high-purity alumina powders are white particles having a particle diameter of about 10 to 1000 μm in generally, particles (impurity particles) containing impurities in the high-purity alumina powders exhibit a non-white color. Since there is a difference between the brightness levels of the particles, the high-purity alumina powers and impurity particles can be identified based on the brightness levels of the particles.

Accordingly, in order to check the content of impurities in a high-purity alumina power product, by using the particle measuring device and the particle measuring method according to the present invention, the high-purity alumina powers and the impurity particles are identified based on the brightness levels of the particles, and it is possible to acquire particle component ratio between the high-purity alumina powers and the impurity particles based on the result of the identification.

Second Example

As a second example of the measurement target in the particle measuring device and the particle measuring method according to the present invention, there are falling dusts that are originated from an iron manufacturing plant according to a blast furnace method.

Such falling dusts cause problems such as staining a vehicle that travels inside the iron manufacturing plant, and a countermeasure for such problems is necessary. Accordingly, a technique for specifying a generation source of falling dusts that are collected at a specific place is necessary, and, as a technique for specifying the generation source of the falling dusts, it is important to specify the dust type of the collected falling dusts.

Here, the falling dusts represent particles each having a relatively long diameter (φ10 μm or more as a whole) that can subside in the air on the average out of solid particles that float in the air. In addition, the "dust type" according to the present invention is not particularly limited and represents the types of dusts that are classified by the generation sources, composing components, or the like of the above-described falling dusts. For example, in a case where the dusts are classified by the generation sources, the dust types are classified into dusts originated from an iron ore that is generated from a raw material yard of the iron ore, dusts originated from coal that are generated from a raw material yard of coal, dusts originated from a blast furnace slag that are generated from a blast furnace, dusts originated from a converter furnace that are generated from a converter slag, and the like.

According to such a classification, as the dust types of falling dusts originated from an iron manufacturing plant according to a blast furnace method, mainly, there are (1) coal-based dusts such as coal, cokes, and the like having carbon in common as a main component, (2) iron-based dusts such as iron ore, sintered ore, a brown iron oxide (for example, steelmaking dusts) that contain an iron oxide in common as a main component, (3) blast furnace slag-based dusts such as granulated blast furnace slag or air-cooled blast furnace slag that contain silica oxide and calcium oxide in common as main components and have a common process for separating impurities from a melt raw material as liquid or solid, and (4) steelmaking slag-based dusts such as converter slag or molten iron preliminary processing slag that contain silicon oxide, calcium oxide, and iron oxide in common as main components and have common processes owing to the separation of impurities from a melt raw material as liquid or solid. The dust types that are falling dusts in an iron manufacturing plant according to the blast furnace method includes the coal-based dusts, iron-based dusts, blast furnace slag-based dusts, and steelmaking slag-based dusts, which can cover almost everything.

In order to specify the dust type of the above-described falling dusts originated from the iron manufacturing plant, the dusts need to be separated for each dust type, and the particle measuring device and the particle measuring method according to the present invention are effective as the method of separating the dusts. Out of the above-described four types of dusts, since the iron-based dusts and the coal-based dusts are black particles (dark particles) having low brightness levels, and the granulated blast furnace slag-based dusts and the steelmaking slag-based dusts are white particles (bright-color particles) having high brightness levels, by identifying the level of the brightness of individual dust particles using the particle measuring device or the particle measuring method according to the present invention, a fine particle group that is formed from the iron-based dusts and the coal-based dusts and a fine particle group that is formed from the granulated blast furnace slag-based dusts and the steelmaking slag-based dusts can be discriminated from each other.

Generally, since the iron-based dusts or the steelmaking slag-based dusts are fine particles that have ferromagnetism or strong paramagnetism (for example, magnetized by a magnet having a magnetic flux density of about 0.1 T to 0.4T), and the coal-based dusts and the granulated blast furnace-based dusts are fine particles having no ferromagnetism or strong paramagnetism, and, by sorting such fine particles based on a magnetic force by using a magnet having a predetermined magnetic flux density, a determination of the iron-based dusts and the coal-based dusts and a determination of the steelmaking slag-based dusts and the granulated blast furnace slag-based dusts can be made.

As above, while preferred embodiments of the present invention have been described in detail with reference to the accompanying drawings, the present invention is not limited to such examples. It is apparent that those skilled in the art of a field to which the present invention belongs can consider various changed examples or modified examples within the scope of the technical concept described in the claims, and it is understood that these, naturally, also belong to the technical scope of the present invention.

For example, in a case where there is a small external disturbance for the reflected light particles, and the brightness levels of all the particles that are measurement targets are greatly different from the brightness level of the background, the identification of particles may be performed by directly using the captured image (reflected light image) without performing a binarization process in the image processing (the identification can be performed by using a particle image processing function of software that is available in the market. At this time, an average value of the brightness levels of pixels located in an area in which a reflected particle corresponding to the pixel coordinates of the transmitted light particle is present may be calculated as the brightness level of the fine particle corresponding to the transmitted light particle.

In addition, although the particle measuring method according to each embodiment described above is performed using the imaging device 110 or the image processing device 130 illustrated in FIG. 2, the particle measuring method according to the present invention is not limited to such examples, and it is not necessary to use the imaging device 110 or the image processing device 130. For example, a transmitted light image and a reflected light image that are photographed with photographing conditions such as illumination manually set are developed into a photograph, this reflected light photograph is covered with a tracing paper having predetermined transparency, the contours of particles that can be identified are traced with a pen or the like as bright-color particles, the tracing paper and the transmitted light photograph are superimposed, after the correspondence between particles disposed on the tracing paper and particles disposed on the transmitted light photograph is taken through visual observation, the position of the particle is recorded for each particle using a ruler or the like, the transmitted light photograph is covered with tracing graph paper, and the area of each particle is acquired based on the number of squares occupied by the particle and is recorded, whereby an operation that is similar to a case where the imaging device 110 or the image processing device 130 is used can be realized.

EXAMPLES

Next, the present invention will be described more specifically with reference to examples.

Example 1

Preparation of Analysis Sample

First, as standard samples of which dust types are known, iron ore, coal, granulated blast furnace slag, and converter slag were prepared, 500 μg of each sample was scooped using a spoon, the sample was scattered on first transparent cover glass for which a white alumite treatment had been performed, and each particle was expanded on the transparent cover glass so as not to overlap each other by using a stainless spatula. The expanded particle group was present in the range of about 10 mm in the diameter.

Next, a cylindrical electromagnet having a diameter of 10 mm, which is available in the market, was disposed such that the center axis is in the vertical direction, and a current supplied to the electromagnet was adjusted such that an average magnetic flux density on eh tip end face (lower end face) of the magnet is 0.3 T. In this state, the electromagnet was vertically lowered from the upper side of particles scattered on the transparent cover glass so as to be in contact with the particles while being maintained by an operator using hands. After the electromagnet was stopped for one second in this state, the electromagnet was lifted to the upper side so as to move the magnetized particles together with the electromagnet, and the electromagnet was vertically lowered from the upper side on a second transparent cover glass for which a white alumite treatment had been performed, whereby the electromagnet was placed on the second transparent cover glass. Thereafter, after an element current is supplied to the electromagnet, the supply of the current to the electromagnet was stopped, and the electromagnet was lifter to the upper side so as to be separated from the second transparent cover glass.

Regarding the dimensions of the first transparent cover glass and the second transparent cover glass, which were used, the size was 30 mm×30 mm, and the thickness was 3 mm. As a method of demagnetizing the electromagnet, an electromagnet demagnetization controller that is available in the market was used.

As a result of the above-described operation, particles remaining on the first transparent cover glass were used as samples of non-magnetized falling dusts (falling dusts that are not magnetized by the magnet), and particles remaining on the second transparent cover glass were used as samples of magnetized falling dusts (falling dusts that are magnetized by the magnet).

<Imaging Fine Particles>

Next, a ring-shaped white LED illumination (hereinafter, referred to as a "reflected light illuminating device"), which is available in the market, was installed to the lens barrel of a three-lens type stereoscopic microscope (objective lens power: 0.5×), and a white LED planar array illumination (hereinafter, referred to as a "transmitted light illuminating device") that is available in the market was disposed on the lower side of the stage. In addition, a monochrome digital camera (CCD 600 million pixels; each pixel size of 3 μm) that is available in the market was mounted on a camera mount opening. Furthermore, a circular deflection filter plate was disposed between the reflected light illuminating device and the lens, and the stage, and sheet metal working was performed for an iron plate such that the upper end was brought into contact with the lower face of the stage, and a light shielding plate was arranged so as to cover the periphery of the transmitted light illuminating device. In addition, as an illumination control device that controls the reflected light illuminating device and the transmitted light illuminating device, a device, which is available in the market, that can independently turn on or off the reflected light illuminating device and the transmitted light illuminating device in accordance with external signals was used. Thereafter, a microscope slide glass was arranged on the stage formed from a transparent float glass plate (a thickness of 10 mm) as a substrate, and, the non-magnetization falling dust samples and the magnetizing falling dust samples acquired as above were scattered on the substrate, the samples are sequentially photographed with the illumination condition set to be the same, and the diaphragm and the exposure of the camera set to the same conditions, whereby a transmitted light image and a reflected light image were acquired for each of the magnetization dust and the non-magnetization dust.

The imaging conditions for the transmitted light image and the reflected light image were as below. First, as the imaging conditions of the transmitted light image, the reflected light illuminating device was turned off, and the luminance of the illumination emitted from the transmitted light illuminating device was set such that an average brightness level of the background on the transmitted light image was 120 (brightness level has 256 gray scales, a comma value of 1.5, and the definition of the brightness level is as below), and the magnetization dusts and the non-magnetization dusts were imaged. In addition, as the imaging conditions of the reflected light image, the luminance of illumination emitted from the reflected light illuminating device was set such that an average brightness level was 60 on the image when a color sample having a munsell value of N4.0 was photographed, and the luminance of illumination emitted from the transmitted light illumination device was set to the same condition as that of a case where the transmitted light image was captured. At this time, a brightness threshold value used for identifying the level of brightness of a particle was set to 70.

In addition, the magnification of the microscope was adjusted such that the real size of the particle, which is a measurement target, was imaged on the CCD element of the camera with the same dimensions. In addition, a target particle that is recognized by the microscope was a falling dust, the particles were rough, and accordingly, a particle having a size of ϕ10 μm or more was used. Furthermore, in this embodiment, the size of the particle corresponds to 9 pixels or more of the CCD.

<Image Processing>

For the magnetization dust image and the non-magnetization dust image acquired as described as above, particle image processing and measuring was performed by using Image-Pro Plus (registered trademark) Ver. 5 that is a particle image processing software available in the market. At this time, as the measurement targets, the center position of each particle, an equivalent circle diameter of each particle, and an average brightness level of each particle (an average value of brightness levels of pixels that are present in the pixel area that is recognized as a particle) were set.

More specifically, by using the technique of the above-described first embodiment according to the present invention, transmitted light particles and reflected light particles were detected, and the process of associating the transmitted light particles and the reflected light particles, which had been detected, was performed. In this association process (process of associating), a limit distance for a distance between the center positions of the transmitted light particle and the reflected light particle was set to 10 μm, which is a length corresponding to 30% of the diameter of the transmitted light particle to be compared, and the limit ratio range of the area ratios between the transmitted light particle and the reflected light particle was set to 0.7.

The process of associating the transmitted light particle and the reflected light particle was performed under the above-described conditions, and the particles placed within the transmitted light image were identified as bright-color particles and dark-color particles for each magnetization dust and non-magnetization dust. In addition, based on the result of the association process, the center position, the average brightness level, and the equivalent circle diameter of each particle were calculated, and the calculation result was recorded.

Furthermore, by using the equivalent circle diameter of each particle, which has been calculated as described above, the particles were classified for particle sizes of which boundary values were determined in advance, and the particle composition ratio for each particle size was acquired for each brightness class (the dark-color particle and the bright-color particle).

The dust characteristics of standard samples acquired by the above-described operations were as represented in the following Table 1.

TABLE 1

Dust Characteristics of Standard Samples (particle composition ratio [%])

| | magnetization and dark color | magnetization and bright color | non-magnetization and dark color | non-magnetization and bright color |
|---|---|---|---|---|
| iron ore | 90 | 5 | 4 | 1 |
| coal | 5 | 2 | 91 | 2 |
| granulated blast furnace slag | 1 | 1 | 8 | 90 |
| converter slag | 3 | 8.5 | 2 | 10 |

In addition, among the standard samples represented in Table 1, an example in which the particle composition ratio of iron ore (magnetization dark color particle) for each particle size was acquired will be represented below.

Iron Ore
<φ30 μm: 20%
<φ100 μm: 70%
≥φ100 μm: 10%

<Analysis of Collected Falling Dusts>

Next, in a site of an iron manufacturing plant according to a blast furnace method, falling dusts were collected for one week using a deposit gauge that is available in the market, and falling dusts of 100 mg were acquired. After the falling dusts were naturally dried indoors for three days, 500 μg of the total falling dusts were processed using the same method as that for the standard samples described above, whereby the dust characteristics of the falling dusts were acquired. The result is represented in Table 2 represented below.

TABLE 2

Dust Characteristics of Collected Falling Dusts (particle composition ratio [%])

| | magnetization and dark color | magnetization and bright color | non-magnetization and dark color | non-magnetization and bright color |
|---|---|---|---|---|
| falling dust sample | 85 | 7 | 6 | 2 |

By comparing the dust characteristics of the falling dust samples collected as described above and the dust characteristics of standard samples represented in Table 1 represented above, the falling dust sample is mainly configured by magnetization dark-color particles, and accordingly, the collected falling dusts were specified as iron ore that is configured mainly by magnetization dark-color particles.

The particle composition ratios of the collected falling dust samples for each particle size were as below.
Falling Dusts
<φ30 μm: 50%
<φ100 μm: 45%
≥φ100 μm: 5%

When this result is reviewed, although the particle size distribution is different from the particle size distribution of iron ore represented above, from this result, a place at which the falling dusts as samples in this example were collected was departed away from the dust emission source (a yard on which the iron ore is stored or the like), and it can be estimated that particles having large diameters fell on the way until the collection place was reached, and the composition ratio of particles having large diameters decreased.

Example 2

In this example, as particles to be identified, high-purity alumina powers (including impurity particles) were used and were imaged by using the imaging device that is the same as that of Example 1, and transmitted light images and the reflected light images were acquired for the high-purity alumina powers.

The imaging conditions for the transmitted light image and the reflected light image were as below. First, as the imaging conditions of the transmitted light image, the reflected light illuminating device was turned off, and the luminance of the illumination emitted from the transmitted light illuminating device was set such that an average brightness level of the background on the transmitted light image was 120, and the high-purity alumina powders were imaged. In addition, as the imaging conditions of the reflected light image, the luminance of illumination emitted from the reflected light illuminating device was set such that an average brightness level was 160 on the image when a color sample having a munsell value of N7.0 was photographed, and the high-purity alumina powers were imaged with the luminance of illumination emitted from the transmitted light illumination device turned off. At this time, a brightness threshold value used for identifying the level of brightness of a particle was set to 130.

For the transmitted light image and the reflected light image of the high-purity alumina powers acquire as described above, particle image processing and measuring was performed by using Image-Pro Plus (registered trademark) Ver. 5 that is a particle image processing software available in the market. At this time, as the measurement targets, the center position of each particle, an equivalent circle diameter of each particle, and an average brightness level of each particle (an average value of brightness levels of pixels that are present in the pixel area that is recognized as a particle) were set.

More specifically, by using the technique of the above-described second embodiment according to the present invention, transmitted light particles and reflected light particles were detected, and the process of associating the transmitted light particles and the reflected light particles, which had been detected, was performed. In this association process, a limit distance for a distance between the center positions of the transmitted light particle and the reflected light particle was set to 10 μm, which is a length corresponding to 30% of the diameter of the transmitted light particle to be compared, and the limit ratio range of the area ratios between the transmitted light particle and the reflected light particle was set to 0.7.

The process of associating the transmitted light particle and the reflected light particle was performed under the above-described conditions, and the particles placed within the transmitted light image were identified as bright-color particles and dark-color particles for the high-purity alumina powers. In addition, based on the result of the association process, the center position, the average brightness level, and the equivalent circle diameter of each particle were calculated, and the calculation result was recorded.

Furthermore, by using the equivalent circle diameter of each pixel, which has been calculated as described above, the particles were classified for particle sizes of which boundary values were determined in advance, and the particle composition ratio for each particle size was acquired for each brightness class (the dark-color particle and the bright-color particle).

As a result, the average diameter of the imaged high-purity alumina powers was 30 μm, the standard deviation of the particle diameters was 8 μm, and the brightness levels of a total of 2,600 particles were identified. Among such particles, as the ratio of numbers, particles of 0.5% were identified as dark particles. From this, it can be understood that, in the high-purity alumina powers used in Example 2, as a ratio of numbers, impurities of 0.5% was included.

Example 3

In this Example 3, the same samples as those of Example 2 were used, and as the method of identifying bright-color particles, the same method as that of Example 2 was used. Regarding the imaging as a method of identifying dark-color particles, the luminance was set such that an average brightness level at the time of photographing a color sample having a munsell value of N7.0 was 200, and a bright-background image was acquired. In addition, dark-color particles were identified using the same method as that of Embodiment 1 with the brightness threshold value set as 90. The limit distance between the center positions of the transmitted light particle and the reflected light particle and the limit area ratio range used at that time were the same as those of Example 2.

In addition, as the method of associating particles together, the method of Embodiment 3 was used.

As a result, as the ratio of numbers, dark particles of 0.2% and intermediate-color particles of 0.3% were identified (the remaining were bright-color particles). From this result, it could be understood that a plurality of types of impurities having mutually different brightness levels were included.

Example 4

In this Example 4, the same samples as those of Example 3 were used, and the same photographing as that of Example 3 was performed, and particles were identified using the method of Embodiment 4. As the brightness threshold values, a brightness level of 90 was used for a dark-background image, and a brightness level of 160 was used for a bright-background image. As a result, as the ratio of numbers, dark-color particles of 0.2% and intermediate-color particles of 0.3% were identified (remaining's are bright-color particles).

INDUSTRIAL APPLICABILITY

According to the present invention, based on a transmitted light image acquired by imaging an opaque fine particle group using transmitted light and a reflected light image acquired by imaging an opaque fine particle group using reflected light, by associating transmitted light particles present in the transmitted light image and reflected light particles present in the reflected light image with each other using a predetermined method, various characteristics (the position, the size, the brightness level, and the like) of individual particles out of a fine particle group can be simultaneously measured.

REFERENCE SIGNS LIST

1 substrate
100 particle measuring device
101 stage
110 imaging device
111 imaging element
113 transmitted light image generating unit
115 reflected light image generating unit
119 lens
121 reflected light illuminating device
123 transmitted light illuminating device
125 illumination control device
127 light shielding plate
130 image processing device
131 transmitted light particle detecting unit
133 transmitted light particle information calculating unit
135 reflected light particle detecting unit
137 reflected light particle information calculating unit
139 association processing unit
141 particle information calculating unit
P (P1, P2, and P3) fine particles as measurement targets
P1$p$, P2$p$, and P3$p$ transmitted light particle
P1$r$, P2$r$, and P3R reflected light particle

The invention claimed is:
1. A particle measuring device comprising:
a stage which is a transparent flat plate and on which a transparent substrate having an opaque fine particle sprayed thereon is placed or the fine particle is directly sprayed;

a reflected light illuminating device that is disposed on a placement face side of the stage and emits first light having a predetermined device light emitting face luminance toward the stage;

a transmitted light illuminating device that is disposed on a side of the stage that is opposite to the placement face and emits second light having predetermined device light emitting face luminance toward the stage;

an illumination control circuit that individually controls the device light emitting face luminance of the first light and the device light emitting face luminance of the second light;

an imaging device that includes a transmitted light image generating circuit that generates a transmitted light image acquired by imaging the fine particle in a state being controlled by the illumination control circuit such that the device light emitting face luminance of the second light is predetermined luminance other than zero, and the device light emitting face luminance of the first light is zero and a reflected light image generating circuit that generates a reflected light image acquired by imaging the fine particle in a state being controlled by the illumination control circuit such that the device light emitting face luminance of the second light is predetermined luminance set in accordance with one, two or more conditions and the device light emitting face luminance of the first light is predetermined luminance other than zero, and is disposed on the placement face side with respect to the stage; and an image processing device that, by comparing positions and sizes of one, two, or more transmitted light particles that are identified as candidates for a captured image of the fine particle within the transmitted light image and positions and sizes of one, two, or more reflected light particles that are identified as candidates for a captured image of the fine particle within the reflected light image, associates the transmitted light particle and the reflected light particle having a difference between the positions and the sizes within a predetermined range, calculates the position and the size of the transmitted light particle as a position and a size of the fine particle, and calculates a representative brightness level of the reflected light particles or the transmitted light particles as a brightness level of the fine particle, based on a result of the association, wherein the representative brightness level represents a whole pixel area which is identified as the particle, and the representative brightness level is an average value of brightness of each of pixels within the pixel area, a median value of the brightness of each of the pixels, an average value of the brightness of the pixels within the pixel area from which a pixel having a maximum brightness level and a pixel having a lowest brightness level are eliminated, or an average value of the brightness of the pixels within the pixel area from which a pixel within a peripheral edge portion of the pixel area, and wherein the image processing device includes:

a transmitted light particle detecting circuit that specifies a pixel area in which pixels having brightness levels lower than a predetermined brightness level are aggregated in pixel coordinates of the transmitted light image as an area in which the transmitted light particle is present based on an image brightness distribution that is acquired by binarizing the transmitted light image using a predetermined brightness threshold value and detects position coordinates of a pixel within the area in which the transmitted light particle is present;

a transmitted light particle information calculating circuit that calculates at least the position and the size of the transmitted light particle based on a detection result of the transmitted light particle detecting circuit;

a reflected light particle detecting circuit that specifies a pixel area in which pixels each having a brightness level difference from a peripheral pixel that is a predetermined value or more are aggregated in pixel coordinates of the reflected light image as an area in which the reflected light particle is present based on a brightness distribution of the reflected light image and detects position coordinates of a pixel within the area in which the reflected light particle is present;

a reflected light particle information calculating circuit that calculates at least the position and the size of the reflected light particle based on a detection result acquired by the reflected light particle detecting circuit;

an association processing circuit that compares the position and the size of the reflected light particle with the positions and the sizes of all the transmitted light particles based on a calculation result of the transmitted light particle information calculating circuit and a calculation result of the reflected light particle information calculating circuit, associates the transmitted light particle and the reflected light particle having differences in the position and the size that are within predetermined ranges with each other, and exclude the reflected light particle that is not associated with any one of the transmitted light particles from a candidate for a captured image of the fine particle; and a particle information calculating circuit that calculates the position and the size of the transmitted light particle as the position and the size of the fine particle, calculates the representative brightness level of the reflected light particle that is associated with the transmitted light particle as a brightness level of the fine particle, and calculates the brightness level of the transmitted light particle that is not associated with any one of the reflected light particles as a predetermined brightness level.

2. The particle measuring device according to claim 1, wherein the reflected light image generating circuit generates the reflected light image in a state in which the device light emitting face luminance of the second light is set by the illumination control circuit such that the brightness level of a background of the reflected light particle on the reflected light image is higher than a brightness threshold value used for identifying a level of the brightness of a particle, wherein the reflected light particle detecting circuit specifies a pixel area in which pixels having brightness levels lower than a predetermined brightness level are aggregated in the pixel coordinates of the reflected light image as an area in which the reflected light particle is present based on a brightness distribution of an image that is acquired by binarizing the reflected light image using a brightness threshold value used for identifying the level of the brightness of the particle and detects position coordinates of the pixel located within the area in which the reflected light particle is present, and wherein the particle information calculating circuit identifies the fine particle corresponding to the transmitted light particle that is associated with the reflected light particle as a dark-color particle having a brightness lower than a brightness threshold value used for identifying the level of brightness of the particle and identifies the fine particle corresponding to the transmitted light particle that is not associated with any reflected particle as a bright-color particle having a brightness level higher than the brightness threshold value used for identifying the level of the brightness of the particle.

3. The particle measuring device according claim 2, wherein the fine particle is a falling dust that is originated from an iron manufacturing plant according to a blast furnace method.

4. The particle measuring device according to claim 2,
wherein the transmitted light particle information calculating circuit additionally calculates a diameter of the transmitted light particle, and
wherein the particle information calculating circuit additionally calculates the diameter of the transmitted light particle as a particle diameter of the fine particle.

5. The particle measuring device according to claim 1,
wherein the reflected light image generating circuit generates the reflected light image in a state in which the device light emitting face luminance of the second light is set by the illumination control circuit such that the brightness level of a background of the reflected light particle on the reflected light image is lower than a brightness threshold value used for identifying a level of the brightness of a particle,
wherein the reflected light particle detecting circuit specifies a pixel area in which pixels having brightness levels higher than a predetermined brightness level are aggregated in the pixel coordinates of the reflected light image as an area in which the reflected light particle is present based on a brightness distribution of an image that is acquired by binarizing the reflected light image using the brightness threshold value used for identifying the level of the brightness of the particle and detects position coordinates of the pixel located within the area in which the reflected light particle is present, and
wherein the particle information calculating circuit identifies the fine particle corresponding to the transmitted light particle that is associated with the reflected light particle as a bright-color particle having a brightness higher than the brightness threshold value used for identifying the level of brightness of the particle and identifies the fine particle corresponding to the transmitted light particle that is not associated with any reflected particle as a dark-color particle having a brightness level lower than the brightness threshold value used for identifying the level of the brightness of the particle.

6. The particle measuring device according claim 5, wherein the fine particle is a falling dust that is originated from an iron manufacturing plant according to a blast furnace method.

7. The particle measuring device according to claim 5,
wherein the transmitted light particle information calculating circuit additionally calculates a diameter of the transmitted light particle, and
wherein the particle information calculating circuit additionally calculates the diameter of the transmitted light particle as a particle diameter of the fine particle.

8. The particle measuring device according to claim 1,
wherein the reflected light image generating circuit generates a dark-background reflected light image that is acquired by imaging the fine particle in a state in which the device light emitting face luminance of the second light is set by the illumination control circuit such that the brightness level of a background of the reflected light particle on the reflected light image is lower than a first brightness threshold value used for identifying a level of the brightness of a particle,
wherein the reflected light image generating circuit generates a bright-background reflected light image that is acquired by imaging the fine particle in a state in which the device light emitting face luminance of the second light is set by the illumination control circuit such that the brightness level of a background of the reflected light particle on the reflected light image is higher than a second brightness threshold value, which is a brightness threshold value lower than the first brightness threshold value, used for identifying the level of the brightness of the particle,
wherein the reflected light particle detecting circuit specifies a pixel area in which pixels having high brightness levels are aggregated in the pixel coordinates of the reflected light image as an area in which the reflected light particle is present based on a brightness distribution of an image that is acquired by binarizing the dark-background reflected light image using the first brightness threshold value and detects position coordinates of the pixel located within the area in which the reflected light particle is present,
wherein the reflected light particle detecting circuit specifies a pixel area in which pixels having low brightness levels are aggregated in the pixel coordinates of the reflected light image as an area in which the reflected light particle is present based on a brightness distribution of an image that is acquired by binarizing the bright-background reflected light image using the second brightness threshold value and detects position coordinates of the pixel located within the area in which the reflected light particle is present, and
wherein the particle information calculating circuit identifies the fine particle corresponding to the transmitted light particle that is associated with the reflected light particle that is present within the dark-background reflected light image as a bright-color particle having a brightness level higher than the first brightness threshold value, identifies the fine particle corresponding to the transmitted light particle that is associated with the reflected light particle that is present within the bright-background reflected light image as a dark-color particle having a brightness level lower than the second brightness threshold value, and identifies the fine particle corresponding to the transmitted light particle that is not associated with any of the reflected light particles as an intermediate-color particle having an intermediate brightness level between the bright color particle and the dark color particle.

9. The particle measuring device according claim 8, wherein the fine particle is a falling dust that is originated from an iron manufacturing plant according to a blast furnace method.

10. The particle measuring device according to claim 8,
wherein the transmitted light particle information calculating circuit additionally calculates a diameter of the transmitted light particle, and
wherein the particle information calculating circuit additionally calculates the diameter of the transmitted light particle as a particle diameter of the fine particle.

11. The particle measuring device according to claim 1,
wherein the reflected light image generating circuit generates a dark-background reflected light image that is acquired by imaging the fine particle in a state in which the device light emitting face luminance of the second light is set by the illumination control circuit such that the brightness level of a background of the reflected light particle on the reflected light image is lower than a first brightness threshold value used for identifying a level of the brightness of a particle, wherein the reflected light image generating circuit generates a bright-background reflected light image that is acquired by imaging the fine particle in a state in which the device light emitting face luminance of the second light is set by the illumination control circuit such that the brightness level of a background of the reflected light particle on the reflected light image is higher than a second brightness threshold value, which is a brightness threshold value higher than the first brightness threshold value, wherein the reflected light particle detecting circuit specifies a pixel area in which pixels having brightness levels higher than a predetermined brightness level are aggregated in the pixel coordinates of the reflected light image as an area in which the reflected light particle is present based on a brightness distribution of an image that is acquired by binarizing the dark-background reflected light image using the first brightness threshold value and detects position coordinates of the pixel located within the area in which the reflected light particle is present, wherein the reflected light particle detecting circuit specifies a pixel area in which pixels having brightness levels lower than a predetermined brightness level are aggregated in the pixel coordinates of the reflected light image as an area in which the reflected light particle is present based on a brightness distribution of an image that is acquired by binarizing the bright-background reflected light image using the second brightness threshold value and detects position coordinates of the pixel located within the area in which the reflected light particle is present, and wherein the particle information calculating circuit sets the fine particle corresponding to the transmitted light particle that is associated with the reflected light particle that is present within the dark-background reflected light image as a candidate for a bright-color particle having a brightness level higher than the first brightness threshold value, sets the fine particle corresponding to the transmitted light particle that is associated with the reflected light particle that is present within the bright-background reflected light image as a candidate for a dark-color particle having a brightness level lower than the second brightness threshold value, identifies the fine particle corresponding to the transmitted light particle that is associated with both the reflected light particles that is present within the dark-background reflected light image and the reflected light particle that is present within the bright-background reflected light image as an intermediate-color particle having an intermediate brightness level between the bright-color particle and the dark-color particle, identifies the candidates for the bright-color particle that is not identified as the intermediate-color particle as the bright-color particle, and identifies the candidates for the dark-color particle that are not identified as the intermediate-color particle as the dark-color particle.

12. The particle measuring device according claim 11, wherein the fine particle is a falling dust that is originated from an iron manufacturing plant according to a blast furnace method.

13. The particle measuring device according to claim 1,
wherein the illumination control circuit, in a case where the brightness level of the reflected particle on the reflected light image is higher than a brightness threshold value used for identifying the level of the brightness of the particle, and N is a natural number, can set first device light emitting face luminance to N-th device light emitting face luminance of which the brightness levels satisfy "first brightness level<second brightness level<. . . <N-the brightness level" to the second light, wherein the reflected light image generating circuit generates first to N-th reflected light images in a state in which the device light emitting face luminance of the second light is set to the first device light emitting face luminance to the N-th device light emitting face luminance, wherein the reflected light particle detecting circuit, based on a brightness distribution of an image that is acquired by binarizing the first to N-th reflected light images using a brightness threshold value used for identifying a level of the brightness of the particle, specifies a pixel area in which pixels having brightness levels lower than a predetermined brightness level are aggregated in the pixel coordinates of the first to N-th reflected light images as an area in which the reflected light particle is present and detects position coordinates of pixels present within the area in which the reflected light particle is present, wherein, when n=1 to N, the association processing circuit compares a position and a size of the reflected light particle detected in the n-th reflected light image with the position and the size of the transmitted light particle (in the case of n=1, all the transmitted light particles) that is not associated with the reflected light particle detected in the (n−1)-th or a prior reflected light image and associates the transmitted light particle and the reflected light particle having differences in the position and the size are within predetermined ranges, and wherein the particle information calculating circuit identifies the brightness level of the fine particle corresponding to the transmitted light particle that is associated with the reflected light particle that is present within the first to N-th reflected light images as first to N-th brightness levels (first brightness level<second brightness level<. . . <N-th brightness level) and identifies the fine particle corresponding to the transmitted light particle that is not associated with any reflected light particle as a particle having a highest brightness level.

14. The particle measuring device according claim 13, wherein the fine particle is a falling dust that is originated from an iron manufacturing plant according to a blast furnace method.

15. The particle measuring device according to claim 1, wherein the fine particle is a falling dust that is originated from an iron manufacturing plant according to a blast furnace method.

16. The particle measuring device according to claim 1,
wherein the transmitted light particle information calculating circuit additionally calculates a diameter of the transmitted light particle, and wherein the particle information calculating circuit additionally calculates the diameter of the transmitted light particle as a particle diameter of the fine particle.

17. The particle measuring device according claim 1, wherein the fine particle is a falling dust that is originated from an iron manufacturing plant according to a blast furnace method.

18. The particle measuring device according to claim 1,
wherein the reflected light image generating circuit generates the reflected light image by imaging the fine particle in the state being controlled by the illumination control circuit such that the device light emitting face luminance of the second light is the predetermined luminance which is set in accordance with one, two or more conditions including one or more of condition in which the luminance is other than zero.

19. The particle measuring device according to claim 1, wherein the reflected light image generating circuit generates the reflected light image by imaging the fine particle in the state being controlled by the illumination control circuit such that the device light emitting face luminance of the second light is the predetermined luminance which is set in accordance with one, two or more conditions in which the luminance is other than zero.

20. A method of measuring a position, a size, and a brightness level of a fine particle by using a particle measuring device including:
a stage which is a transparent flat plate and on which a transparent substrate having an opaque fine particle sprayed thereon is placed or the fine particle is directly sprayed;
an imaging device that is disposed on a placement face side of the stage and images the fine particle;
a reflected light illuminating device that is disposed on a placement face side of the stage and emits first light having predetermined device light emitting face luminance toward the stage; and
a transmitted light illuminating device that is disposed on a side of the stage that is opposite to the placement face and emits second light having predetermined device light emitting face luminance toward the stage, the method comprising:
generating a transmitted light image acquired by imaging the fine particle using the imaging device in a state in which the device light emitting face luminance of the second light is predetermined luminance other than zero, and the device light emitting face luminance of the first light is zero;
generating a reflected light image acquired by imaging the fine particle using the imaging device in a state in which the device light emitting face luminance of the second light is predetermined luminance set in accordance with one or more conditions, and the device light emitting face luminance of the first light is predetermined luminance other than zero; and
image processing by associating the transmitted light particle and the reflected light particle having a difference between the positions and the sizes within a predetermined range, by comparing positions and sizes of one, two, or more transmitted light particles that are identified as candidates for a captured image of the fine particle within the transmitted light image and positions and sizes of one, two, or more reflected light particles that are identified as candidates for a captured image of the fine particle within the reflected light image, calculating the position and the size of the transmitted light particle as a position and a size of the fine particle, and calculating a representative brightness level of the reflected light particles or the transmitted light particles as a brightness level of the fine particle, based on a result of the association,
wherein the representative brightness level represents a whole pixel area which is identified as the particle, and the representative brightness level is an average value of brightness of each of pixels within the pixel area, a median value of the brightness of each of the pixels, an average value of the brightness of the pixels within the pixel area from which a pixel having a maximum brightness level and a pixel having a lowest brightness level are eliminated, or an average value of the brightness of the pixels within the pixel area from which a pixel within a peripheral edge portion of the pixel area, and
wherein the image processing includes
transmitted light particle detecting by specifying a pixel area in which pixels having brightness levels lower than a predetermined brightness level are aggregated in pixel coordinates of the transmitted light image as an area in which the transmitted light particle is present based on an image brightness distribution that is acquired by binarizing the transmitted light image using a predetermined brightness threshold value and detecting position coordinates of a pixel within the area in which the transmitted light particle is present;
transmitted light particle information calculating by calculating at least the position and the size of the transmitted light particle based on a detection result of the transmitted light particle detecting circuit;
reflected light particle detecting by specifying a pixel area in which pixels each having a brightness level difference from a peripheral pixel that is a predetermined value or more are aggregated in pixel coordinates of the reflected light image as an area in which the reflected light particle is present based on a brightness distribution of the reflected light image and detecting position coordinates of a pixel within the area in which the reflected light particle is present;
reflected light particle information calculating by calculating at least the position and the size of the reflected light particle based on a detection result acquired by the reflected light particle detecting circuit;
association processing by comparing the position and the size of the reflected light particle with the positions and the sizes of all the transmitted light particles based on a calculation result of the transmitted light particle information calculating circuit and a calculation result of the reflected light particle information calculating circuit, associating the transmitted light particle and the reflected light particle having differences in the position and the size that are within predetermined ranges with each other, and excluding the reflected light particle that is not associated with any one of the transmitted light particles from a candidate for a captured image of the fine particle; and
particle information calculating by calculating the position and the size of the transmitted light particle as the position and the size of the fine particle, calculating the representative brightness level of the reflected light particle that is associated with the transmitted light particle as a brightness level of the fine particle, and calculating the brightness level of the transmitted light particle that is not associated with any one of the reflected light particles as a predetermined brightness level.

21. The particle measuring method according to claim 20, wherein the fine particle is a falling dust that is originated from an iron manufacturing plan according to a blast furnace method.

22. The particle measuring method according to claim 20, wherein, when the reflected light image is generated, the device light emitting face luminance of the second light is the predetermined luminance which is set in accordance with one, two or more conditions including one or more of condition in which the luminance is other than zero.

23. The particle measuring method according to claim 20, wherein, when the reflected light image is generated, the device light emitting face luminance of the second light is the predetermined luminance which is set in accordance with one, two or more conditions in which the luminance is other than zero.

* * * * *